US008652781B2

(12) United States Patent
Korlach

(10) Patent No.: US 8,652,781 B2
(45) Date of Patent: *Feb. 18, 2014

(54) COGNATE SAMPLING KINETICS

(75) Inventor: Jonas Korlach, Newark, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 381 days.

This patent is subject to a terminal disclaimer.

(21) Appl. No.: 13/032,478

(22) Filed: Feb. 22, 2011

(65) Prior Publication Data

US 2011/0244447 A1  Oct. 6, 2011

Related U.S. Application Data

(63) Continuation-in-part of application No. 12/584,481, filed on Sep. 4, 2009, now Pat. No. 8,530,164, and a continuation-in-part of application No. 12/370,472, filed on Feb. 12, 2009, now Pat. No. 8,252,911.

(60) Provisional application No. 61/306,407, filed on Feb. 19, 2010, provisional application No. 61/094,843, filed on Sep. 5, 2008, provisional application No. 61/065,439, filed on Feb. 12, 2008.

(51) Int. Cl.
*C12Q 1/68* (2006.01)
*C12P 19/34* (2006.01)
*C07H 21/02* (2006.01)

(52) U.S. Cl.
USPC .......................... 435/6.12; 536/22.1; 435/91.2

(58) Field of Classification Search
None
See application file for complete search history.

(56) References Cited

U.S. PATENT DOCUMENTS

| | | |
|---|---|---|
| 5,001,050 A | 3/1991 | Blanco et al. |
| 5,409,811 A | 4/1995 | Tabor et al. |
| 6,165,765 A | 12/2000 | Hong et al. |
| 6,399,320 B1 | 6/2002 | Markau et al. |
| 6,399,335 B1 | 6/2002 | Kao et al. |
| 6,447,724 B1 | 9/2002 | Jensen et al. |
| 6,610,486 B1 | 8/2003 | Dahlhauser |
| 6,762,048 B2 | 7/2004 | Williams et al. |
| 6,787,308 B2 | 9/2004 | Balasubramanian et al. |
| 6,917,726 B2 | 7/2005 | Levene et al. |
| 6,936,702 B2 | 8/2005 | Williams et al. |
| 7,041,812 B2 | 5/2006 | Kumar et al. |
| 7,057,026 B2 | 6/2006 | Barnes et al. |
| 7,315,019 B2 | 1/2008 | Turner et al. |
| 2006/0051807 A1 | 3/2006 | Fuller |
| 2006/0063173 A1 | 3/2006 | Williams et al. |
| 2007/0036511 A1 | 2/2007 | Lundquist et al. |
| 2007/0077564 A1 | 4/2007 | Roitman et al. |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2008/0030628 A1 | 2/2008 | Lundquist et al. |
| 2008/0108082 A1 | 5/2008 | Rank et al. |
| 2008/0212960 A1 | 9/2008 | Lundquist et al. |
| 2008/0299565 A1 | 12/2008 | Schneider et al. |
| 2009/0029385 A1 | 1/2009 | Christians et al. |
| 2009/0280538 A1 | 11/2009 | Patel et al. |
| 2010/0112645 A1 | 5/2010 | Clark et al. |

FOREIGN PATENT DOCUMENTS

| | | |
|---|---|---|
| WO | 02085088 A2 | 10/2002 |
| WO | 2007075987 A2 | 7/2007 |
| WO | 2007076057 A2 | 7/2007 |
| WO | 2007123763 A2 | 11/2007 |
| WO | 2007137060 | 11/2007 |
| WO | 2008051530 A2 | 5/2008 |
| WO | 2008154317 A1 | 12/2008 |
| WO | 2009102470 A2 | 8/2009 |
| WO | 2009145828 A2 | 12/2009 |

OTHER PUBLICATIONS

International Search Report and Written Opinion dated Apr. 19, 2010 for related case PCT/US2009/004993.
International Preliminary Report on Patentability dated Mar. 17, 2011 for related case PCT/US2009/004993.
Berman et al. "Structures of phi29 polymerase complexes with substrate: the mechanism of translocation in polymerases" EMBO J (2007) 26:3494-3505.
Blanco et al. "Mutational analysis of bacteriophage phi29 DNA polymerase" Meth in Enzym (1995) 262:283-294.
Blasco et al. "phi29 DNA polymerase active site" J Biol Chem (1993) 268(22):16763-16770.
Eid et al. "Real-time DNA sequencing from single polymerase molecules" Science (2009) 323(5910):133-138.
Korlach et al., "Selective aluminum passivation for targeted immobilization of single DNA polymerase molecules in zero-mode waveguide structures" PNAS (2008) 105(4):1176-1181.
Korlach et al,, "Long, Processive Enzymatic DNA Synthesis Using 100% Dye-Labeled Terminal Phosphate-Linked Nucleotides" Nucleosides, and Nucleotides and Nucleic Acids (2008) 27:1072-1083.
Levene et al., "Zero-mode waveguides for single moledule analysis at high concentrations" Science (2003) 299:682-686.
Lundquist et al. "Parallel confocal detection of single molecules in real time" Opt Lett (2008) 33(9):1026-1028.

(Continued)

*Primary Examiner* — Prabha Chunduru
(74) *Attorney, Agent, or Firm* — Robert H. Reamey

(57) ABSTRACT

Provided are methods and compositions for measuring the transient binding of nucleotides and nucleotide analogs under conditions where the nucleotides or nucleotide analogs are unincorporable. The transient binding can be determined under single molecule observation conditions providing information about the kinetics of nucleotide analog sampling of the active site of the enzyme. The methods can be used for polymerase enzyme development, mechanistic understanding, and drug discovery.

8 Claims, 10 Drawing Sheets

(56) References Cited

OTHER PUBLICATIONS

Miyake, T. et al., "Real-Time Imaging of Single-Molecule Fluorescence with a Zero-Mode Waveguide for the Analysis of Protein-Protein Interaction" Anal Chem (2008) 80:6018-6022.
Xie, S. et al. "Single-molecule enzymology" J Biol Chem (1999) 274(23):15967-15970.
Zhou et al. "Kinetic analysis of sequential multistep reactions" J Phys Chem B (2007) 111:13600-13610.
International Search Report and Written Opinion dated Apr. 19, 2010 for related case PCT/US2010/004993.
Internatioanl Preliminary Report on Patentability dated Mar. 17, 2011 for related case PCT/US2010/004993.
International Search Report and Written Opinion dated Dec. 1, 2009 for related case PCT/US2009/002003.
International Preliminary Report on Patentability dated Oct. 14, 2010 for related case PCT/US2009/002003.
International Search Report and Written Opinion dated Jan. 29, 2010 for related case PCT/US2009/001974.
International Preliminary Report on Patentability dated Oct. 14, 2010 for related case PCT/US2009/001974.

```
                         SEQUENCE LISTING

<160> NUMBER OF SEQ ID NOS: 3

<210> SEQ ID NO 1
<211> LENGTH: 588
<212> TYPE: PRT
<213> ORGANISM: Artificial Sequence
<220> FEATURE:
<223> OTHER INFORMATION: translocation fusion protein - no linker

<400> SEQUENCE: 1

Met Glu Met Lys His Met Pro Arg Lys Met Tyr Ser Cys Asp Phe Glu
1               5                   10                  15

Thr Thr Thr Lys Val Glu Asp Cys Arg Val Trp Ala Tyr Gly Tyr Met
                20                  25                  30

Asn Ile Glu Asp His Ser Glu Tyr Lys Ile Gly Asn Ser Leu Asp Glu
            35                  40                  45

Phe Met Ala Trp Val Leu Lys Val Gln Ala Asp Leu Tyr Phe His Asp
        50                  55                  60

Leu Lys Phe Asp Gly Ala Phe Ile Ile Asn Trp Leu Glu Arg Asn Gly
65                  70                  75                  80

Phe Lys Trp Ser Ala Asp Gly Leu Pro Asn Thr Tyr Asn Thr Ile Ile
                85                  90                  95

Ser Arg Met Gly Gln Trp Tyr Met Ile Asp Ile Cys Leu Gly Tyr Lys
            100                 105                 110

Gly Lys Arg Lys Ile His Thr Val Ile Tyr Asp Ser Leu Lys Lys Leu
        115                 120                 125

Pro Phe Pro Val Lys Lys Ile Ala Lys Asp Phe Lys Leu Thr Val Leu
    130                 135                 140

Lys Gly Asp Ile Asp Tyr His Lys Glu Arg Pro Val Gly Tyr Lys Ile
145                 150                 155                 160

Thr Pro Glu Glu Tyr Ala Tyr Ile Lys Asn Asp Ile Gln Ile Ile Ala
                165                 170                 175

Glu Ala Leu Leu Ile Gln Phe Lys Gln Gly Leu Asp Arg Met Thr Ala
            180                 185                 190

Gly Ser Asp Ser Leu Lys Gly Phe Lys Asp Ile Ile Thr Thr Lys Lys
        195                 200                 205

Phe Lys Lys Val Phe Pro Thr Leu Ser Leu Gly Leu Asp Lys Glu Val
    210                 215                 220

Arg Tyr Ala Tyr Arg Gly Gly Phe Thr Trp Leu Asn Asp Arg Phe Lys
225                 230                 235                 240

Glu Lys Glu Ile Gly Glu Gly Met Val Phe Asp Val Asn Ser Leu Tyr
                245                 250                 255

Pro Ala Gln Met Tyr Ser Arg Leu Leu Pro Tyr Gly Glu Pro Ile Val
            260                 265                 270

Phe Glu Gly Lys Tyr Val Trp Asp Glu Asp Tyr Pro Leu His Ile Gln
        275                 280                 285

His Ile Arg Cys Glu Phe Glu Leu Lys Glu Gly Tyr Ile Pro Thr Ile
```

```
                290                 295                 300
Gln Ile Lys Arg Ser Arg Phe Tyr Lys Gly Asn Glu Tyr Leu Lys Ser
305                 310                 315                 320

Ser Gly Gly Glu Ile Ala Asp Leu Trp Leu Ser Asn Val Asp Leu Glu
                325                 330                 335

Leu Met Lys Glu His Tyr Asp Leu Tyr Asn Val Glu Tyr Ile Ser Gly
                340                 345                 350

Leu Lys Phe Lys Ala Thr Thr Gly Leu Phe Lys Asp Phe Ile Asp Lys
                355                 360                 365

Trp Thr Tyr Ile Lys Thr Thr Ser Glu Gly Ala Ile Lys Gln Leu Ala
                370                 375                 380

Lys Leu Met Leu Asn Ser Leu Tyr Gly Lys Phe Ala Ser Asn Pro Asp
385                 390                 395                 400

Val Thr Gly Lys Val Pro Tyr Leu Lys Glu Asn Gly Ala Leu Gly Phe
                405                 410                 415

Arg Leu Gly Glu Glu Thr Lys Asp Pro Val Tyr Thr Pro Met Gly
                420                 425                 430

Val Phe Ile Thr Ala Trp Ala Arg Tyr Thr Thr Ile Thr Ala Ala Gln
                435                 440                 445

Ala Cys Tyr Asp Arg Ile Ile Tyr Cys Asp Thr Asp Ser Ile His Leu
450                 455                 460

Thr Gly Thr Glu Ile Pro Asp Val Ile Lys Asp Ile Val Asp Pro Lys
465                 470                 475                 480

Lys Leu Gly Tyr Trp Ala His Glu Ser Thr Phe Lys Arg Ala Lys Tyr
                485                 490                 495

Leu Arg Gln Lys Thr Tyr Ile Gln Asp Ile Tyr Met Lys Glu Val Asp
                500                 505                 510

Gly Lys Leu Val Glu Gly Ser Pro Asp Asp Tyr Thr Asp Ile Lys Phe
                515                 520                 525

Ser Val Lys Cys Ala Gly Met Thr Asp Lys Ile Lys Lys Glu Val Thr
530                 535                 540

Phe Glu Asn Phe Lys Val Gly Phe Ser Arg Lys Met Lys Pro Lys Pro
545                 550                 555                 560

Val Gln Val Pro Gly Gly Val Val Leu Val Asp Asp Thr Phe Thr Ile
                565                 570                 575

Lys Gly His His His His His His His His His
                580                 585

<210> SEQ ID NO 2
<211> LENGTH: 598
<212> TYPE: PRT
<213> ORGANISM: Artificial Sequence
<220> FEATURE:
<223> OTHER INFORMATION: translocation fusion protein - Ser3Gly linker

<400> SEQUENCE: 2

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asp Leu Lys
50                  55                  60

Phe Asp Gly Ala Phe Ile Ile Asn Trp Leu Glu Arg Asn Gly Phe Lys
65                  70                  75                  80
```

-continued

```
Trp Ser Ala Asp Gly Leu Pro Asn Thr Tyr Asn Thr Ile Ile Ser Arg
                85                  90                  95
Met Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
        115                 120                 125
Pro Val Lys Lys Ile Ala Lys Asp Phe Lys Leu Thr Val Leu Lys Gly
    130                 135                 140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Gly Phe Lys Asp Ile Ile Thr Thr Lys Lys Phe Lys
        195                 200                 205
Lys Val Phe Pro Thr Leu Ser Leu Gly Leu Asp Lys Glu Val Arg Tyr
    210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
        275                 280                 285
Arg Cys Glu Phe Glu Leu Lys Glu Gly Tyr Ile Pro Thr Ile Gln Ile
    290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
        355                 360                 365
Tyr Ile Lys Thr Thr Ser Tyr Gly Ala Ile Lys Gln Leu Ala Lys Leu
    370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
        435                 440                 445
Tyr Asp Arg Ile Ile Tyr Cys Asp Thr Asp Ser Ile His Leu Thr Gly
    450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Tyr
```

```
                    500             505             510
Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
                565                 570                 575

Gly Gly Ser Gly Gly Gly Ser Gly Gly Gly Ser Gly His His His His
            580                 585                 590

His His His His His His
            595

<210> SEQ ID NO 3
<211> LENGTH: 572
<212> TYPE: PRT
<213> ORGANISM: phage phi 29

<400> SEQUENCE: 3

Met Pro Arg Lys Met Tyr Ser Cys Asp Phe Glu Thr Thr Thr Lys Val
1               5                   10                  15

Glu Asp Cys Arg Val Trp Ala Tyr Gly Tyr Met Asn Ile Glu Asp His
            20                  25                  30

Ser Glu Tyr Lys Ile Gly Asn Ser Leu Asp Glu Phe Met Ala Trp Val
        35                  40                  45

Leu Lys Val Gln Ala Asp Leu Tyr Phe His Asn Leu Lys Phe Asp Gly
    50                  55                  60

Ala Phe Ile Ile Asn Trp Leu Glu Arg Asn Gly Phe Lys Trp Ser Ala
65                  70                  75                  80

Asp Gly Leu Pro Asn Thr Tyr Asn Thr Ile Ile Ser Arg Met Gly Gln
                85                  90                  95

Trp Tyr Met Ile Asp Ile Cys Leu Gly Tyr Lys Gly Lys Arg Lys Ile
            100                 105                 110

His Thr Val Ile Tyr Asp Ser Leu Lys Lys Leu Pro Phe Pro Val Lys
        115                 120                 125

Lys Ile Ala Lys Asp Phe Lys Leu Thr Val Leu Lys Gly Asp Ile Asp
    130                 135                 140

Tyr His Lys Glu Arg Pro Val Gly Tyr Glu Ile Thr Pro Asp Glu Tyr
145                 150                 155                 160

Ala Tyr Ile Lys Asn Asp Ile Gln Ile Ile Ala Glu Ala Leu Leu Ile
                165                 170                 175

Gln Phe Lys Gln Gly Leu Asp Arg Met Thr Ala Gly Ser Asp Ser Leu
            180                 185                 190

Lys Gly Phe Lys Asp Ile Ile Thr Thr Lys Lys Phe Lys Lys Val Phe
        195                 200                 205

Pro Thr Leu Ser Leu Gly Leu Asp Lys Glu Val Arg Tyr Ala Tyr Arg
    210                 215                 220

Gly Gly Phe Thr Trp Leu Asn Asp Arg Phe Lys Glu Lys Glu Ile Gly
225                 230                 235                 240

Glu Gly Met Val Phe Asp Val Asn Ser Leu Tyr Pro Ala Gln Met Tyr
                245                 250                 255

Ser Arg Leu Leu Pro Tyr Gly Glu Pro Ile Val Phe Glu Gly Lys Tyr
            260                 265                 270

Val Trp Asp Glu Asp Tyr Pro Leu His Ile Gln His Ile Arg Cys Glu
```

-continued

```
                275                 280                 285
Phe Glu Leu Lys Glu Gly Tyr Ile Pro Thr Ile Gln Ile Lys Arg Ser
            290                 295                 300
Arg Phe Tyr Lys Gly Asn Glu Tyr Leu Lys Ser Ser Gly Gly Glu Ile
305                 310                 315                 320
Ala Asp Leu Trp Val Ser Asn Val Asp Leu Glu Leu Met Lys Glu His
                325                 330                 335
Tyr Asp Leu Tyr Asn Val Glu Tyr Ile Ser Gly Leu Lys Phe Lys Ala
            340                 345                 350
Thr Thr Gly Leu Phe Lys Asp Phe Ile Asp Lys Trp Thr His Ile Lys
            355                 360                 365
Thr Thr Ser Glu Gly Ala Ile Lys Gln Leu Ala Lys Leu Met Leu Asn
    370                 375                 380
Ser Leu Tyr Gly Lys Phe Ala Ser Asn Pro Asp Val Thr Gly Lys Val
385                 390                 395                 400
Pro Tyr Leu Lys Glu Asn Gly Ala Leu Gly Phe Arg Leu Gly Glu Glu
                405                 410                 415
Glu Thr Lys Asp Pro Val Tyr Thr Pro Met Gly Val Phe Ile Thr Ala
            420                 425                 430
Trp Ala Arg Tyr Thr Thr Ile Thr Ala Ala Gln Ala Cys Phe Asp Arg
            435                 440                 445
Ile Ile Tyr Cys Asp Thr Asp Ser Ile His Leu Thr Gly Thr Glu Ile
    450                 455                 460
Pro Asp Val Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Met Lys Glu Val Asp Gly Lys Leu Val Glu
            500                 505                 510
Gly Ser Pro Asp Asp Tyr Thr Thr Ile Lys Phe Ser Val Lys Cys Ala
            515                 520                 525
Gly Met Thr Asp Lys Ile Lys Lys Glu Val Thr Phe Glu Asn Phe Lys
    530                 535                 540
Val Gly Phe Ser Arg Lys Met Lys Pro Lys Pro Val Gln Val Pro Gly
545                 550                 555                 560
Gly Val Val Leu Val Asp Asp Thr Phe Thr Ile Lys
                565                 570
```

COGNATE SAMPLING KINETICS

CROSS-REFERENCE TO RELATED APPLICATIONS

This application claims the benefit of Provisional U.S. Patent Application No. 61/306,407, filed Feb. 19, 2010. This application is a Continuation-in-Part of U.S. patent application Ser. No. 12/584,481, filed Sep. 4, 2009 which claims a benefit of Provisional U.S. Patent Application No. 61/094,843, filed Sep. 5, 2008. This application is also a Continuation-in-Part of U.S. patent application Ser. No. 12/370,472, filed Feb. 12, 2009 which claims the benefit of Provisional U.S. Patent Application No. 61/065,439 filed Feb. 12, 2008. The full disclosures of each of these applications are incorporated herein by reference in their entirety for all purposes.

BACKGROUND OF THE INVENTION

High throughput sequencing has become a central tool in the field of biotechnology and is revolutionizing personalized medicine. Many diseases and/or disorders are genetic in origin. Acquiring the genomic sequence of individual patients in a comprehensive, rapid and cost-effective manner enhances the ability of medical professionals to diagnose diseases or identify predispositions to diseases or other genetic-based disorders. Genomic sequence information also enhances the treatment of diseases by providing doctors with information regarding the efficacy of a given therapy for a particular individual.

One approach aimed at efficiently obtaining the complete genomic sequence of an organism is sequencing by incorporation, where the identity of the sequence of nucleotides in a template nucleic acid polymer is determined by identifying each complementary base that is added to a nascent strand being synthesized against the template sequence, as such bases are added. While detection of added bases may be a result of detecting a byproduct of the synthesis or extension reaction, e.g., detecting released pyrophosphate, in many systems and processes, added bases are labeled with fluorescent dyes that permit their detection. By uniquely labeling each base with a distinguishable fluorescent dye, one attaches a distinctive detectable characteristic to each dye that is incorporated, and as a result provides a basis for identification of an incorporated base, and by extension, its complementary base upon the template sequence.

During sequencing by incorporation, nucleotide (or nucleotide analog) incorporation events are detected in real-time as the bases are incorporated into the extension product. This can be accomplished by immobilizing the complex within an optically confined space or otherwise resolved as an individual molecular complex. Some sequencing by incorporation methods employ nucleotide analogs that include fluorescent labels coupled to the polyphosphate chain of the analog, which are then exposed to the complex. Upon incorporation, the nucleotide—along with its fluorescent label—is retained by the complex for a time and in a manner that permits the detection of a signal "pulse" from the fluorescent label at the incorporation site. Upon completion of incorporation, all but the alpha phosphate group of the nucleotide is cleaved away, liberating the label from retention by the complex, and diffusing the signal from that label.

Thus, during an incorporation event, a complementary nucleotide analog, including its fluorescent label, is effectively "immobilized" for a time at the incorporation site, and the fluorescent label is subsequently released and diffuses away when incorporation is completed. Detecting the localized "pulses" of fluorescent tags immobilized at the incorporation site, and distinguishing those pulses from a variety of other signals and background noise, allows bases to be called in real-time as they are incorporated. Further details regarding base calling during sequencing by incorporation methods are found in Tomaney et al. PCT Application Serial No. PCT/US2008/065996 METHODS AND PROCESSES FOR CALLING BASES IN SEQUENCING BY INCORPORATION METHODS, incorporated herein by reference in its entirety for all purposes.

While these sequencing methods can generate useful information about nucleic acid sequences, there is other information about the manner in which an enzyme acts on a substrate that single molecule analysis can reveal. Compositions and methods for revealing such information is desirable.

SUMMARY OF THE INVENTION

Altered reaction conditions and modified DNA polymerases can find use in such applications as, e.g., single-molecule sequencing (SMS), genotyping analyses such as SNP genotyping using single-base extension methods, and real-time monitoring of amplification, e.g., real time PCR. The invention provides methods and compositions for observing the interaction between a single polymerase enzyme and a substrate under conditions where the substrate will not incorporate into a growing, nascent strand. We have found that the interactions between a polymerase enzyme and a non-incorporable substrate under single molecule conditions can provide kinetic information that cannot be seen in classic ensemble experiments, and also cannot be seen when observing a single polymerase while it is performing nucleic acid synthesis. In the case of classic ensemble methods in which a population of enzyme is observed, the kinetics behavior of the enzymes is lost because each of the enzymes in the ensemble is proceeding at a different time, and the signal that is observed is an amalgam of the various processes. In the case of observing a single polymerase enzymes while it is adding nucleotides, the kinetic behavior that is observed when the enzyme is incorporating nucleotides is different than the kinetic behavior when the enzyme is unable to perform an incorporation reaction. For example, information about how the nascent strand is held within the enzyme when being sampled can be observed.

In addition invention provides methods of sequencing a nucleic acid template, which methods utilize signal pulses or signatures from branch fraction nonincorporation events (and, optionally, actual nucleotide incorporation events) to determine which nucleotide is incorporated at a particular site/position of the template nucleic acid. The invention further provides methods that modulate (e.g., increase) the branching rate of a polymerization reaction to facilitate identifying which nucleotide is incorporated at a particular site. A nucleic acid sequencing system that detects and utilizes signal pulses or signatures from branch fraction nonincorporation events to determine the sequence of a template nucleic acid is also provided by the invention. The invention further provides compositions that include modified recombinant polymerases that exhibit properties, e.g., increased branching fraction, delayed translocation or increased nucleotide or nucleotide analog residence time, which can be particularly desirable for these applications. These improved polymerase properties can facilitate readout accuracy. In addition, the invention provides methods of generating the modified polymerases of the invention and methods in which such polymerases can be used to e.g., sequence a DNA template and/or make a DNA.

In one aspect, the invention provides methods for determining which labeled nucleotide is incorporated at a particular site during a template dependent polymerization reaction. The methods include incorporating the nucleotide into a nucleic acid polymer, whereby signal pulses or signatures are generated from branch fraction nonincorporation events and, optionally, actual nucleotide incorporation events for the site. The methods additionally include monitoring a time course of at least branch fraction signal pulses or signatures produced by the polymerization reaction and assigning which nucleotide is incorporated at the site, using at least signal pulses or signatures from branch fraction nonincorporation sampling events. The methods optionally comprise counting or estimating the number of redundant iterative sampling signal pulses per incorporation event, or determining an average number of redundant signal pulses per incorporation event. Optionally, the polymerization reaction is a high branch fraction polymerization reaction, where the branch fraction is optionally 70% or more, 80% or more, or 90% or more.

The methods described above optionally include at least one species of metal ion, which metal ion increases the frequency of branch fraction nonincorporation events in the reaction. Example metal ions include: $Mg^{++}$, $Mn^{++}$, $Zn^{++}$, $Co^{++}$, $Ca^{++}$, $Fe^{++}$, $Cr^{++}$ and $Sr^{++}$. The methods described above optionally comprise both $Mg^{++}$ and $Mn^{++}$, e.g., where the concentration of $Mg^{++}$ is higher than the concentration of $Mn^{++}$.

The methods described above optionally include a Φ29, B103, GA-1, PZA, Φ15, BS32, M2Y, Nf, G1, Cp-1, PRD1, PZE, SF5, Cp-5, Cp-7, PR4, PR5, PR722, L17, T4 or T7 DNA polymerase, or a modified recombinant DNA polymerase thereof. The modified recombinant polymerase can optionally exhibit a higher branching fraction as compared to a corresponding wild-type polymerase, or an increased exonuclease rate that is about 10% to 50% as compared to its polymerization rate.

The methods described above optionally include branch fraction nonincorporation events that comprise iterative sampling of labeled unincorporatable nucleotide analogs, optionally including actual nucleotide incorporation events that comprise incorporation of unlabeled nucleotides. Actual nucleotide incorporation events optionally include incorporation of nucleotides that are differentially labeled as compared to the unincorporatable nucleotides. In one example, labeled unincorporatable nucleotide analogs comprise a link between an alpha and beta phosphate group that is not hydrolyzable by a polymerase enzyme.

The methods described above optionally include a polymerase enzyme, polymerase reaction conditions, and/or polymerase reaction substrates that are selected such that the polymerization reaction exhibits two kinetically observable steps within an observable phase of the polymerase reaction. The two kinetically observable steps are optionally steps which proceed in a bright phase or a dark phase, and the polymerase enzyme optionally comprises a modified recombinant Φ29, B103, GA-1, PZA, Φ15, BS32, M2Y, Nf, G1, Cp-1, PRD1, PZE, SF5, Cp-5, Cp-7, PR4, PR5, PR722, L17, T4 or T7 DNA polymerase. Optionally, the polymerase reaction conditions can include, e.g., a selected metal cofactor concentration, a selected pH, a selected temperature, an enzyme activity modulator, $D_2O$, an organic solvent, and a buffer.

The methods described above optionally comprise branch fraction nonincorporation events that comprise noncognate branch fraction nonincorporation events. Branch fraction signal pulses or signatures are optionally generated from noncognate branching events of a nucleotide analog, e.g., guanine and thymine.

The reaction of the methods described above is optionally reacted in a DNA sequencing system, where the DNA sequencing system optionally comprises a zero mode waveguide or nanohole.

Assigning the nucleotide in the methods described above optionally comprises applying a statistical model to the signal pulses or signatures generated from branch fraction nonincorporation events, signal pulses generated from actual nucleotide incorporation events, or both, which statistical model assigns a likelihood that the signal pulses or signatures correspond to an incorporation event.

The methods described above optionally comprise performing an additional template dependent polymerization reaction under high processivity reaction conditions, monitoring a second time course of signal pulses or signatures produced by the additional polymerization reaction, and compiling sequencing information derived from the second time course of signal pulses or signatures with sequencing information derived from the time course of branch fraction signal pulses or signatures.

In another aspect, the invention provides multi-modal sequencing methods that comprise performing a first template dependent sequencing reaction in a first mode comprising a first set of reaction conditions and collecting initial sequencing information produced by the first sequencing reaction. Additionally, the methods can include performing a second sequencing reaction of the template, or a copy thereof, in a second mode that includes a second set of reaction conditions and collecting additional sequencing information produced by the second sequencing reaction. The methods can include compiling the initial and additional sequencing information to provide a sequence of at least a portion of the template.

The second sequencing reaction of the methods described above is optionally produced by altering one or more reaction conditions of the first sequencing reaction, and the initial and additional sequencing information are collected in real time. Optionally, altering one or more reaction conditions comprises adding one or more polymerase cofactors to the first sequencing reaction, where the cofactors of the first sequencing reaction are optionally $Mn^{++}$ or $Mg^{++}$. Both the first and second sequencing reactions comprise single template molecule sequencing reactions. For example, the first mode can produce a higher branch fraction than the second mode. The second mode optionally produces longer read lengths than the first mode. The template of the methods described above is optionally adapted to sequencing, e.g., a single circular template molecule, e.g., where the method includes switching between the first and second modes.

The invention also provides methods for determining which of two or more labeled nucleotides is incorporated at a site during a template-dependent polymerization reaction. The methods include incorporating the nucleotide into a nucleic acid polymer produced by the polymerization reaction, whereby signal pulses or signatures are generated. The methods further include monitoring the pulses or signatures, and using the presence of multiple pulses corresponding to the nucleotide, or identical molecules thereof, to assign which labeled nucleotide is incorporated at the site. The multiple pulses optionally include 2 to 20 pulses and can be generated from branch fraction nonincorporation events, which events are optionally induced by sequencing compositions that include at least one species of metal ion. Metal ions of the method can include $Mg^{++}$, $Mn^{++}$, $Zn^{++}$, $Co^{++}$, $Ca^{++}$, $Fe^{++}$, Cr$^{++}$ and Sr$^{++}$. Optionally, using the presence of multiple pulses comprises distinguishing incorporation and nonincorporation signals to assign which labeled nucleotide was incorporated at the site.

In another aspect, the invention provides nucleic acid sequencing systems that, during operation of the system, sequences a nucleic acid. The nucleic acid sequencing system comprises a signal detector that detects at least signal pulses or signatures from branch fraction nonincorporation events during sequencing of a template nucleic acid, system instructions or software that assigns a sequence based upon detection of at least signal pulses or signatures from branch fraction nonincorporation events, and a user output module that displays the sequence to the user.

Signal pulses or signatures from branch fraction nonincorporation events of the nucleic acid sequencing systems described above are optionally generated during a first sequencing mode, where the signal detector subsequently detects signal pulses generated during a low branch fraction second sequencing mode, and where the system instructions assign a sequence based upon detection of signal pulses or signatures from the first and second sequencing modes.

The nucleic acid sequencing systems optionally comprise a zero-mode waveguide or nanohole proximal to the signal detector, where during operation of the system, a sequencing reaction is contained by the zero-mode waveguide or nanohole.

In another aspect, the invention provides compositions that include a modified recombinant nucleic acid polymerase that exhibits an altered property selected from an increased branching fraction during a polymerization by the polymerase, an altered translocation property of the polymerase during a polymerization reaction, and a combination of these two altered properties, where the altered property or properties is altered as compared to a corresponding wild-type polymerase.

The modified recombinant polymerase of the compositions described above can optionally be a modified recombinant Φ29, B103, GA-1, PZA, Φ15, BS32, M2Y, Nf, G1, Cp-1, PRD1, PZE, SF5, Cp-5, Cp-7, PR4, PR5, PR722, L17, T4, or T7 polymerase. Other available polymerases can also be used as starting points for modification to alter translocation rates or to modulate branch fraction activity, such as reverse transcriptases and DNA-dependent RNA polymerases.

The modified recombinant polymerase exhibiting an increased branching fraction can optionally comprise at least one amino acid substitution or deletion or combination of substitutions or deletions selected from: N62D and Y454A; D362S; Y259H; F237Y; L381I; Y369H; H461Y; A377G; K138Q; H461D; A377S; N62D and K371Q; V118L; and K124R; where numbering of the residues is relative to a wild-type Φ29 polymerase of SEQ ID NO: 3. The modified recombinant polymerase exhibiting an increased branching fraction can optionally exhibit increased exonuclease activity, where the polymerase exhibits an exonuclease rate that is about 10% to 50% as compared to its polymerization rate.

Modified recombinant polymerases of the compositions described above optionally exhibit a branching fraction that is at least 50% greater, at least 100% greater, or at least 200% greater than the branching fraction of a wild-type Φ29 polymerase of SEQ ID NO: 3. Optionally, the polymerases exhibit increased exonuclease activity as compared to the corresponding wild type polymerase, where the increased exonuclease activity is optionally about 10% to 50% as compared to its polymerization rate.

The modified recombinant polymerase exhibiting an altered translocation property can optionally comprise a fusion protein that comprises at least a subsequence of the parental polymerase (e.g., a Φ29 DNA polymerase) and at least one heterologous polypeptide sequence (see, e.g., SEQ ID No. 1 and SEQ ID No. 2 in the sequence listing herein). Optionally, the fusion of the at least a subsequence of the parental polymerase and the heterologous polypeptide sequence can occur at or near the c-terminal end of the parental polymerase. The wild-type polymerase is optionally a Φ29 polymerase. The heterologous polypeptide sequence can optionally comprise at least one charged amino acid, where the at least one charged amino acid can optionally be histidine or a chain of histidines. Optionally, the fusion proteins described above can comprise a linker between the at least a subsequence of the parental polymerase and the heterologous polypeptide sequence, where the linker optionally comprises a Ser3Gly linker.

The modified recombinant polymerase exhibiting an altered translocation property can optionally comprise at least one amino acid substitution or deletion or combination of substitutions or deletions selected from Asp570Lys; Asp570Ala; Asn313Lys; Asn313Ala; Gln303Lys; Gln303Ala; Gly532Ser; Met533delet; Cys530delet; Met533delet and Cys530delet; Gly532delet; Ala531Gly; Thr573Lys; Thr573Ala; Asn396Lys; Thr571Lys; Thr571Ala; Thr534Lys; Thr534Ala; Asp535Lys; Asp535Ala; Lys529Ala; and Lys529Asn; where numbering of the residue positions is relative to a wild-type Φ29 polymerase of SEQ ID NO: 3.

The altered translocation property of the modified recombinant DNA polymerases can optionally comprise a delay in translocation. Modified recombinant polymerases of the compositions described above can optionally exhibit a delay in translocation that is at least about 2.5×, 10× or 15× greater than a corresponding wild-type polymerase.

The modified recombinant polymerases of the compositions described above optionally exhibit an increased nucleotide or nucleotide analog residence time or increased processivity as compared to a corresponding wild-type polymerase.

The compositions comprising a modified recombinant polymerase that exhibits an altered property described above can include a phosphate-labeled nucleotide analog, a DNA template, and a modified recombinant DNA polymerase, e.g., any of the polymerases described above, that can incorporate the nucleotide analog into a copy nucleic acid in response to the DNA template. These compositions can be present in a DNA sequencing system, e.g., a zero-mode waveguide or nanohole. Optionally, the polymerase of the compositions can be immobilized on a surface.

In a related aspect, the invention provides methods of sequencing a nucleic acid template. The methods include providing a reaction mixture that includes the nucleic acid template, a replication initiating moiety that complexes with or is integral to the template, the modified recombinant nucleic acid polymerase of the compositions described above, where the polymerase is capable of replicating at least a portion of the template using the moiety in a template-dependent polymerization reaction, and one or more nucleotides and/or nucleotide analogs. In addition, the methods subject the reaction mixture to a polymerization reaction in which the modified recombinant polymerase replicates at least a portion of the template in a template-dependent manner, where one or more nucleotides and/or nucleotide analogs are incorporated into the resulting copy nucleic acid. The methods additionally identify a time sequence of incorporation of the one or more nucleotides and/or nucleotide analogs into the resulting copy nucleic acid. Optionally, the methods include a modified recombinant polymerase that exhibits increased processivity relative to the wild-type polymerase. The methods optionally include identifying the time sequence of incorporation by observing more than one signal pulse per nucleotide incorporation event. Subjecting the reaction mixture to a polymerization reaction and identifying a time of sequence incorporation can optionally be performed in a zero mode waveguide, nanohole or other micro- or nano-structure.

The invention also provides methods of making a nucleic acid that include providing a reaction mixture that comprises a template, a replication initiating moiety that complexes with or is integral to the template, a modified recombinant DNA polymerase with an altered property or combination of altered properties, e.g., such as those described above, which can replicate at least a portion of the template using the moiety in a template-dependent polymerase reaction, and one or more nucleotides and/or nucleotide analogs. In addition, the methods include reacting the mixture such that the polymerase replicates at least a portion of the template in a template-dependent manner, whereby the one or more nucleotides and/or nucleotide analogs are incorporated into the resulting nucleic acid. Optionally, the methods include detecting incorporation of at least one of the nucleotides and/or nucleotide analogs, which optionally includes observing more than one signal pulse per nucleotide incorporation event. The mixture is optionally reacted in a zero mode waveguide or nanohole, and the modified recombinant polymerase optionally exhibits an increased nucleotide or nucleotide analog residence time and/or processivity as compared to the parental polymerase.

In a related aspect, the invention provides methods of making a modified recombinant DNA polymerase that include mutating a polymerase of interest, e.g., a Φ29-type DNA polymerase, and selecting resulting modified polymerases for a property selected from increased branching fraction and altered translocation. Mutating the polymerase of interest can optionally comprise structurally modeling the polymerase to identify a feature that may affect branch fraction or altered translocation. Optionally, mutating the polymerase of interest includes making a library of modified recombinant polymerases, and selecting the modified polymerases includes screening the library to identify at least one member exhibiting the property. The polymerase of interest optionally includes a Φ29, B103, GA-1, PZA, Φ15, BS32, M2Y, Nf, G1, Cp-1, PRD1, PZE, SF5, Cp-5, Cp-7, PR4, PR5, PR722, L17, T4 or T7 polymerase. Modified recombinant polymerases that exhibit the property optionally exhibit increased nucleotide or nucleotide analog residence time, or increased processivity, as compared to a corresponding wild-type polymerase.

In some aspects the invention provides a method comprising: providing a polymerase enzyme complex comprising a template nucleic acid, a primer, and a polymerase enzyme under conditions wherein the interactions between a single polymerase and a labeled nucleotide analog can be monitored; exposing the polymerase enzyme complex to one or more labeled nucleotide analogs in solution under conditions wherein the nucleotide analogs are unincorporable; observing the transient binding of the one or more nucleotide analogs over time; and using the observed transient binding to provide information about the enzyme, template nucleic acid, primer, or nucleotide analog or analogs.

In some embodiments the primer is terminated, rendering the nucleotide analogs unincorporable. In some embodiments the method is carried out with a plurality of nucleotide analogs, and the transient binding over time is used to determine the effect of nucleotide structure on enzyme performance.

In some aspects, the invention provides a method for identifying a base in a template nucleic acid comprising: providing a polymerase enzyme complex comprising a template nucleic acid, a primer, and a polymerase enzyme; exposing the polymerase enzyme complex to one or more labeled nucleotide analogs in solution under conditions wherein the nucleotide analogs are unincorporatable, wherein one of the nucleotide analogs is a cognate nucleotide analog; detecting multiple transient binding events corresponding to the binding of a cognate nucleotide analog to the polymerase complex, thereby identifying the base corresponding to the cognate nucleotide analog in the template nucleic acid.

In some embodiments the polymerase enzyme complex comprises a single polymerase molecule. In some embodiments the polymerase enzyme complex is immobilized on a substrate. In some embodiments the polymerase enzyme complex is immobilized in an optical confinement.

In some embodiments at least a first and second primer are provided, wherein each of the primers are selected to bind to a known nucleotide sequence in which the identity of the base in the nucleotide sequence corresponding to the next cognate nucleotide is known and is different for the different primers; and wherein the polymerase enzyme complex is exposed to two or more unincorporatable nucleotide analogs, wherein the two or more unincorporable nucleotides comprise the cognate nucleotides for the two primers.

DETAILED DESCRIPTION

Figure 1:
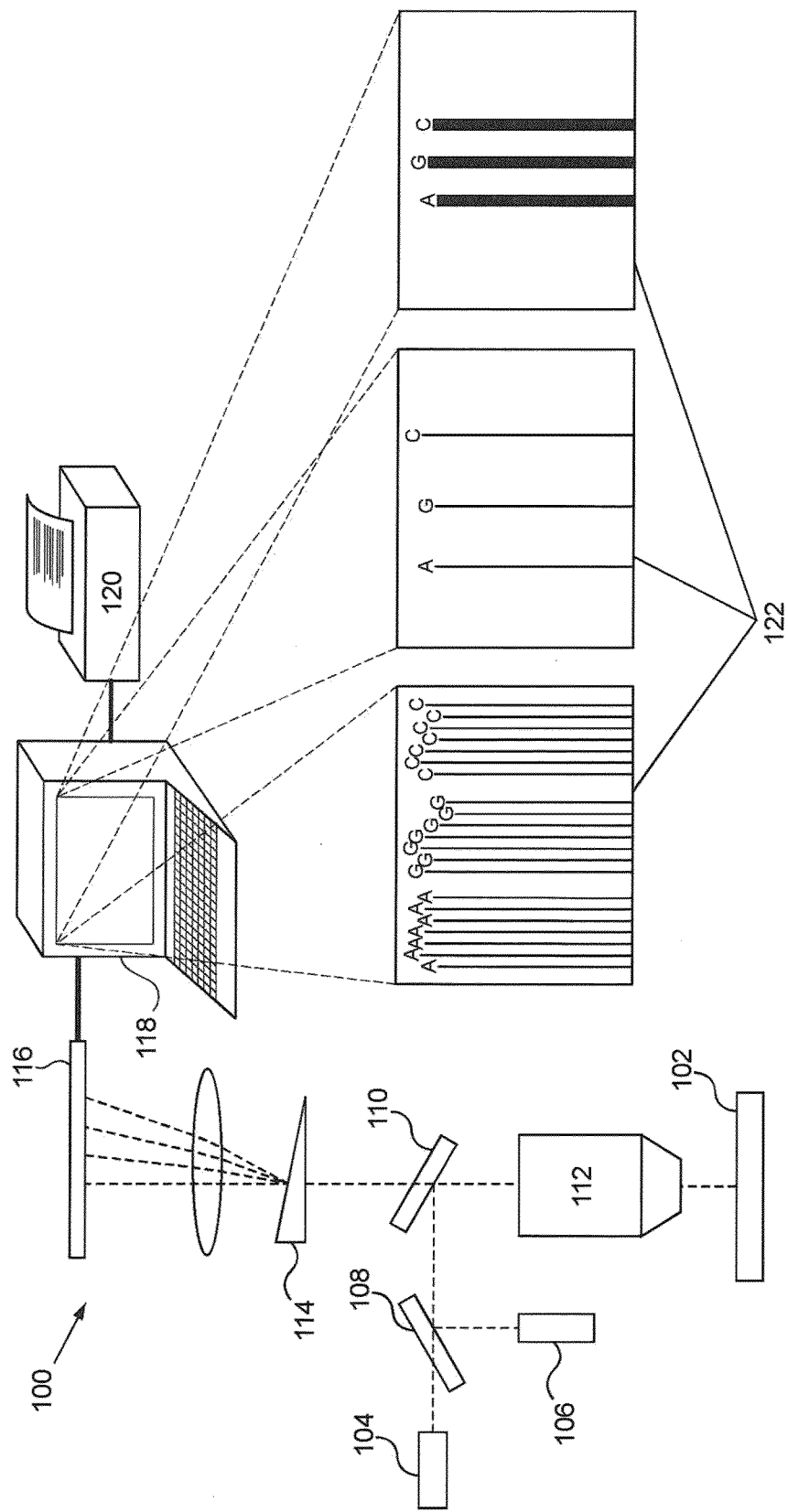
FIG. 1 schematically illustrates a system of the invention.

The invention is generally directed to methods and compositions for observing a single polymerase enzyme while it is sampling, but not incorporating, nucleotide substrates. The methods used can utilize the substrates and systems that have been developed for single molecule sequencing. In many cases, the same instruments and substrates used in these sequencing systems can be employed for observing the enzyme while it is sampling an unincorporable nucleotide. In preferred embodiments, the unincorporable nucleotide is labeled, e.g. with a fluorescent tag. The polymerase enzyme can be unlabeled and immobilized onto a surface, and the presence of the unincorporable nucleotide in the polymerase as it is sampling the active site can be observed in real time. In some cases, the polymerase is immobilized within an optical confinement such as a zero mode waveguide allowing for the observation of a very small volume of solution including the enzyme.

As has been described for single molecule sequencing with these systems, labeled nucleotides that spend time in the observation volume will be detected, while those that diffuse out of the observation volume will not. For real-time sequencing systems, it has been shown that the time spent in the observation volume by a labeled nucleotide that becomes incorporated will generally be longer that the time spent in the observation volume by a freely diffusing labeled nucleotide. This is because the polymerase enzyme tends to hold onto the nucleotide during the process leading to incorporation. This is described in more detail herein by reference to the kinetic cycle of the polymerase enzyme. We have found that even where a nucleotide or other related substrate is unincorporable, that the characteristics of the association of the substrate with the polymerase enzyme can be observed and that information about the behavior of the enzyme and about the substrate can be obtained by this observation.

While the above description highlights measuring the time that the labeled substrate spends in the observation volume in order to detect those substrates that are associated with the polymerase enzyme, there are also other ways of distinguishing such species. For example, the labeled substrate that is held in the active site can be less mobile than a freely diffusing label, allowing for detection on that basis. In addition, the active site of the enzyme can have different polarity, hydrogen bonding, ionic strength, or hydrophobicity/hydrophilicity characteristics that can lead to a different signal from a labeled substrate associated with an enzyme than one freely diffusing in solution. Association of labels, e.g. by FRET or quenching can also be used to detect the interaction, for example by having one member of a FRET pair on the substrate, and having the other member of a FRET pair on the polymerase or bound proximal to the polymerase can allow for a unique signal for labeled substrates that are interacting with the enzyme.

The monitoring the kinetics of the sampling of a substrate that does not get incorporated allows for measuring aspects of the enzyme kinetics, also allows for measuring aspects of the structure function relationship for various substrates, and allows for measuring the effect of structural changes on the template nucleic acid and even the primer. For example, the kinetics of sampling by cognate nucleotides is quite different than that of non-cognate nucleotides, for example in that the cognate nucleotides spend a much longer time associated with the enzyme than non-cognate nucleotides. By changing the structure of the substrate, starting with a cognate structure and adding functional groups that modify the structure, the effect of such changes on cognate binding kinetics can be measured, providing guidance on how the structural changes influence binding at the active site.

A substrate nucleotide or nucleotide analog can be made unincorporable in a variety of ways. In some cases, a fully functional enzyme, template, and primer is used, and the substrate analog is made unincorporable by a structural change, for example, a change that prevents formation of the phosphate bond. In some cases the enzyme, template, or primer are modified such that incorporation and nascent nucleic acid formation is blocked. For example, in some cases a terminating group is added which prevents the nascent strand from further extension. In some cases, the conditions are modified in order to make the substrate unincorporable, for example by changes in the pH, ionic strength, or level and type of specific ions. For example, catalytic metal ions including Mn or Mg can be removed or sequestered, for example by a chelating agent. The nucleotide can also be rendered unincorporable in some cases by the addition of non-catalytic metals such as Sr, Zn, or Ca. In some cases, combinations of the above can be used to result in non-incorporation. The type of information that is obtained will generally depend on how the substrate is made unincorporable. For example, mutations in the polymerase can be made to change its kinetics, and the effects of the changes can provide information on how the enzyme will behave catalytically. Changes can be made to the enzyme that will affect the rate of one or more of the kinetic steps shown in FIG. 6. Monitoring the sampling of unincorporable nucleotides of these modified enzymes can assist in the development of enzymes having the desired rates for the various steps in the process.

The invention also describes modified or engineered compositions that are characterized by modified profiles or characteristics for incorporation of nucleotides in template directed nucleic acid synthesis. Such characteristics include, for example, increased frequency of branching events, changes in reaction rates that lead, e.g., to delayed polymerase translocation and/or increased nucleotide or nucleotide analog retention time during polymerization reactions. Individually or in combination, these modifications can increase sequence readout accuracy (e.g., increase sequence accuracy in single molecule sequencing reactions) using the methods of the invention. Polymerases of the invention optionally also include additional mutations or modifications that provide other desirable features, e.g., modify one or more kinetic features of the polymerase (e.g., increased processivity), increased surface stability for polymerases bound to a surface, or the like.

During sequencing by incorporation, e.g., single molecule sequencing by synthesis (SMS), nucleotide (or nucleotide analog) incorporation events are detected in real-time as the bases are incorporated into the extension product. This can be accomplished by immobilizing a synthesis complex, which includes a polymerase enzyme, such as a DNA polymerase enzyme, a template nucleic acid sequence, and a primer sequence that is complementary to a portion of the template sequence, within an optically confined space or otherwise resolved as an individual molecular complex. Some SMS methods employ nucleotide analogs that include fluorescent labels coupled to the polyphosphate chain of the analog, which are then exposed to the complex. Upon incorporation, the nucleotide—along with its fluorescent label—is retained by the complex for a time and in a manner that permits the detection by a sequencing system of a signal "pulse" from the fluorescent label at the incorporation site. The sequentially detected signal pulses are then interpreted by the sequencing system to generate a readout corresponding to the sequence of the template nucleic acid. For a discussion of preferred sequence by incorporation processes, see, e.g., U.S. Pat. Nos. 6,056,661, 7,052,847, 7,033,764, 7,056,676, 7,361,466, the full disclosures of which are hereby incorporated herein by reference in their entirety for all purposes. Further details regarding base calling during sequencing by incorporation methods are found in Tomaney et al. PCT Application Serial No. PCT/US2008/065996 METHODS AND PROCESSES FOR CALLING BASES IN SEQUENCING BY INCORPORATION METHODS, incorporated herein by reference in its entirety for all purposes.

Figures 2A, 2B:
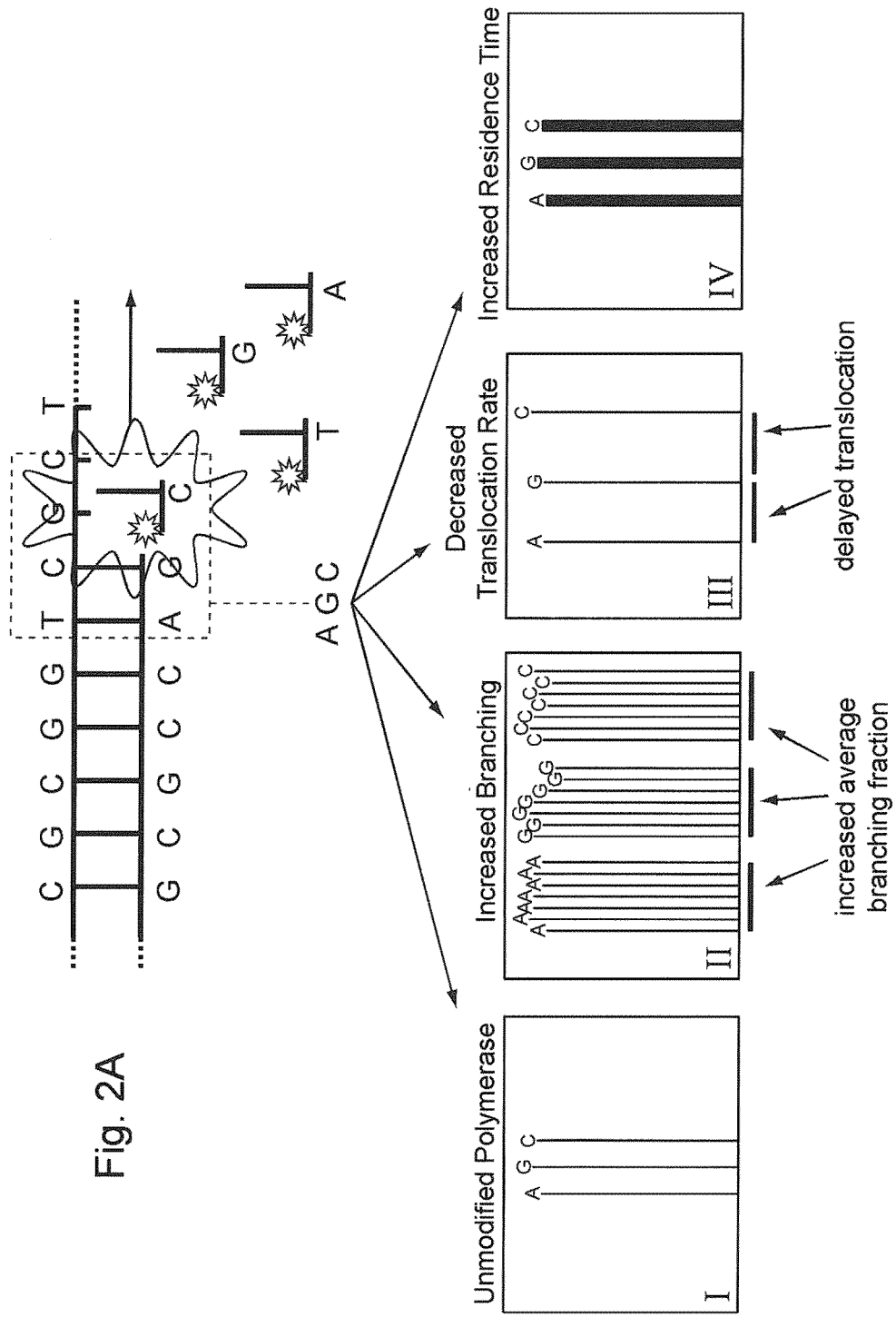
FIG. 2 schematically illustrates a sequencing by incorporation reaction and the resulting characteristics of signal pulses detected by a system that employs reaction conditions or polymerases of the invention.

FIG. 2 schematically illustrates a sequencing by incorporation reaction and the resulting patterns of signal pulses detected by a system that employs reaction conditions or polymerases of the invention. FIG. 2A schematically illustrates a polymerization reaction where dye-labeled nucleotides are incorporated in a stepwise fashion according to the sequence of the template strand. When a dye-labeled nucleotide enters the detection region (dashed box) which encompasses the polymerase, the dye emits optical signal pulses or signatures in response to excitation radiation that are detected by a signal detector. Examples of detection methods and optically confined reaction regions include, e.g., Zero Mode Waveguides, e.g., as described in U.S. Pat. Nos. 6,917,726, 7,013,054, 7,181,122, and 7,292,742, the full disclosures of which are hereby incorporated by reference in their entirety for all purposes. FIG. 2B schematically illustrates the patterns or characteristics of signal pulses that would arise under standard conditions (Panel I), increased branching conditions (Panel II), conditions that include a polymerase with a decreased translocation rate (Panel III) and conditions that include a polymerase that exhibits increased nucleotide analog residence time (Panel IV). The resulting patterns or characteristics of signal pulses from the various conditions are described in detail below.

I. Increased Branching

"Branching" is a phenomenon that occurs during polymerization. During a polymerase kinetic cycle, sampling of each of four possible nucleotides (or nucleotide analogs) occurs until a correct Watson-Crick pairing is generated (see, e.g., Hanzel et al. WO 2007/076057 POLYMERASES FOR NUCLEOTIDE ANALOG INCORPORATION for an example model description of the kinetic cycle of a polymerase). However, chemical linkages between a sampled nucleotide and a 3'OH group of a preceding base can fail to occur for a correctly paired nucleotide, due, e.g., to release of the correctly paired base from the active site. This can occur as a result of the nucleotide leaving the site without a covalent bond being formed, or e.g., as a result of cleavage of the covalent bond (e.g., due to exonuclease activity) prior to polymerase translocation to the next incorporation site. During single molecule sequencing (SMS) procedures, and particularly those single molecule processes that monitor incorporation in real time, where both the failed incorporation and the actual incorporation of the nucleotides provide signal pulses, sequences deciphered for the incorporation site can have an incorrect "insertion" relative to the correct sequence as a result of such branching. This phenomenon is termed "branching" because it leads to a branch in the sequence (a site where two identical molecules will be read as having different sequences) and may lead to increased error rates during SMS.

While branching can, in many applications of single molecule sequencing processes, be viewed as an accuracy reducing phenomenon, in at least a first aspect of the present invention, increased branching is exploited to increase sequence accuracy by providing redundant signal events resulting from iterative sampling of labeled nucleotides or nucleotide analogs. In particular, improved sequence reliability and accuracy is achieved by providing reaction conditions and/or polymerases that exhibit a relatively high average branching fraction for a particular nucleotide or nucleotide analog and a certain distribution of branch signal pulses around this average. Such compositions are used in combination with a sequencing system that observes and interprets more than one signal pulse or signature per incorporation event to identify the nucleotide sequence of a target or template nucleic acid. This is advantageous in the present invention because detecting more than one signal pulse or signature per incorporation event provides inherent redundancy of signal for each desired incorporation event. In some cases, the "signature" will include regions of optical signal versus time that are characteristic of the branching nucleotide, but do not appear as individual pulses. This can occur, for example, when a sequence of pulses are not individually resolved. Further details regarding sequencing under high branch fraction conditions can be found in Bjornson et al. PCT Application Serial No. PCT/US2009/000921 COMPOSITIONS AND METHODS FOR USE IN ANALYTICAL REACTIONS, incorporated herein by reference in its entirety for all purposes. Additional information useful to sequencing under high branch fraction conditions can be found in Bjornson et al. PCT Application Serial Number PCT/US2009/002003 TWO SLOW-STEP POLYMERASE ENZYME SYSTEMS AND METHODS, incorporated herein by reference in its entirety for all purposes.

The branching fraction is the proportion of cognate nucleotide (or nucleotide analog, e.g., A488dA4P) dissociation events from the polymerase active site as compared to the total number of events, e.g., the sum of the dissociation events and the incorporation events for the cognate nucleotide or nucleotide analog. The present invention provides high branch fraction polymerization reactions. As used herein, a high branch fraction polymerization reaction includes a reaction that exhibits a branching fraction of at least about 70% or more, about 80% or more, about 85% or more, about 90% or more, or about 95% or more. For example, in a sequencing reaction in which the branching fraction is 80%, 80% of the total interactions of the nucleotide or nucleotide analog with the polymerase binding pocket result in dissociation, rather than incorporation, of the nucleotide or nucleotide analog.

An aspect of the invention is a method of nucleic acid sequencing by monitoring an optical signal from a polymerase reaction, wherein the base call, or the assignment of the incorporated base is made on the basis of multiple pulses from the same nucleotide. The number of pulses used to assign which base has been incorporated may depend on the branching fraction under the conditions of the polymerase reaction. In some cases, the number of pulses used to assign which nucleotide has been incorporated will vary between the different nucleotides in that reaction medium. The number of pulses used to assign which nucleotide is incorporated can be about 2, 3, 4, 5, 6, 7, 8, 9, 10, 12, 15, 20, 30, or more pulses. The number of pulses can be between about 2 and about 30 pulses, between about 2 and about 20 pulses, or between about 3 and about 25 pulses. The number of pulses can be expressed, for example, as the average number of pulses used to assign a given nucleotide for one sequencing reaction.

Sequence read errors during SMS can also derive from the incorporation of nucleotides or nucleotide analogs that constitute dark matter (for the purposes of this disclosure, "dark matter" refers to unlabeled nucleotides or nucleotide analogs with nonfunctional labels, e.g., broken fluorophores). Here, a genuine incorporation event is not detected due to the absence of a signal pulse from the dark matter, and a subsequent incorporation event is interpreted by the sequencing system as occurring at the position where the dark matter was incorporated. Dark matter, therefore, may potentially contribute to error rates in single molecule sequencing that utilizes the incorporation of labeled nucleotides.

Figure 3:
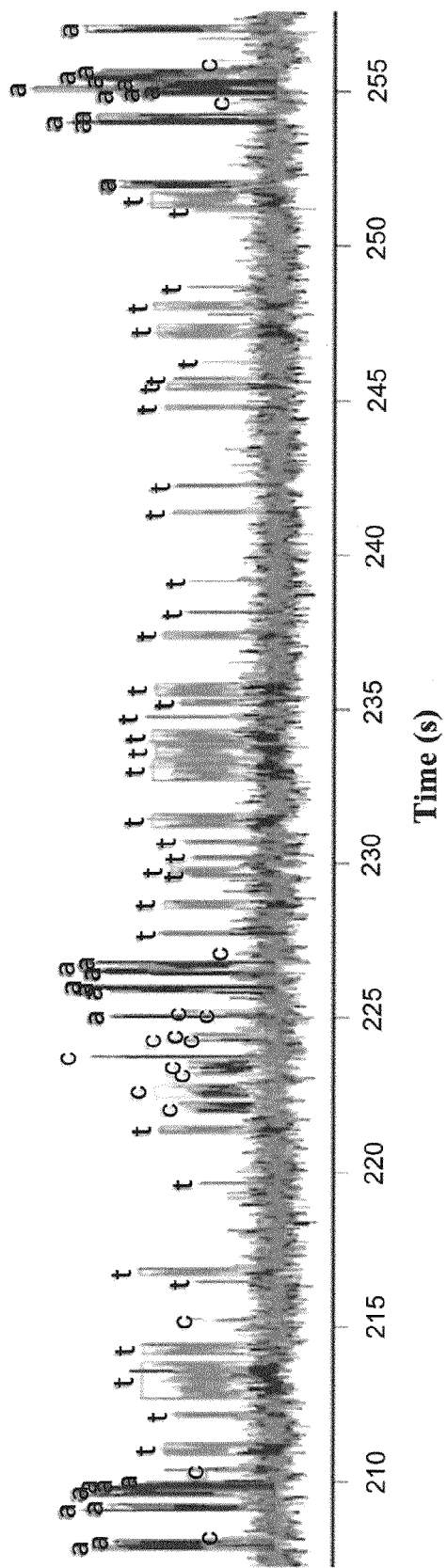
FIG. 3 is a time sequence of signal pulses generated from a sequencing by incorporation reaction under relatively high branch fraction conditions.

In certain aspects, the reaction conditions, modified recombinant polymerases, and/or nucleotide analogs of the present invention—employed in conjunction with the sequencing system of the present invention—reduce sequence read errors that might result from missed pulses. The reaction conditions induce a relatively high branch fraction polymerization reaction—and the modified recombinant polymerases exhibit increased average branching fractions—such that a greater number of nucleotide analogs, which, if incorporated, would correctly pair with the corresponding nucleotide of the template strand, enter the active site before an analog is eventually incorporated into the extension product. The nucleotide analogs that enter the active site, but fail to incorporate, produce redundant signal pulses or signatures at each incorporation site, resulting in multiple redundant signal events for each incorporation event. An example of signal pulses generated under relatively high branch fraction conditions is shown in FIG. 3.

The sequencing system takes into account the average branching fraction of the polymerase and a certain distribution of branch pulses or signatures per nucleotide incorporation around this average. Because multiple signal pulses are observed for each incorporation event, branching events involving unlabeled nucleotides or nucleotides with nonfunctional labels, i.e., dark matter, do not result in a sequencing read error, but rather only slightly decrease the distribution of the average number of pulses or signatures per incorporation. In the event that dark matter is incorporated into the extension product, signal pulses derived from branching events involving nucleotide analogs with functional labels prior to dark matter incorporation can provide sufficient redundancy for determining the correct base at the incorporation site.

As will be appreciated, high branch fraction sequencing conditions can also be used for sequencing RNA templates, for example using reverse transcriptase enzymes and for RNA synthesis, for example by DNA dependent RNA polymerases.

A. Enhanced Sequencing Using Reaction Conditions that Promote Branching

The present invention provides reaction conditions—such as the type, level, and relative amounts of cofactors—that increase the frequency of branching events during nucleic acid polymerization reactions. Such reaction conditions may be used in combination with polymerases that are engineered to exhibit increased branching fractions under selected conditions, or can be used with polymerases that are unaltered with respect to branching properties. The phosphoryl transfer reaction of DNA polymerases is typically catalyzed by a two-metal ion mechanism, where two divalent metal ions, e.g., $Me^{++}$ and/or $Mn^{++}$, complexed with the DNA polymerase facilitate the incorporation of a nucleotide into the 3'OH of the extension product. One of the metal ions is proposed to interact with the 3'OH of the primer strand, thereby facilitating its attack on the α-phosphate of the incoming nucleotide. Both metal ions are believed to stabilize the transition state that occurs during the course of the extension reaction.

During the course of the polymerase reaction, divalent metal cofactors, such as magnesium or manganese, will interact with the enzyme-substrate complex, playing a structural role in the definition of the active site. For a discussion of metal cofactor interaction in polymerase reactions, see, e.g., Arndt, et al., Biochemistry (2001) 40:5368-5375. For example, and without being bound to any particular theory of operation, it is understood that metal cofactor binding in and around the active site serves to stabilize binding of incoming nucleotides. For further details regarding the effect of metal cofactors on polymerase kinetics and nucleic acid synthesis reactions, see Bjornson et al. PCT Application Serial Number PCT/US2009/002003 TWO SLOW-STEP POLYMERASE ENZYME SYSTEMS AND METHODS, incorporated herein by reference in its entirety for all purposes.

In the context of the present invention, it has been discovered that modulation of the concentration of a divalent metal cofactor, or competitive modulation of two or more divalent metal cofactors, to the synthesis reaction can result in increased branching for enhanced nucleic acid sequencing without a consequent increase in negative reaction events. As described in detail herein, the increased branching provides redundant signal pulses or signatures, thereby reducing or eliminating the occurrence of missed signal pulses and improving sequence accuracy. As used herein, a signature can include regions of optical signal versus time that is characteristic of the branching nucleotide, but does not appear as an individual signal pulse.

In the synthesis reaction, certain divalent or trivalent metal cofactors, such as magnesium and manganese are known to interact with the polymerase to modulate the progress of the reaction (See, e.g., U.S. Pat. No. 5,409,811). As will be appreciated, depending upon the nature of the polymerization reaction, environmental conditions (e.g., temperature, pH, etc.), the polymerase used, the nucleotides employed, etc., different metal co-factors will have widely varying catalytic effects upon the polymerization reaction. In the context of the present invention, different metal cofactors will be referred to herein based upon their relative catalytic impact on the polymerization reaction, as compared to a different metal included under the same reaction conditions. For purposes of discussion, a first metal cofactor that interacts with the polymerase complex to support the polymerization reaction to a higher level than a second metal cofactor under the same conditions is termed a "catalytic metal ion" or "catalytic metal."

The present invention provides sequencing compositions and methods that include, e.g., divalent metal ions at concentrations that induce high branch fraction polymerization reactions. Divalent metal ions of the invention can be, e.g., $Mg^{++}$, $Mn^{++}$, $Zn^{++}$, $Co^{++}$, $Ca^{++}$, $Fe^{++}$, $Cr^{++}$, and/or $Sr^{++}$. For the purposes of this disclosure, a high branch fraction polymerization reaction includes a reaction that exhibits a branching fraction of about 70% or more, about 80% or more, about 85% or more, about 90% or more, or about 95% or more.

In one embodiment, a high branch fraction polymerization reaction is induced in a sequencing composition that includes a DNA polymerase, e.g., a Φ29-derived polymerase that uses $Mn^{++}$ as the sole source of metal cofactor at a concentration of about 250 μM or less, about 200 μM or less, about 150 μM or less, about 125 μM or less, about 100 μM or less, about 75 μM or less, or about 50 μM or less. By contrast, branching is typically not promoted in sequencing compositions that include, e.g., about 500 μM $Mn^{++}$ or more, in the absence of other factors.

In another embodiment, a high branch fraction polymerization reaction is induced by a sequencing composition that includes a DNA polymerase, e.g., a Φ29-derived polymerase that uses $Mg^{++}$ as the sole of metal cofactor at a concentration of about 1 mM or more, about 2 mM or more, about 3 mM or more, about 5 mM or more, about 10 mM or more, about 20 mM or more, about 30 mM or more, about 40 mM or more, or about 50 mM or more.

In yet another embodiment, a high branch fraction polymerization reaction is induced by a sequencing composition that includes a DNA polymerase, e.g., a Φ29-derived polymerase that uses both $Mg^{++}$ and $Mn^{++}$ as metal cofactors, where both the absolute values and ratio of the two concentrations of $Mg^{++}$ and $Mn^{++}$ determines the extent of branching. For example, the present invention provides sequencing compositions that induce branching by including both $Mg^{++}$ and $Mn^{++}$, where the concentration of $Mg^{++}$ is greater than the concentration of $Mn^{++}$. In one particular embodiment, the sequencing composition includes about 10 mM $MgCl_2$ and about 100 µM $MnCl_2$. A range of suitable concentrations to increase branching are 0-200 mM $MgCl_2$ and 0.01-50 mM $MnCl_2$, and all possible combinations of values between those two ranges.

In another embodiment, the reaction conditions include $Mn^{++}$ and a metal cofactor other than $Me^{++}$, such as calcium, barium, strontium, iron, cobalt, nickel, tin, zinc, and europium. For example, these metals can be added to the polymerization reaction in salt form such as $Sr(OAc)_2$, $CoCl_2$, $SnCl_2$, $CaCl_2$, or $ZnSO_4$. Both the absolute values and ratio of the two concentrations can influence the extent of branching.

The present invention also provides methods for increasing the branching fraction during sequencing by incorporation by modifying reaction conditions other than the identity and/or concentrations of metal ions. For example, the pH (lowering the pH to about 6.5), temperature (e.g., decreased temperature), addition of $D_2O$, and/or addition of small molecule inhibitors (e.g., a noncompetitive inhibitor that slows covalent attachment of the nucleotide to the 3-OH of the growing strand of the nucleic acid being synthesized, e.g., a noncompetitive HIV-RT inhibitor), can be used to alter the branching fraction of the polymerization reaction.

As will be appreciated, the sequencing compositions and methods described above that utilize metal cofactors to induce relatively high branching fractions can be used in combination with any other embodiments described herein, including: (1) modified recombinant polymerases that exhibit increased branching fractions as compared to the corresponding wild-type polymerases; (2) iterative sampling of unincorporatable nucleotides; (3) two slow-step enzyme systems; (4) detection of noncognate branching events; (5) modified recombinant polymerases that exhibit altered translocation properties as compared to the corresponding wild-type polymerases; (6) modified recombinant polymerases that exhibit increased nucleotide residence time; (7) sequencing of nucleic acid templates using more than one mode; and/or (8) any other combination of embodiments described herein. As will also be appreciated, high branch fraction sequencing conditions can be used for sequencing RNA templates, for example using reverse transcriptase enzymes, and for RNA synthesis, for example by DNA dependent RNA polymerases.

B. Enhanced Sequencing Using Modified Recombinant Polymerases with Increased Branching Fractions During a polymerase kinetic cycle, sampling of each of the possible nucleotides or nucleotide analogs occurs until a correct Watson-Crick pairing is generated. According to structural studies of DNA polymerases complexed with DNA substrates, the primer-terminus does not typically form a covalent bond with an incorrectly paired nucleotide (Berman, et al. (2007) "Structures of phi29 polymerase complexed with substrate: the mechanism of translocation in polymerases." *EMBO J* 26: 3494-3505). Conversely, branching events can occur during the polymerase kinetic cycle, where chemical linkages between a correctly paired nucleotide and a 3'OH of a preceding base fail to form, e.g., due to premature release of the sampled nucleotide from the active site. The kinetic cycle is then repeated for the same site, eventually resulting in the physical incorporation of the correct nucleotide.

As described above, these branching events can result in sequence read errors in standard sequencing methods, e.g., due to extra incorporation signals relative to the template sequence, received by a sequencing system that monitors signal pulses from the nucleotide analog at the active site as a proxy for incorporation, if the system does not account for the branching events. However, a sequencing system that utilizes branching events and calls bases according to multiple signal pulses or signatures for each incorporation event can be used in combination with polymerases that exhibit a high average branch fraction to improve sequence read accuracy. Under such conditions, redundant signals pulses or signatures resulting from iterative sampling of a labeled cognate nucleotide or nucleotide analog can reduce the error rate of a sequence read, as compared to lower branch fraction sequencing conditions where only one or a small number of signal pulses for each incorporation event can go undetected by the sequencing system.

The present invention provides modified recombinant polymerases and reaction conditions with increased branching fractions that can be used to improve sequence read accuracy. The branching fraction is the proportion of cognate nucleotide (or nucleotide analog, e.g., A488dA4P) dissociation events from the polymerase active site as compared to the total number of events, e.g., the sum of the incorporation events and dissociation events for the cognate nucleotide or nucleotide analog. Either incorporation or non-incorporation events, or both, can be detected by monitoring a signal profile produced by a sequencing reaction.

In the present invention, modification of a DNA polymerase by mutagenesis is used to increase the frequency of branching events. In exemplary embodiments, this modification may include one or more of either creating a more loosely structured binding pocket for the (typically non-natural) nucleotides that are incorporated during SMS, or by structurally modifying the polymerase to increase exonuclease activity. Random mutation strategies can also be used, e.g., in conjunction with appropriate screening steps to select libraries of mutants for increased branching (or other properties of interest). Combinations of random and site-directed mutagenesis can also be used, typically in conjunction with selection of mutant libraries for a property of interest.

As will be appreciated, polymerase enzymes of the present invention are not limited to DNA polymerases. The present invention provides modified recombinant reverse transcriptase enzymes and modified recombinant DNA-dependent RNA polymerases, which can exhibit increased branching fractions during RNA template sequencing and RNA synthesis, respectively.

One class of example mutants described in this application were designed to address branching fraction by modifying various sites in, e.g., a Φ29 polymerase, predominantly in and around the binding pocket, to create weaker polymerase-analog interactions during an extension (polymerization) reaction. A second class of example mutants described in this application were designed to increase branching by modifying various sites in, e.g., a Φ29 polymerase, predominantly in and around the exonuclease domain in order to increase the exonuclease rate of the polymerase to about 10% to 50% as compared to its polymerization rate. As noted, the "branching fraction" is the proportion of cognate nucleotide (or nucleotide analog, e.g., a dye-labeled analog) dissociation events from the polymerase active site to the total number of events, e.g., the sum of the incorporation events and dissociation events. For the purposes of this disclosure, dissociation events also include cleavage of an incorporated nucleotide as a result of exonuclease activity. These mutational features, i.e., increased branching by creating a more loosely structured binding pocket or increasing exonuclease activity, can be provided in combination.

Desirably, the branching fraction for a polymerase for a given nucleotide of interest (e.g., a labeled nucleotide analog) can be more than 50%, more preferably more than 60%, yet more preferably more than 70%, and still more preferably more than 80% or more of the total interactions, e.g., dissociation events and association events, of the nucleotide analog with the polymerase binding pocket. In comparison, a parental Φ29 polymerase exhibits a branching fraction of approximately 23% for, e.g., a thymine nucleotide analog that includes an Alexa568 fluorophore (Invitrogen Inc., Carlsbad, Calif.) linked to the terminal phosphate of a hexaphosphate chain, also referred to as A568dT6P, wherein approximately 23% of the total events with a gamma-linked A568dT6P nucleotide analog in the polymerase binding pocket are dissociation events.

The invention provides methods for generating recombinant polymerases that comprise modifications that increase the frequency of branching, which can be useful in any number of applications where accuracy of polymerization is beneficial, e.g., high-throughput sequencing systems, e.g., in a nanohole (an aperture of less than 1 μM diameter through which a synthesis complex can be illuminated by optical energy or monitored electrochemically) or specialized nanoholes such as zero-mode waveguides (ZMW), SNP genotyping using single base extension methods, real time monitoring of amplification, e.g., RT-PCR methods, and the like. Also provided by the invention are compositions that include such polymerases and methods in which these polymerases can be useful in, e.g., sequencing or making DNA.

In some embodiments, the compositions can also include nucleotide analogs, and preferably, optically labeled, e.g., fluorescently labeled, nucleotide analogs. In particularly preferred aspects, the compositions will include one or more types of phosphate-labeled nucleotide analog or analogs, e.g., a nucleotide analog comprising from 3-7 phosphate groups which in preferred cases may include a fluorophore coupled to the phosphate chain that is released upon incorporation, which can be incorporated into a copy nucleic acid by the modified polymerase in response to a DNA template. In some embodiments, the compositions can be present in a sequencing system, e.g. in a nanohole or specialized nanohole such as a zero-mode waveguide, where a polymerase of the invention can optionally be immobilized on a surface.

Modification of a polymerase, e.g., any of the polymerases described herein, or polymerases homologous to those described herein, by any one or more the strategies described herein can increase the frequency of branching events by creating a more loosely structured binding pocket for non-native nucleotides. The modified polymerases can comprise at least one amino acid substitution or a combination of amino acid substitutions relative to the parental polymerase.

Polymerases of the invention can be described or analyzed based upon comparison to a reference (e.g., parental) polymerase. For example, a parental polymerase (e.g., a wild type polymerase from which the polymerase of the invention is derived, or an available mutant) can serve as a reference polymerase. Comparisons between a reference polymerase and a polymerase of the invention are performed under selected reaction conditions. In general, standard reaction conditions can be defined based on the usual reaction conditions (e.g., optimized for the reaction at issue) for a given parental (e.g., wild-type) polymerase. That is, the reaction condition preferences for many polymerases are known; the appropriate adaptations of these conditions to specific applications such as SMS are known or can be determined through routine optimization or reaction conditions, and these "application optimized" reaction conditions can be used for comparison of the polymerase of the invention to the reference polymerase. For example, reaction conditions can be optimized for a reference polymerase such as a Φ29 polymerase, e.g., in an SMS application, with the reaction conditions being selected for optimal processivity, optimal fidelity, increased or decreased branch fraction, or a combination thereof, with that reference polymerase being used in a comparison to a polymerase of the invention under the optimized conditions. For example, in one SMS application, the reaction conditions can include those described above, and comparison to the polymerase of the invention can be conducted by performing a comparative assay, using the methods herein.

A number of specific examples of modified polymerases, e.g. modified to increase the average branching fraction, are described herein. The binding pocket is a portion of the polymerase that encompasses the nucleotide binding site and analog base during the pairing of a nucleotide analog with a template DNA. Because of the physical proximity of the binding pocket to the incoming nucleotide or nucleotide analog, mutations to this region can affect the branching fraction. However, mutations that increase the branching fraction are not limited to this area of the polymerase. For example, relative to a parental or wild-type Φ29 DNA polymerase, useful modifications can include any of the following mutations: N62D and Y454A; D362S; Y259H; F237Y; L381I; Y369H; H461Y; A377G; K138Q; H461D; A377S; N62D and K371Q; V118L; and K124R. For the purposes of this disclosure, a parental polymerase includes a wild-type or available mutant/recombinant polymerase which is additionally altered to produce the desired properties of the invention, e.g., increased branching, delayed translocation or increased nucleotide analog residence time. A list of specific useful Φ29 mutants and their branching fractions (% BF) and corresponding increases in branching fraction (% increase BF) for a particular 6P nucleotide analog relative to a reference Φ29 polymerase (N62D) is provided in Table A below.

TABLE A

| Mutation(s) | % BF | % Increase BF | % BF | % Increase BF |
|---|---|---|---|---|
| | A568dT6P | | A647dG6P | |
| N62D | 23 | — | 38 | — |
| N62D_Y454A | 30 | 30 | 48 | 25 |
| D362S | 31 | 34 | 46 | 20 |
| Y259H | 33 | 44 | 52 | 37 |
| F237Y | 35 | 53 | 46 | 21 |
| L381I | 37 | 60 | 47 | 22 |
| Y369H | 40 | 75 | 55 | 43 |
| H461Y | 43 | 86 | 57 | 49 |
| A377G | 44 | 90 | 75 | 97 |
| K138Q | 45 | 96 | 61 | 59 |
| H461D | 46 | 102 | 62 | 62 |
| A377S | 61 | 167 | 70 | 84 |
| N62D_K371Q | 62 | 172 | 94 | 145 |
| V118L | 65 | 181 | 74 | 92 |
| K124R | 73 | 216 | 84 | 119 |
| | A555dC6P | | A660dA6P | |
| N62D | 27 | — | 22 | — |
| N62D_Y454A | 38 | 42 | 23 | 3 |
| D362S | 39 | 45 | 26 | 20 |

19

TABLE A-continued

| Mutation(s) | A555dC6P | | A660dA6P | |
|---|---|---|---|---|
| | % BF | % Increase BF | % BF | % Increase BF |
| Y259H | 39 | 44 | 25 | 11 |
| F237Y | 41 | 52 | 25 | 11 |
| L381I | 37 | 36 | 26 | 18 |
| Y369H | 43 | 59 | 28 | 27 |
| H461Y | 50 | 86 | 31 | 42 |
| A377G | 37 | 36 | 32 | 47 |
| K138Q | 48 | 78 | 27 | 21 |
| H461D | 51 | 91 | 31 | 39 |
| A377S | 72 | 168 | 56 | 152 |
| N62D_K371Q | 87 | 224 | 82 | 272 |
| V118L | 68 | 154 | 47 | 114 |
| K124R | 79 | 195 | 63 | 183 |

As noted, the branching fraction, e.g., % branching, is a relative measure of the number of times a correctly paired base, e.g., a Watson-Crick paired base, leaves the active site of the polymerase without forming a phosphodiester bond with the 3'OH of the primer-terminus relative to the total number of interactions that occur between a nucleotide (or nucleotide analog) and the binding pocket of the polymerase, e.g., the total number of opportunities the nucleotide or nucleotide analog has to correctly pair and incorporate. Additionally, for the purposes of this disclosure, branching refers to cleavage and dissociation from the polymerase active site of an incorporated nucleotide as a result of exonuclease activity. Branching is expressed as a percentage of the dissociation events vs. the total sum events, e.g., dissociation and association events. For example, for a polymerase harboring the Y369H mutation, for every 100 times an A568dT6P analog (i.e., a thymidine hexaphosphate nucleotide in which the terminal phosphate is labeled with an Alexa568 dye) interacts with the binding pocket of this polymerase, 40 of the events are non-productive dissociation events, e.g., wherein the analog dissociates from the polymerase instead of participating in a polymerization reaction. For this polymerase, the percent increase in branching fraction is 75% as compared to a reference phi29 polymerase (N62D) under identical reaction conditions.

The branching fraction can be measured by loading a polymerase active site with a cognate-matching nucleotide analog that can bind in the +1 and +2 positions. In the absence of divalent cation, this nucleotide cannot be incorporated into the DNA strand, so will pair with the template nucleotide at the +1 position but be released at some frequency specific for that analog/polymerase combination, e.g., the branching rate. This loading reaction is then followed by addition of a divalent cation that supports extension, e.g., $Mn^{2+}$, and a terminating-type nucleotide analog, e.g., a dideoxynucleotide, comprising the same base as the cognate-matching analog in the loading step.

The dideoxy-analog will be incorporated into any +1 sites that are unoccupied and, once added, preclude further extension. Hence, polymerase active sites that are already occupied by a paired analog base extend to the +2 position, those that are not occupied (i.e. "branched") incorporate the dideoxy-type analog at +1 and do not extend, resulting in a single base addition. The extension products of this reaction are visualized by standard separation methods, e.g., gel or capillary electrophoresis, and the ratio of terminated product that is generated when a dideoxynucleotide is incorporated at the +1 position divided by the total terminated product, e.g., when a dideoxynucleotide is incorporated at both the +1 and +2 positions, indicates the fraction of 'branched' events that occur.

20

The branching fraction exhibited by modified polymerases of the present invention, e.g., a modified Φ29 polymerase, can be greater than a branching fraction exhibited by the corresponding wild-type polymerase for a given nucleotide analog. For example, a modified recombinant polymerase of the invention can exhibit an increased branching fraction that is greater than about 20% for the phosphate-labeled analog, greater than 50% for the phosphate-labeled analog, greater than 75% for the phosphate-labeled analog, greater than 100% for the phosphate-labeled analog, greater than 150% for the phosphate-labeled analog, or greater than 200% for the phosphate-labeled analog, as compared to the corresponding wild-type polymerase, e.g., a wild-type Φ29 polymerase, under the standard reaction conditions described above.

In some embodiments, the modified polymerase that exhibits an increased frequency of branching can also exhibit a $K_m$ for a given phosphate-labeled nucleotide analog, e.g., any of the phosphate-labeled nucleotide analogs described herein, that is useful to achieve increased branching. For enzymes obeying simple Michaelis-Menten kinetics, kinetic parameters are readily derived from rates of catalysis measured at different substrate concentrations. The Michaelis-Menten equation, $V=V_{max}[S]([S]+K_m)^{-1}$ relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V). To determine a $K_m$ for a particular analog a series of extension reactions are performed with a varying concentration of the analog of interest with a fixed, saturating concentration of native nucleotides. A fit of the rate versus the substrate concentration generates estimation of the $-K_m$ as the slope of this line.

The present invention also provides polymerases with increased exonuclease activity for increasing the branching fraction during a template-dependent polymerization reaction, e.g., SMS. In a preferred aspect, a polymerases of the invention exhibits an exonuclease rate that is between about 10% and 50% as compared to its polymerization rate.

As will be appreciated that the above-identified modified or recombinant polymerases that display increased branching fractions may optionally include additional modifications that confer other useful properties described herein, e.g., delayed translocation, increased nucleotide analog residence time and/or increased processivity. As will also be appreciated, the above-identified modified or recombinant polymerases that display increased branching fractions can be used in combination with any other embodiments described herein, including: (1) reaction conditions that increase the frequency of branching fraction nonincorporation events; (2) iterative sampling of unincorporatable nucleotides; (3) two slow-step enzyme systems; (4) detection of noncognate branching events; (5) modified recombinant polymerases that exhibit altered translocation properties as compared to the corresponding wild-type polymerases; (6) modified recombinant polymerases that exhibit increased nucleotide residence time; (7) sequencing of nucleic acid templates using more than one mode; and/or (8) any other combination of embodiments described herein.

C. Enhanced Sequencing Using Iterative Sampling of Unincorporatable Nucleotide Analogs The present invention also employs nucleotide based competitive reagent compositions for identifying sequence elements, despite not being incorporated in a nascent nucleic acid strand. In particular, the unincorporatable nucleotide analogs of the invention, while not being incorporatable, may be nonetheless capable of specifically associating with the polymerase enzyme. That is, the polymerase will sample the unincorporatable nucleotides, retaining them within the active site for a greater length of time than nucleotides that are not complementary to the position in the template nucleic acid, and release them when they cannot be incorporated. By providing different types of nucleotide or nucleoside analogs, e.g., mimetics of A, G, T, C, and/or U, bearing distinguishable labels, e.g., spectrally resolvable fluorophores or other labeling groups, one can monitor the sampling of these nucleotides as an indication of the nucleotide that is next to be incorporated. For example, one may provide labeled, unincorporatable nucleotide analogs at concentrations in excess of incorporatable nucleotides, e.g., 2×, 5× or even 10× or greater. Each incorporation of an incorporatable nucleotide will, by virtue of the excess concentration, be preceded by repeated sampling events of the unincorporatable nucleotides, which will each carry its associated signal event. The incorporatable nucleotides may then either bear no label, or preferably, bear a label that is distinguishable from the unincorporatable nucleotides, so as to mark the termination of the sampling of a given base and proceeding onto the next base in the sequence. In such cases, it may be desirable to label all incorporatable nucleotides with a single type of fluorophore, i.e., indistinguishable from the label groups on the other types of incorporatable nucleotides present, but distinguishable from all of the unincorporatable nucleotides.

Figure 4:
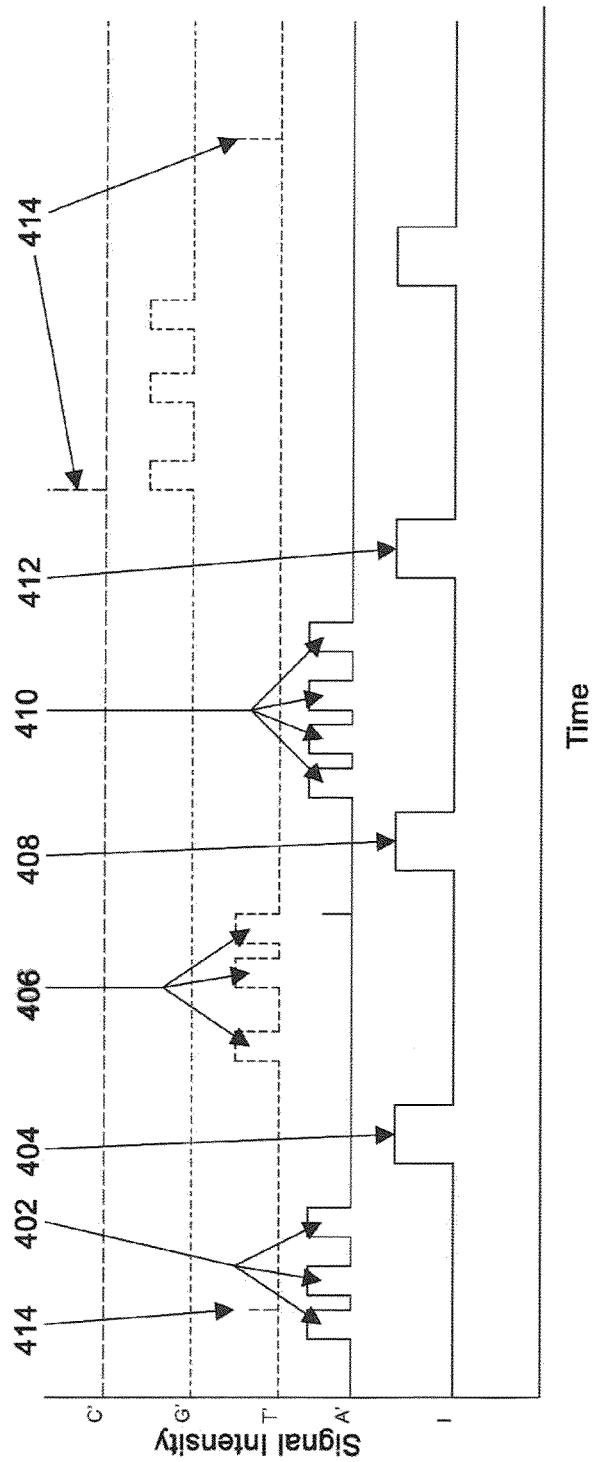
FIG. 4 is a schematic illustration of a sequencing by incorporation reaction in which unincorporatable nucleotides are included in the reaction.

The signal detection for the foregoing process is schematically illustrated in FIG. 4. In particular, FIG. 4 shows a schematic illustration of a set of signal traces from a single molecule sequence by incorporation reaction. As shown, the plot shows five signal traces, one for each type of differentially labeled unincorporatable nucleotide analog (indicated as A', T', G' and C', as well as a trace for the signal associated with the type of label coupled to the incorporatable nucleotide (labeled as "I"). As shown, repeated sampling of the cognate unincorporatable nucleotide analog, e.g., A', provides an iterative set of signal events 402, followed by a signal 404 on the I trace indicating conclusion of the incorporation event. This pattern is repeated for the next base to be incorporated (indicated by iterative signals 406 in the T' trace, followed again by the incorporation signal 408, in the I trace, and again by the iterative sampling signal 410 in the A' trace followed by the incorporation signal 412 in the I trace. Because these unincorporatable nucleotides are mimetic of the base to be incorporated, they possess a longer retention time in the active site than the analog that is not complementary to the next base in the template, and as such, provide a signal profile that is distinguishable from random, incorrect sampling, e.g., as indicated by transient signal events 414. Such iterative sampling may include two, three, four, five, ten or greater than ten signal events for each incorporation.

As noted above, the competitive reagents used are going to be non-reactive in the reaction of interest. In preferred aspects, and without being bound to any particular theory of operation, the competitive compounds may possess structures similar to nucleotides or portions thereof, such that they can competitively interact with the reaction of interest, e.g., through association with the polymerase active site. By way of example, such structures may comprise a polyphosphate component, e.g., a pyrophosphate, triphosphate, tetraphosphate, pentaphosphate, or longer phosphate chain, so that the compound mimics one or more of a nucleotide or the product of a polymerase mediated incorporation reaction, which is capable of competitively interacting with the polymerase, relative to the nucleotide analogs.

In certain preferred cases, additional components may be coupled to the polyphosphate component that mimic other portions of the nucleotide or nucleotide analog. By way of example, the polyphosphate component may be coupled to a cyclic and/or aromatic component that may structurally mimic the nucleoside component in its interaction with the polymerase. Such structures are generally illustrated by the following structure:

P—(P)$_n$-A;

where P is a phosphate or phosphonate group, n is an integer from 1 to about 6, and A includes a cycloalkyl or aryl group, a carbohydrate group, or the like.

In the case of nucleotide analogs used in analytical primer extension reactions, e.g., in nucleic acid sequence analysis, such nucleotide analogs will be unincorporatable in such primer extension reaction by the polymerase used. Further, in preferred aspects, such unincorporatable analogs will typically still be capable of interaction with the polymerase, e.g., active site binding, but will be unable to be incorporated in a primer extension reaction. In preferred aspects, this is accomplished by providing nucleotide analogs that possess nonhydrolyzable groups within the phosphate chain, such that the phosphoester linkage between the analog and the primer strand, cannot be formed, as mediated by the polymerase. One particularly effective approach to producing an unincorporatable nucleotide analog includes replacing the phosphoester linkage between the alpha and beta phosphate of a nucleoside polyphosphate with a nonhydrolyzable linkage.

One example of such an analog is illustrated below, where the oxygen group between the alpha and beta phosphate groups is replaced with an nonhydrolyzable linkage, such as the illustrated amino group.

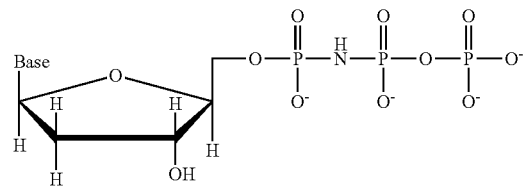

Although illustrated as an amino linkage, it will be appreciated that a variety of other linkages may be used between the alpha and beta phosphates, e.g., an amino, methyl, thio, or other linkages not hydrolyzed by polymerase activity. Additionally, although illustrated as including three phosphate groups analogous to a nucleoside triphosphate, it will be appreciated that other polyphosphate configurations may be employed in the invention, including, for example, tetraphosphate analogs, pentaphosphate analogs, hexaphosphate analogs, and the like.

Thus, the structures employed in certain preferred aspects of the invention may generally be described with reference to the following structure:

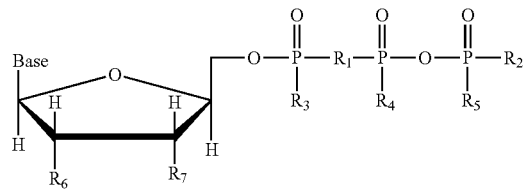

where $R_1$ comprises a linking group that is non-hydrolyzable by the polymerase enzyme being used. Particularly preferred linkages include amino linkages, alkyl linkages, e.g., methyl, and thio linkages. While $R_2$ may comprise oxygen, in some preferred aspects, it will include additional phosphate groups, e.g., mono-, di-, or triphosphate groups coupled to the gamma phosphate group. Alternatively or additionally, the $R_2$ group may include, in addition to or instead of additional phosphate groups, labeling functionalities that provide for the detection of the competitive substrates, but still permit its distinguishing from the incorporatable nucleotides. In other aspects, the $R_2$ group may include moieties that provide other functionalities to the reaction system other than as a labeling group. For example, $R_2$ may comprise an agent that reduces the potential for photodamaging effects on a polymerase enzyme, either coupled directly to the terminal phosphate group, or through a linking group.

The relative concentration of the competitive substrates to the incorporatable substrates, within a reaction mixture may generally be varied in accordance with a desired application. In particular, because the concentration of the competitive substrates affects the interactions of the complex with the incorporatable nucleotides, one can modulate those interactions by altering the ratios between incorporatable nucleotides and competitive substrates. In typical applications, however, the relative molar concentration of competitive substrate will range from about 0.5× to about 10×, 20× or greater of the concentration of the actual substrates (or incorporatable nucleotide analogs). Thus, the concentration ratio of unincorporatable nucleotide analogs to incorporatable nucleotide analogs will typically range from a lower ratio of from about 0.1:1, 0.2:1, 0.5:1 and 1:1, to an upper ratio of about 2:1, 3:1, 5:1, 10:1 or even 20:1, with each iteration of the foregoing being encompassed in the disclosure hereof.

As will be appreciated, iterative sampling of unincorporatable nucleotides can be used in combination with any other embodiments described herein, including: (1) reaction conditions that increase the frequency of branching fraction nonincorporation events; (2) modified recombinant polymerases that exhibit increased branching fractions as compared to the corresponding wild-type polymerases; (3) two slow-step enzyme systems; (4) detection of noncognate branching events; (5) modified recombinant polymerases that exhibit altered translocation properties as compared to the corresponding wild-type polymerases; (6) modified recombinant polymerases that exhibit increased nucleotide residence time; (7) sequencing of nucleic acid templates using more than one mode; and/or (8) any other combination of embodiments described herein.

D. Enhanced Sequencing Using Two Slow-Step Enzyme Systems Combined with Detection and Analysis of Branch Fraction Nonincorporation Events Enzyme systems that exhibit kinetic mechanisms having two or more slow, kinetically observable, or partially rate-limiting reaction steps within an observable phase of the polymerase reaction can be useful for example, in single-molecule, real-time observations of such enzyme activity, which rely, at least in part, on detecting and identifying the enzyme reaction as it is occurring. By designing the reaction system to have two or more partially rate-limiting steps (i.e., "two slow-step" enzyme systems), the relative number of short, difficult to detect, events can be lowered. Details regarding enzyme systems exhibit kinetic mechanisms having two or more slow, kinetically observable, or partially rate-limiting reaction steps within an observable phase of the polymerase reaction can be found in Bjornson et al. PCT Application Serial Number PCT/US2009/002003 TWO SLOW-STEP POLYMERASE ENZYME SYSTEMS AND METHODS, incorporated herein by reference in its entirety for all purposes.

Certain types of template nucleic acid sequences present unique challenges during single molecule sequencing. For example, during single molecule sequencing of homonucleotide stretches (i.e., a portion of a template nucleic acid having two or more consecutive bases that are identical), ascertaining the number of nucleotide incorporation events that are represented by a series of signal pulses generated under high branch fraction sequencing conditions can be difficult using previous typical enzyme systems that exhibit one slow-step. By way of example, if 20 consecutive signal pulses are detected from a fluorescent-labeled nucleotide analog of dATP (e.g., A488dA4P, see below), a system that detects signal pulses and analyzes the time-sequence of those signal pulses for purposes of calling bases may not be able to accurately determine how many dATP analog incorporation events (i.e., the number of consecutive T residues in the template sequence) are represented by the 20 signal pulses. Accordingly, enzyme systems that permit a more predictable distribution of nucleotide binding events per incorporation are desirable, because, e.g., the number of nucleotides within a homonucleotide stretch can be determined by using a multiple of the expected number of binding events per incorporation.

Figure 5:
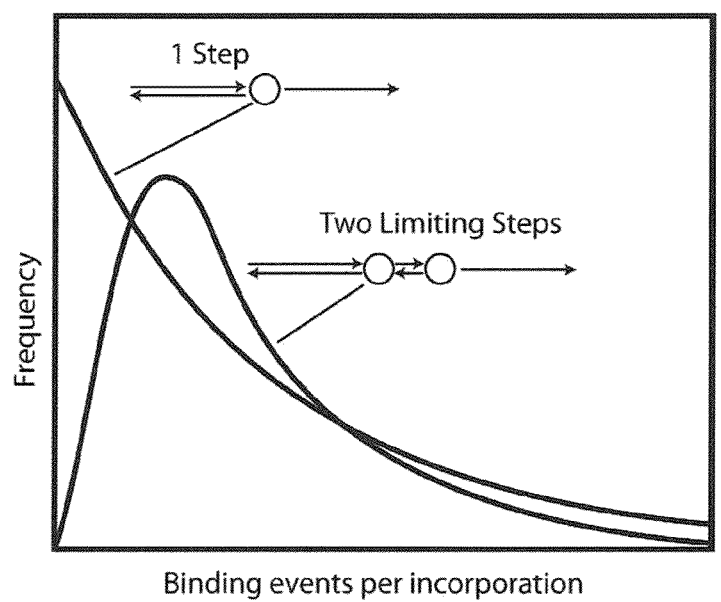
FIG. 5 shows a theoretical representation of the frequency of binding events per incorporation for a polymerase reaction having one rate-limiting step or two rate-limiting steps within an observable phase.

In one aspect, the present invention provides two slow-step enzyme systems that provide a more predictable frequency or rate of nucleotide binding events (e.g., the number of times a nucleotide or nucleotide analog samples the active site of the polymerase) per incorporation event. While not being bound by any particular theory, the following theoretical basis is provided for obtaining improved single-molecule sequencing results, e.g., for homonucleotide stretches, by using a system having two or more slow steps within an observable phase. A model for the effect of two slow steps on the number of nucleotide binding events is described herein and illustrated in FIG. 5. FIG. 5 shows a plot of calculated number of binding events per incorporation for cases in which (1) one step is rate-limiting and (2) two equivalent partially rate-limiting (slow) steps are present for the observable phase in which the nucleotide is associated with the enzyme before unbinding.

For the case in which one step is rate-limiting, the distribution for the number of binding events per incorporation can be represented by the single exponential equation:

$$y = A_0 e^{-kt} \qquad \text{Eq. 1}$$

This represents the case in which, for example, one conformational change of the enzyme after nucleotide binding is the single slow step.

FIG. 5 illustrates that where one slow-step is present in this phase, there is an exponentially decreasing number of binding events per incorporation, providing a distribution in which there is a relatively high probability that the number of binding events per incorporation will be low. In this scenario, it can be more challenging to distinguish homonucleotide stretches of the same base in the DNA template.

For the case in which there are two slow steps associated with binding of a nucleotide, for example via two consecutive conformational changes with similar rate constants, the number of binding events can be represented by a sum of two exponentials with an equation:

$$y = A_0 e^{-k_1 t} - B_0 e^{-k_2 t} \qquad \text{Eq. 2}$$

FIG. 5 illustrates that for the case in which there are two slow steps, the probability of one or a low number of binding events per incorporation is relatively low as compared to enzyme systems having one slow step. In addition, the probability distribution for two slow steps exhibits a peak in the plot, with the most frequently observed number of binding events per incorporation greater than zero. This type of distribution can be advantageous for single-molecule sequencing where it is desired to resolve homonucleotide stretches. In this scenario, the expected number of binding events per incorporation will be a corresponding multiple factor of the most frequent occurrence of binding events per incorporation as governed by this distribution.

The two slow steps can include, e.g., nucleotide addition, enzymatic isomerization (such as to or from a closed state), and cofactor binding or release. The use of a distribution of pulses to determine a kinetic mechanism having two slow (kinetically observable) steps is described, for example, in Miyake et al. Analytical Chemistry 2008 80 (15), 6018-6022. The determination of the steps in a multistep reaction such as a polymerase reaction is described, for example, in Zhou, et al. J. Phys. Chem. B, 2007, 111, 13600-13610.

As noted above, the present invention provides enzyme systems that exhibit kinetic mechanisms having two or more slow, kinetically observable, or partially rate-limiting reaction steps within an observable phase of the polymerase reaction observable phase will generally have a time period during which the phase is observable. The time period for a bright phase, for example, can be represented by the pulse width. The time period for a dark phase can be represented, for example, by the interpulse distance. The length of each time period will not be the same for each nucleotide addition, resulting in a distribution of the length of the time periods. In some cases, the time periods with the shortest length will not be detected, leading to errors, for example in single-molecule sequencing. We have found that by designing enzyme systems such as polymerase reaction systems in which there are two slow, or kinetically observable, steps within an observable phase, the relative number of short, unobservable, time periods can be reduced, resulting in a higher proportion of observable sequencing events, and allowing for a more accurate determination of nucleotide sequence. As used herein, an observable phase includes phases that are not directly observable, but can be ascertained by measurements of other, related phases. For example, the lengths of dark phases can be observed by measuring the times between optical pulses corresponding to a related bright optical phase. Also as described herein, a phase which is dark under some labeling conditions can be bright under other labeling conditions.

In natural polymerase-mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation is relatively complex.

The process can be described as a sequence of steps, wherein each step can be characterized as having a particular forward and reverse reaction rate that can be represented by a rate constant. One representation of the incorporation biochemistry is provided in FIG. 6. It is to be understood that the scheme shown in FIG. 6 does not provide a unique representation of the process. In some cases, the process can be described using fewer steps. For example, the process is sometimes represented without inclusion of the enzyme isomerization steps 606 and 610. Alternatively, the process can be represented by including additional steps such as cofactor binding. Generally, steps which can be slow, and thus limit the rate of reaction will tend to be included. The present invention relates to methods, systems, and compositions in which the polymerization reaction has two or more slow steps within certain phases of the polymerase reaction. Various schemes can be used to represent a reaction having two slow steps that may have more or fewer identified steps. In some cases the two or more slow steps are consecutive. In some cases, there can be intervening fast steps between the two or more slow steps.

Figure 6:
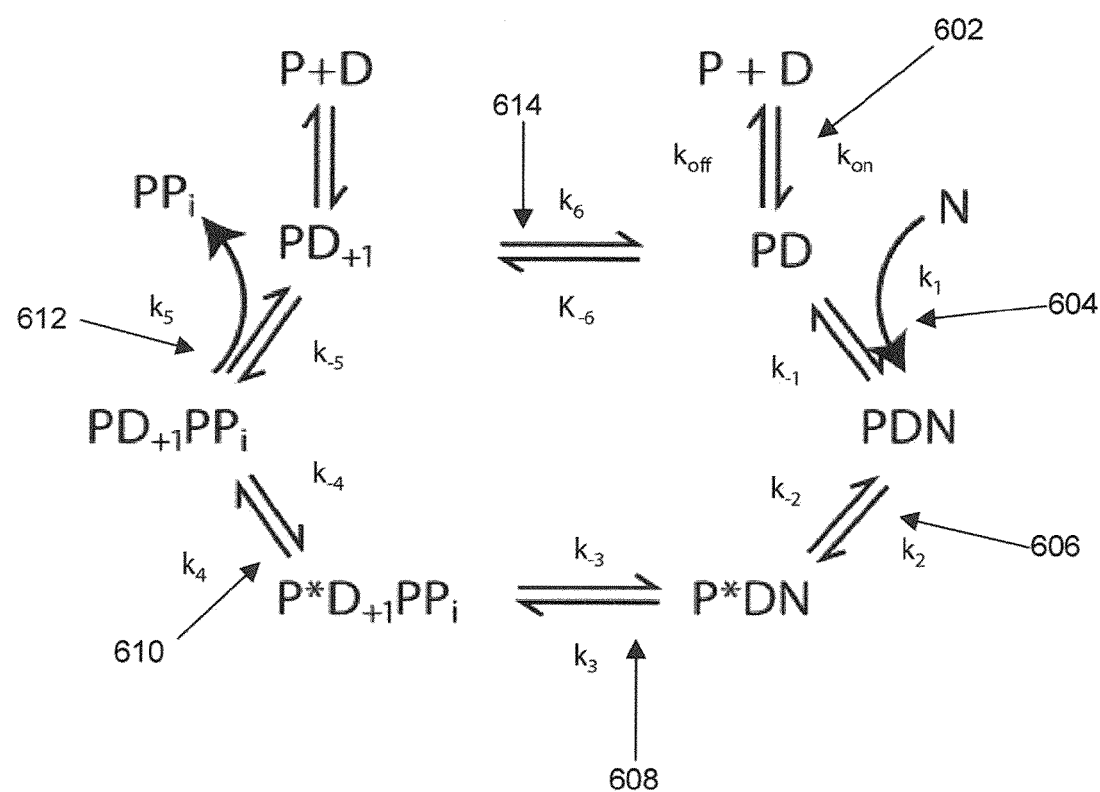
FIG. 6 is a schematic illustration of the reaction cycle for polymerase-mediated nucleic acid primer extension.

As shown in FIG. 6, the synthesis process begins with the binding of the primed nucleic acid template (D) to the polymerase (P) at step 602. Nucleotide (N) binding with the complex occurs at step 604. Step 606 represents the isomerization of the polymerase from the open to closed configuration. Step 608 is the chemistry step where the nucleotide is incorporated into the growing strand of the nucleic acid being synthesized. At step 610, polymerase isomerization occurs from the closed to the open position. The polyphosphate component that is cleaved upon incorporation is released from the complex at step 612. The polymerase then translocates on the template at step 614. As shown, the various steps can include reversible paths and may be characterized by the reaction constants shown in FIG. 6 where:

$k_{on}/k_{off}$=DNA binding/release;
$k_1/k_{-1}$=nucleotide binding/release;
$k_2/k_{-2}$=polymerase isomerization (open/closed);
$k_3/k_{-3}$=nucleotide incorporation (chemistry);
$k_4/k_{-4}$=polymerase isomerization (closed/open);
$k_5/k_{-5}$=polyphosphate release/binding;
$k_6/k_{-6}$=polymerase translocation.

Thus, during steps 604 through 610, the nucleotide is retained within the overall complex, and during steps 604 and 606, reversal of the reaction step will yield an unproductive event, i.e., not resulting in incorporation. For example, a bound nucleotide at step 604 may be released regardless of whether it is the correct nucleotide for incorporation.

By selecting the appropriate polymerase enzyme, polymerase reaction conditions, and polymerase substrates, the absolute and relative rates of the various steps can be controlled. We have found that controlling the reaction such that the reaction exhibits two or more kinetically observable, or slow steps can produce a nucleic acid polymerization reaction in which the incorporation of the nucleotides can be observed more accurately. These characteristics are particularly useful for sequencing applications, and in particular single-molecule DNA sequencing.

In some cases, the invention involves a process having two or more kinetically observable steps that comprise steps after nucleotide binding through the step of product release. For the mechanism shown in FIG. 6, this would be, for example, any of steps 606, 608, 610, and 612. In some cases, steps 608 (nucleotide incorporation) and 612 (product release) are the two slow, or kinetically observable steps. As noted previously, where one desires systems with slow steps in a dark phase, the invention may involve a process having two or more slow steps that comprise the steps after product release through nucleotide binding. For the mechanism shown in FIG. 6, this would include steps 614 and 604.

In some cases, the invention involves a process in which there are two or more slow steps in two different observable phases within the polymerization, for example, two slow steps in a bright phase and two slow steps in a dark phase. For example, this could include a system having two slow steps in the steps after nucleotide binding through product release, and two slow steps for the steps after product release through nucleotide binding.

As is described herein, producing a process in which there are two or more slow steps in these portions of the polymerase reaction can result in a higher proportion of detectable enzyme states which can be useful, for example, to observe the sequential incorporation of nucleotides for nucleotide sequencing.

By the term slow-step we generally mean a kinetically observable step or partially rate-limiting step. The slow step need not be slow in the absolute sense, but will be relatively slow as compared with other steps in the enzymatic reaction. The slow, or kinetically observable steps, can be, for example, each partially rate-limiting, in that the rate of the step has a measurable effect on the kinetics of the enzymatic reaction. An enzymatic process, such as nucleic acid polymerization, can have both slower, kinetically observable steps and faster steps which can be so fast that they have no measurable effect on the kinetics, or rate, of the reaction. In some reactions, there can be a single rate-limiting step. For such reactions, the kinetics can be characterized by the rate of that single step. Other reactions will not have a single rate-limiting step, but will have two or more steps which are close enough in rate such that the characteristics of each will contribute to the kinetics of the reaction. A kinetically observable step is generally a step which is slow enough relative to the other steps in the reaction such that it can be experimentally ascertained. The experimental identification of a kinetically observable step can be done by the methods described herein, or by methods for assessing the kinetics of chemical and enzymatic reactions known in the art. For the current invention, the slow, or kinetically observable steps, need not be the slowest step or the rate-limiting step of the reaction. For example, a process of the current invention can involve a reaction in which step 604, nucleotide addition is the slowest (rate-limiting) step, while two or more of steps 606, 608, 610, or 612 are each kinetically observable.

As used herein, the term rate, as applied to the steps of a reaction can refer to the average rate of reaction. For example, when observing a single-molecule reaction, there will generally be variations in the rates as each individual nucleotide is added to a growing nucleic acid. In such cases the rate of the reaction can be represented by observing a number of individual events, and combining the rates, for example, by obtaining an average of the rates.

As used herein, the reference to the rate of a step or rate constant for a step can refer to the forward reaction rate of the polymerase reaction. As is generally understood in the art, reaction steps can be characterized as having forward and reverse rate constants. For example, for step 608, $k_3$ represents the forward rate constant, and $k_3$ represents the reverse rate constant for the nucleotide incorporation. Some reaction steps, such as step 608, constitute steps which would be expected to be first order steps. Other steps, such as the forward reaction of step 604, with rate constant $k_2$, would be expected to be second order rate constants. For the purposes of the invention, for comparing the rate or the rate constant of a first order to a second order step, the second order rate constant $k_2$ can be treated as a pseudo-first order rate constant with the value $[N]*k_2$ where the concentration of nucleotide $[N]$ is known.

It is generally desirable that the kinetically observable steps of the invention have rate constants that are lower than about 1000 per second. In some cases, the rate constants are lower than about 500 per second, lower than about 200 per second, lower than about 100 per second, lower than about 60 per second, lower than about 50 per second, lower than about 30 per second, lower than about 20 per second, lower than about 10 per second, lower than about 5 per second, lower than about 2 per second, or lower than about 1 per second.

In some embodiments the slowest of the two or more kinetically observable steps has a rate constant when measured under single-molecule conditions of between about 500 to about 0.1 per second, about 200 to about 0.1 per second, about 60 to about 0.5 per second, about 30 per second to about 2 per second, or about 10 to about 3 per second.

The ratio of the rate constants of each the two or more slow steps is generally greater than 1:10, in some cases the ratio of the rate constants is about 1:5, in some cases the ratio of the rate constants is about 1:2, in some cases, the ratio of rate constants is about 1:1. The ratio of the rate constants can be between about 1:10 and about 1:1, between about 1:5 and about 1:1, or between about 1:2 and about 1:1.

In some cases it is useful to consider the two slow-step system in terms of rates rather than rate constants. It is generally desirable that the kinetically observable steps of the invention have rates that are lower than about 1000 molecules per second when the reactions are carried out under single-molecule conditions. In some cases, the rates are lower than about 500 molecules per second, lower than about 200 molecules per second, lower than about 100 molecules per second, lower than about 60 molecules per second, lower than about 50 molecules per second, lower than about 30 molecules per second, lower than about 20 molecules per second, lower than about 10 molecules per second, lower than about 5 molecules per second, lower than about 2 molecules per second, or lower than about 1 molecule per second.

In some embodiments the slowest of the two or more kinetically observable steps has a rate when measured under single-molecule conditions of between about 500 to about 0.01 molecules per second, between about 200 to about 0.1 molecules per second, between about 60 to about 0.5 molecules per second, about 30 molecules per second to about 2 molecules per second, or about 10 to about 3 molecules per second.

The ratio of the rates of each the two or more slow steps is generally greater than 1:10, in some cases the ratio of the rates is about 1:5, in some cases the ratio of the rates is about 1:2, in some cases, the ratio of rates is about 1:1. The ratio can be between about 1:10 and about 1:1, between about 1:5 and about 1:1, or between about 1:2 and about 1:1.

A two or more slow-step system of the present invention can be obtained by selecting the correct set of polymerase enzyme, polymerase reaction conditions, and polymerase reaction substrates.

Table B presents exemplary Φ29 mutants that can exhibit two slow step behavior under appropriate reaction conditions. The first three modified polymerases exhibit the most pronounced two slow step behavior, followed by the next six. As noted, the polymerases are optionally exonuclease-deficient; for example, they can also include an N62D substitution.

TABLE B

| |
| --- |
| A484E/E375Y/K512Y/T368F |
| A484Y/E375Y/K512Y1T368F |
| N387L/E375Y/K512Y/T368F |
| T372Q/E375Y/K512Y/T368F |
| T372L/E375Y/K512Y/T368F |
| T372Y/K478Y/E375Y/K512Y/T368F |
| I370W/E375Y/K512Y/T368F |
| F198W/E375Y/K512Y/T368F |
| L381A/E375Y/K512Y/T368F |
| E375Y/K512Y/T368F |

The polymerase reaction conditions can also be important for obtaining a two slow-step enzyme system. In particular, polymerase reaction conditions include components selected to produce two slow-step kinetics. The polymerase reaction conditions include the type and concentration of buffer, the pH of the reaction, the temperature, the type and concentration of salts, the presence of particular additives which influence the kinetics of the enzyme, and the type, concentration, and relative amounts of various cofactors, including metal cofactors. The term "polymerase reaction conditions" as used herein generally excludes the concentration of the polymerase enzyme or the concentration of the primer-template complex. Thus, two reactions are run under substantially the same polymerase reaction conditions where the first reaction has a small amount of polymerase enzyme, such as a single polymerase enzyme, and a small amount of primer template complex, such as a single primer-template complex associated with a single polymerase enzyme, and the second reaction has a higher concentration of polymerase enzyme, for example a concentration of polymerase enzyme of about 0.05 µM to 0.5 µM, and about 0.01 µM to about 0.1 µM.

It some embodiments the type and concentration of buffer are chosen in order to produce a reaction having two slow steps. Enzymatic reactions are often run in the presence of a buffer, which is used, in part, to control the pH of the reaction mixture. We have found that in some cases the type of buffer can influence the kinetics of the polymerase reaction in a way that can lead to two slow-step kinetics. For example, in some cases, we have found that the use of TRIS as buffer is useful for obtaining a two slow-step reaction. Buffers suitable for the invention include, for example, TAPS (3-{[tris(hydroxymethyl)methyl]amino}propanesulfonic acid), Bicine(N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two slow-step kinetics. The pH can be adjusted to a value that produces a two slow-step reaction mechanism. The pH is generally between about 6 and about 9. In some cases, the pH is between about 6.5 and about 8.0. For example, the pH can be by way of illustrations between about 6.5 and 7.5. The pH can be about 6.5, 6.6, 6.7, 6.8, 6.9, 7.0, 7.1, 7.2, 7.3, 7.4, or 7.5.

The temperature of the reaction can be adjusted in order to obtain a reaction exhibiting two slow-step kinetics. The reaction temperature may depend upon the type of polymerase which is employed. Temperatures between about 15° C. and 90° C., between about 20° C. and 50° C., between about 20° C. and 40° C., or between about 20° C. and 30° C. can be used.

In one aspect, the present invention is directed to the use of a mixture of catalytic and non-catalytic metal ions in a nucleic acid synthesis reaction, to modulate the reaction kinetics of the complex. Thus, in at least one aspect, the invention is directed to nucleic acid synthesis reaction mixtures that include both catalytic and non-catalytic metals. The molar ratio of catalytic to non-catalytic metals in the reaction mixture will generally vary depending upon the type of kinetic modulation desired for a given synthesis reaction, where slower incorporation would suggest higher levels of non-catalytic metal ions. Typically, such ratios of catalytic to non-catalytic metals in the reaction mixture will vary from about 10:1 to about 1:10, and preferably, from about 10:1 to about 1:5, depending upon the desired level of modulation, the particular enzyme system employed, the catalytic and non-catalytic metal cofactors that are used, and the reaction conditions. In particularly preferred aspects, the ratios of catalytic to non-catalytic metals will be in the range of from about 5:1 to about 1:1, with ratios of from about 2.5:1 to about 1.5:1 being particularly preferred.

In addition to the presence of such metals at the ratios described herein, the absolute concentration of such metals in the reaction mixtures will typically range from about 0.05 mM to about 50 mM, in some cases from about 0.1 mM to about 10 mM, in some cases from about 0.1 mM to about 5 mM. The composition can include, for example, from about 0.1 mM $MnCl_2$ to about 1 mM $MnCl_2$ and from about 0.1 mM $CaCl_2$ to about 2 mM $CaCl_2$; or from about 0.2 mM $MnCl_2$ to about 1 mM $MnCl_2$ and from about 0.4 mM $CaCl_2$ to about 1.5 mM $CaCl_2$.

As will be appreciated, the two slow-step enzyme systems described above can be used in combination with any other embodiments described herein, including: (1) reaction conditions that increase the frequency of branching fraction non-incorporation events; (2) modified recombinant polymerases that exhibit increased branching fractions as compared to the corresponding wild-type polymerases; (3) iterative sampling of unincorporatable nucleotides; (4) detection of noncognate branching events; (5) modified recombinant polymerases that exhibit altered translocation properties as compared to the corresponding wild-type polymerases; (6) modified recombinant polymerases that exhibit increased nucleotide residence time; (7) sequencing of nucleic acid templates using more than one mode; and/or (8) any other combination of embodiments described herein.

E. Enhanced Sequencing by Detection of Noncognate Branching Events

Nucleic acid sequencing approaches that utilize fluorescent-labeled nucleotide analogs typically require the detection of at least four colors—one color for each nucleotide representing the four different bases A, T/U, C, or G. Sequencing by incorporation methods, e.g., real time single molecule sequencing, also typically involves the detection of at least four different fluorescent labels corresponding to each of four nucleotide analogs. New approaches for reducing the number of different fluorescent labels to be detected by a sequencing system are provided herein; these approaches can reduce the cost of nucleic acid sequencing by reducing, e.g., the number of color channels and other associated optical capabilities of the detection system.

The present invention provides new methods for nucleic acid sequencing that reduce the number of required colors to be detected by the sequencing system. Such methods utilize noncognate branching to determine which nucleotide is incorporated at a particular incorporation site during a nucleic acid polymerization reaction. For the purposes of this disclosure, noncognate branching refers to the branching (or iterative sampling) of a nucleotide, where the base of the nucleotide would incorrectly pair (not form a correct Watson-Crick base pair) with the base at the incorporation site of the template nucleic acid. For example, when the incorporation site of a template nucleic acid contains the base guanine (or G), it has been observed that branching (or sampling) of dGTP nucleotides or nucleotide analogs occurs at an appreciable frequency. The frequency of noncognate branching is sufficient to permit the identification of the nucleotide actually incorporated, regardless of whether the nucleotide actually incorporated is labeled. For instance, multiple signal pulses derived from noncognate branching (i.e., iterative sampling)

of fluorescently-labeled G-containing nucleotides or nucleotide analogs can be utilized by a signal detection and sequencing system to determine that a C-containing nucleotide (which does not require a fluorescent label) was actually incorporated at that site. Thus, the temporal sequence of incorporation of four different nucleotides can be ascertained by utilizing, at most, three different fluorescent labels.

Noncognate branching of T-containing nucleotides has also been observed when the base at the incorporation site of the template is T. Accordingly, it is possible to determine the sequence of a nucleic acid template using a two-color detection system, where noncognate branching of G- and T-containing nucleotides—alone—permits the identification of incorporation of C- and A-containing nucleotides, thereby eliminating the requirement that C- and A-containing nucleotides be labeled. As will be appreciated, the present invention provides enhanced sequencing using noncognate branching, where the sampling noncognate nucleotide can be any nucleotide that would incorrectly pair with the corresponding base of the template nucleic acid.

It will be appreciated that noncognate branching events, in conjunction with a sequencing system that detects and accounts for noncognate branching events, are useful for sequencing applications other than those designed to reduce, e.g., the number of color channels required of the sequencing system. For example, even where sequencing is performed using four colors, noncognate branching can be used to validate or assist in the determination by a sequencing system of which nucleotide was incorporated at a particular site. Thus, when the base at the incorporation site of a template of unknown sequence is G, and the quantity or quality of signal pulses generated from sampling of dCTP analogs does not unambiguously permit assignment of dCTP as the incorporating nucleotide at that site, noncognate branching of labeled dGTP nucleotides facilitates the determination that dCTP was indeed incorporated at the site.

As will be appreciated, enhanced sequencing by detection and analysis of noncognate branching events can be used in combination with any other embodiments described herein, including: (1) reaction conditions that increase the frequency of branching fraction nonincorporation events; (2) modified recombinant polymerases that exhibit increased branching fractions as compared to the corresponding wild-type polymerases; (3) iterative sampling of unincorporatable nucleotides; (4) two slow-step enzyme systems; (5) modified recombinant polymerases that exhibit altered translocation properties as compared to the corresponding wild-type polymerases; (6) modified recombinant polymerases that exhibit increased nucleotide residence time; (7) sequencing of nucleic acid templates using more than one mode; and/or (8) any other combination of embodiments described herein.

II. Sequencing by Incorpration Using More Than One Mode of Sequencing

A sequencing composition may be especially advantageous for one particular purpose or type of template nucleic acid, but may exhibit limitations for a second purpose or type of template nucleic acid. As described in detail herein, sequencing under conditions that promote a relatively high branching fraction, in combination with appropriate signal analysis, reduces the likelihood of base calling errors that result from undetected signal pulses generated from genuine nucleotide incorporation events. Accordingly, the base calling accuracy of sequencing by incorporation reactions that exhibit a relatively high level of branch fraction nonincorporation events—when combined with a sequencing system that accounts for such redundant signal pulses per incorporation event—can be higher than the level of accuracy achieved under low branch rate conditions. On the other hand, sequencing under conditions in which the branching fraction is low typically results in improved sequence read length, as the number of incorporation events will be greater before the polymerase has an opportunity to dissociate from the template nucleic acid. Longer read lengths simplify assembly of contig information, e.g., to facilitate genomic sequencing.

De novo sequencing (sequencing a template nucleic acid of unknown sequence, e.g., genomic DNA of unknown sequence) is, in some cases, optimally performed under a combination of both high accuracy and high read length conditions. Identifying one particular sequencing composition that adequately fulfills both of these competing requirements is not necessary in the present invention. Instead, the present invention provides new methods and systems for sequencing a template nucleic acid, in which the template nucleic acid is sequenced using more than one sequencing mode ("multimodal" or "variable mode" sequencing). As used herein, a sequencing mode refers to a sequencing composition (e.g., a mixture of a particular nucleic acid polymerase, nucleotides or nucleotide analogs, metal cofactors, and other components of a sequencing reaction) and other conditions that affect nucleic acid polymerization, e.g., reaction temperature. The methods and systems of the invention utilize a first sequencing mode that confers a particular benefit for purposes of generating a sequence readout (e.g., high accuracy), and then switch to a second (or more) sequencing mode that confers a benefit not realized during the first sequencing mode, e.g., a high sequence read length. As will be appreciated, any number of different modes can be employed by the methods and systems of the inventions, e.g., 2, 3, 4, 5, 10, or 20 different modes may be used to sequence a particular nucleic acid template until the desired results are achieved. For example, a template nucleic acid can be sequenced multiple times using a "high accuracy" mode and/or multiple times using a "high read length" mode, in order to obtain the accuracy and fold coverage useful for, e.g., de novo sequencing. Alternatively, a single template nucleic acid can be partially sequenced using, e.g., a high accuracy mode, and the mode can be switched prior to complete sequencing of the template to, e.g., a high read length mode.

A sequencing mode in which, e.g., high accuracy is desirable can employ, e.g., reaction conditions that induce a relatively high average branching fraction during the nucleic acid polymerization reaction. Such reaction conditions are described in detail herein. In one embodiment of the invention, one or more metal cofactors may be included in the sequencing composition at concentrations and/or ratios that induce a relatively high average branching fraction. Metal cofactors of the invention include, e.g., $Mg^{++}$, $Mn^{++}$, $Zn^{++}$, $Co^{++}$, $Ca^{++}$, $Fe^{++}$, $Cr^{++}$, and/or $Sr^{++}$. Reaction conditions in which metal cofactor identities, concentrations and/or ratios induce high levels of branching are described in detail herein. As described herein, a relatively high level of branching fraction nonincorporation events can be induced in a sequencing composition that includes, e.g., a relatively low concentration of $Mn^{++}$, a sequencing composition that includes $Mg^{++}$, a sequencing composition that includes both $Mg^{++}$ and $Mn^{++}$ with $Mg^{++}$ being included at a higher concentration than $Mn^{++}$, and a sequencing composition that includes $Mn^{++}$ and a metal cofactor other than $Mg^{++}$, e.g., calcium, barium, strontium, iron, cobalt, nickel, tin, zinc, and europium.

A sequencing mode in which, e.g., high read length is desirable can employ, e.g., reaction conditions that discourage branch fraction nonincorporation events during the nucleic acid polymerization reaction. Such reaction conditions are described herein. As described herein, reaction conditions that do not promote branching events include, e.g., $Mn^{++}$ alone at a concentration at which branching is not induced (e.g., greater than 250 µM), or $Mn^{++}$ in combination with a second metal cofactor, e.g., $Mg^{++}$, with the concentration of $Mn^{++}$ being greater than the concentration of $Mg^{++}$. Desirably, sequencing modes of the present invention that produce high read lengths (e.g., a high number of successive incorporation events that are detected by sequencing systems of the invention) can produce read lengths of preferably more than 200 base pairs (bp) or more, more preferably 500 bp or more, more preferably 1000 bp or more, more preferably 10,000 bp or more, or more preferably 50,000 bp or more.

In order to permit the switching between a first sequencing mode and a second (or subsequent or more) sequencing mode, the sequencing composition—including the template nucleic acid and polymerase—is desirably confined within a structure to which additional components can be added to the sequencing composition to achieve the desired subsequent mode. In one aspect, for example, the sequencing of a template nucleic acid under a first sequencing mode occurs within a structure to which a channel, e.g., a microfluidic channel, delivers the reagents necessary to achieve the subsequent mode. For example, switching from a high branch fraction sequencing mode, in which $Mg^{++}$ is the sole catalytic metal ion, to a high read length sequencing mode can be achieved by delivery of $Mn^{++}$ to the sequencing reaction, such that the final concentration of $Mn^{++}$ is about 300 µM or more, about 400 µM or more, about 500 µM or more, about 700 µM or more, or about 1 mM or more.

In a preferred embodiment, the sequencing reactions take place in a structure that provides optical confinement, e.g., a nanohole or zero-mode waveguide. Further details regarding confinement strategies, substrates and systems for monitoring sequencing reactions can be found in co-pending published U.S. Patent Application No. 2007-0188750, and published International Patent Application No. WO 2007/095119, the full disclosures of which are incorporated herein by reference in their entirety for all purposes.

The sequencing methods and systems of the present invention can employ a wide variety of template nucleic acids. In some cases, the template nucleic acid is a linear template. For a linear template, switching between a high accuracy and a high read length mode can result in a read wherein a relatively long stretch of template nucleic acid is sequenced in a given time, wherein generally, multiple regions along the length will be sequenced with high accuracy. The knowledge that the high accuracy regions are arranged in a particular sequential manner can be useful in putting together the sequence of the nucleic acid. In some cases, the template nucleic acid is a circular template. For a circular template, switching between high accuracy and long read length modes can result in the same region of the template nucleic acid sequenced by each of the modes. In a preferred embodiment, the template to be sequenced in more than one sequencing mode is a single-stranded nucleic acid loop. Double-stranded templates can reanneal, reducing primer annealing efficiency and impeding the polymerase-catalyzed extension of a sequencing reaction. In fact, loops can also be preferable to linear templates because a DNA polymerase can only copy a linear template, e.g., to which a primer has been annealed, once before it falls off the distal end of the template. In contrast, a strand-displacing polymerase can replicate a contiguous nucleic acid loop several times. The primer that is annealed to the loop is eventually displaced at its 5'-end upon completion of one revolution of the polymerase around the nucleic acid loop, and as polymerization and displacement continue, a linear, single-stranded product comprising several copies of the nucleic acid sequence of the loop is generated. Accordingly, using nucleic acid loops in sequencing can provide an internal sequencing control.

The methods for preparing closed, single-stranded nucleic acid loops include providing a genomic DNA, a cDNA, or a DNA concatamer and generating double-stranded fragments that each comprise a first strand (e.g., an exonuclease sensitive strand) and a second strand (e.g., an exonuclease resistant strand). In a following step, the two strands in each fragment are separated, and the resulting single-stranded fragments are circularized to produce closed single-stranded nucleic acid loops, which can then be used as templates in a high-throughput sequencing system. Further details regarding the preparation of single stranded nucleic acid loops, and their use as templates in high-throughput sequencing systems, can be found in Patel et al. PCT Application Serial No. PCT/US2009/001930 METHODS AND COMPOSITIONS FOR NUCLEIC ACID SAMPLE PREPARATION, incorporated herein by reference in its entirety for all purposes.

Systems for analyzing the data generated during sequencing of a template nucleic acid using more than one sequencing mode are also a feature of the invention. Such systems will include a signal detector, e.g., in the case of a plurality of arrayed sequencing reactions, an array detector, e.g., an EMCCD. The detector, is then operatively coupled to a data storage and processing system. In a first sequencing mode, e.g., a mode where a high branching fraction is induced, the processing system is capable of interpreting multiple, e.g., redundant, or iterative signal pulses for each nucleotide incorporation event during a sequencing reaction to call bases with increased accuracy. In a subsequent sequencing mode, e.g., a high read length mode in which little or no branching occurs, the processing system is capable of interpreting single signal pulses as nucleotide incorporation events. Further details regarding base calling during sequencing by incorporation methods are found in Tomaney et al. PCT Application Serial No. PCT/US2008/065996 METHODS AND PROCESSES FOR CALLING BASES IN SEQUENCING BY INCORPORATION METHODS, incorporated herein by reference in its entirety for all purposes.

The multi-modal sequencing method of the present invention optionally includes recording signals or signatures, e.g., in a computer readable medium. The signals or signatures can be stored, e.g., as graphic or digital information. Any typical recording device such as a hard drive, memory card, memory stick, optical storage device or floppy drive can be used to record detected signals. Signals or signal signatures can also be deconvoluted or translated to provide, e.g., sequence information, e.g., in sequencing systems of the invention. Signal processing equipment can include, e.g., a computer having appropriate software for converting signals into sequence or assay parameter information.

Signal detection optics can be coupled to cameras, digital processing apparatus, or the like, to record and analyze signals detected in the various systems herein. Systems can include a microscope, a CCD, a phototube, a photodiode, an LCD, a scintillation counter, film for recording signals, and the like. A variety of commercially available peripheral equipment and software is available for digitizing, storing and analyzing a digitized video or digitized optical image, e.g., using PC (Intel x86 or pentium chip-compatible DOS™, OS2™ WINDOWS™, WINDOWS NT™ or WINDOWS95™ based machines), MACINTOSH™, LINUX, or UNIX based (e.g., SUN™ work station) computers or digital appliances. Computers and digital appliances can include software for analyzing and perfecting signal interpretation. This can include standard application software such as spreadsheet or database software for storing signal information. However, systems of the invention can also include statistical analysis software to interpret signal or signature data, e.g., to translate the data into nucleic acid sequence information. For example, many vendors, such as Partek Incorporated (St. Peters, Mo.; www.partek.com) provide software for pattern recognition which can be applied to signal interpretation and analysis. Algorithms for sequencing systems that can be adapted to the invention are also described in Tomaney et al. PCT Application Serial No. PCT/US2008/ 065996 METHODS AND PROCESSES FOR CALLING BASES IN SEQUENCING BY INCORPORATION METHODS, incorporated herein by reference in its entirety for all purposes. Once signal information has been converted into sequence information, standard sequence aalysis software can be used to assemble overlapping sequence information. For example, sequence contigs can be assembled using available software such as DNA Baser (Heracle Software, Germany), or Artemis 11 (Sanger Institute) "Artemis and ACT: Viewing, annotating and comparing sequences stored in a relational database" Carver et al. *Bioinformatics* 2008 PMID: 18845581 DOI: 10.1093/bioinformatics/btn529).

Relationships between datasets (e.g., high accuracy versus high readlength data) can similarly be analyzed, e.g., by pattern recognition software, Bayes classifiers, neural networks, Monte Carlo analysis, Principal Component Analysis (PCA), etc. Further information regarding genetic algorithms and neural networks that can be used to analyze signal or signature information can be found in David E. Goldberg (1989) *Genetic Algorithms in Search, Optimization and Machine Learning* Addison-Wesley Pub Co; ISBN: 0201157675; Timothy Masters (1993) *Practical Neural Network Recipes in C++* (Book & Disk edition) Academic Pr; ISBN: 0124790402; Kevin Gurney (1999) *An Introduction to Neural Networks*, UCL Press, 1 Gunpowder Square, London EC4A 3DE, UK; Christopher M. Bishop (1995) *Neural Networks for Pattern Recognition* Oxford Univ Press; ISBN: 0198538642; Brian D. Ripley, N. L. Hjort (Contributor) (1995) *Pattern Recognition and Neural Networks* Cambridge Univ Pr (Short); ISBN: 0521460867; Rubinstein, R. Y.; Kroese, D. P. (2007) *Simulation and the Monte Carlo Method* (2nd ed.). New York: John Wiley & Sons. ISBN 9780470177938; Tarantola, Albert (2005) *Inverse Problem Theory* Philadelphia: Society for Industrial and Applied Mathematics ISBN 0898715725; Steeb (2008) *The Nonlinear Workbook: Chaos, Fractals, Neural Networks, Genetic Algorithms, Gene Expression Programming, Support Vector Machine, Wavelets, Hidden Markov Models, Fuzzy Logic with C++, Java and SymbolicC++ Programs: 4th edition*. World Scientific Publishing. ISBN 981-281-852-9; Sergios Theodoridis, Konstantinos Koutroumbas, (2009) *Pattern Recognition* (4th edition), Elsevier, ISBN 978-1-59749-272-0, and in a variety of other currently available references. Computers/digital appliances also optionally include or are operably coupled to user viewable display systems (monitors, CRTs, printouts, etc.), printers to print data relating to signal information, peripherals such as magnetic or optical storage drives, user input devices (keyboards, microphones, pointing devices) and the like.

Figure 7:
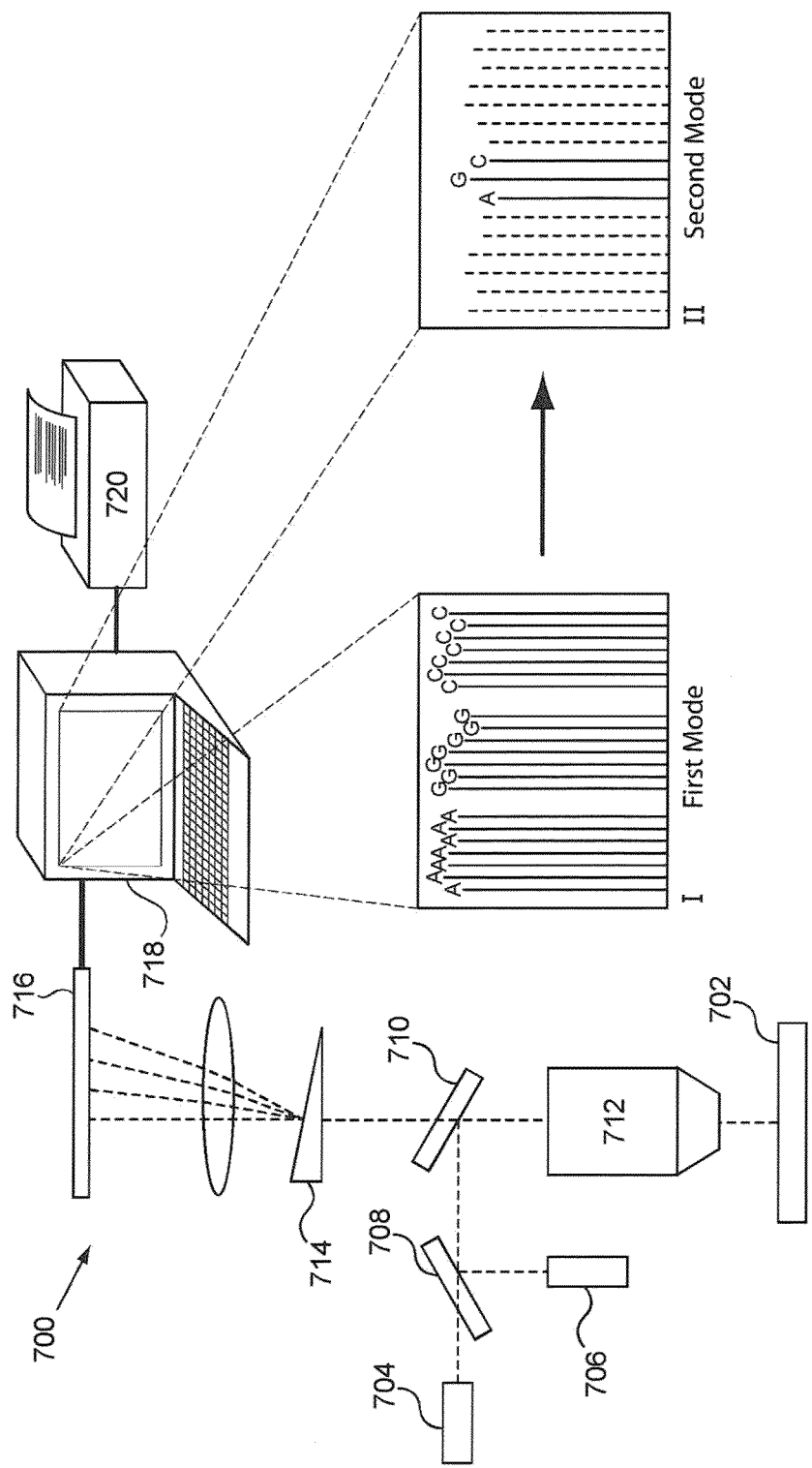
FIG. 7 schematically illustrates a system of the invention that utilizes more than one mode of sequencing.

One example of a system that utilizes more than one mode of sequencing is illustrated in FIG. 7. As shown, system 700 includes substrate 702 of the invention, e.g., upon which sequencing reactions are performed. Optical energy source 704 and additional optical energy source 706 deliver excitation light to the substrate 702, via an optical train. As shown, the optical train includes a dichroic mirror 708 that is transmissive to excitation wavelength of the light from laser 704, while being reflective of light of the wavelength produced by laser 706, allowing both illumination beams to be in the same path. The excitation light is then directed at a second dichroic mirror 710, that reflects the excitation light through objective lens 712, and onto the substrate 702. Optical signals from the substrate 702 are then collected by objective lens 712, and are passed through dichroic 710. The fluorescent signals are then subjected to spatial separation using, e.g., a dispersive optical element, such as an optical grating or prism 714. The separated signals are then focused upon array detector 716, e.g., an EMCCD. The detector, is then operatively coupled to a data storage and processing system, such as computer 718 for processing and storage of the signal data and presentation of the data in a user desired format, e.g., on printer 720.

As shown in FIG. 7, in one example of multi-modal sequencing, a first sequencing mode (Panel I) is produced in which a sequencing by incorporation reaction occurs under higher branch fraction conditions than a second sequencing mode. During the first sequencing mode, the processing system of the computer is capable of interpreting multiple, e.g., redundant, or iterative signal pulses or signatures for each nucleotide incorporation event during a sequencing reaction to call bases. Subsequently, a second sequencing mode (Panel II) is produced in which a sequencing by incorporation reaction occurs with no or very few branch fraction nonincorporation events, and accordingly, longer readlengths. During the second sequencing mode, the processing system of the computer interprets one or very few signal pulses or signatures as a nucleotide incorporation event during the sequencing reaction to call bases. The system can utilize signal pulse or signature data from each sequencing mode in order to determine the sequence of the template nucleic acid. As will be appreciated, a portion of the nucleic acid template can be sequenced once (in one of the two or more sequencing modes) or two or more times (two or more times in the same or multiple sequencing modes).

Although illustrated as an optical train that is transmissive of fluorescent signals, e.g., as provided by dichroic 710, it will be appreciated that fluorescence reflective systems may also be employed. Further details regarding base calling during sequencing by incorporation methods are found in Tomaney et al. PCT Application Serial No. PCT/US2008/065996 METHODS AND PROCESSES FOR CALLING BASES IN SEQUENCING BY INCORPORATION METHODS, incorporated herein by reference in its entirety for all purposes.

As will be appreciated, sequencing of a nucleic acid template in more than one sequencing mode can be combined with (1) reaction conditions that increase the frequency of branching fraction nonincorporation events; (2) modified recombinant polymerases that exhibit increased branching fractions as compared to the corresponding wild-type polymerases; (3) iterative sampling of unincorporatable nucleotides; (4) two slow-step enzyme systems; (5) modified recombinant polymerases that exhibit altered translocation properties as compared to the corresponding wild-type polymerases; (6) modified recombinant polymerases that exhibit increased nucleotide residence time as compared to the corresponding wild-type polymerases; and/or (7) any other combination of embodiments described herein.

III. Delayed Translocation

The present invention also provides polymerases that exhibit delayed translocation as compared to parental/wild type enzymes. Time necessarily lapses between the incorporation of one nucleotide and the incorporation of the next nucleotide due to the sequential (rather than simultaneous) nature of nucleotide incorporation. The duration of this time lapse is determined primarily by the rate at which a polymerase translocates along a template polynucleotide between incorporation events ("translocation" refers to the movement of a DNA polymerase along a template polynucleotide from an initial enzyme binding site to a subsequent enzyme binding site, where the enzyme binding sites correlate to nucleotide incorporation sites). Upon incorporation of a nucleotide, a polymerase is unable to accept another nucleotide until it has gone through the translocation process and moved into the next incorporation site.

When a polymerase translocates at a typical wild-type rate from one incorporation site to the next, a single molecule sequencing (SMS) system has less time to identify and distinguish when the polymerase has moved into the next incorporation site because the rapid translocation affords little separation between the signal pulses arising from incorporation events at one incorporation site and the pulses arising from those events at the next incorporation site. Accordingly, SMS under conditions of typical polymerase translocation rates can have an increased potential for deletion errors relative to the correct template sequence (i.e., signals from incorporation events may not be detected or may be detected but not interpreted as incorporation events). These deletions would be artifacts that constitute errors in sequencing reads.

In accordance with aspects of the present invention, however, the modified recombinant polymerases provided by the present invention that exhibit a translocation delay of longer duration as compared to parental (or wild-type) polymerases are advantageous in the context of SMS because they provide greater temporal separation (i.e., resolution) between the signal pulse emitted while the polymerase resides at one incorporation site from the pulse emitted once the polymerase has entered the next incorporation site. This increased translocation delay permits the sequencing system to interpret signal pulses as correlating to separate and distinct nucleotide incorporation events, and hence greatly diminishes the potential for missed pulses or inaccurately characterized pulses relative to the correct template sequence. Further, a delay in translocation enhances the ability of a sequencing system to distinguish branching events that exhibit short inter-pulse widths from incorporation events that, under the conditions of delayed translocation, exhibit markedly broader inter-pulse widths.

In one aspect, the polymerases of the present invention are engineered to exhibit two sequential translocation kinetic steps that occur at a slower rate as compared to a parental polymerase, e.g., a wild-type parental polymerase. The two translocation kinetic steps may occur at the same rate, or the ratio of their rates may vary up to about 1:5 or 5:1 or more. The occurrence of exceedingly short inter-pulse widths, e.g., the time delay between signal pulses derived from sequential nucleotide incorporation events, is markedly reduced when two slow translocation kinetic steps are engineered into the polymerase. However, the present invention also provides polymerases that exhibit a translocation delay arising from a slow translocation kinetic step in conjunction with a slow kinetic step not related to translocation, e.g., a slow nucleotide and/or nucleotide analog binding step. Further details regarding polymerase systems with two slow kinetic steps can be found in Bjornson et al. PCT Application Serial Number PCT/US2009/002003 TWO SLOW-STEP POLYMERASE ENZYME SYSTEMS AND METHODS, incorporated herein by reference in its entirety for all purposes.

The delay in translocation exhibited by the polymerases of the invention can be more than 2.5× greater, e.g., more than 5× greater, more than 10× greater, more than 15× greater, more than 50× greater, more than 100× greater, more than 1000× greater, or more than 10,000× greater as compared to a parental polymerase (e.g., a wild type Φ29 polymerase) or more. Modified recombinant polymerases of the invention can allow the translocation step of a template-dependent polymerization reaction to be observable, e.g., wherein an otherwise unobservable translocation step (e.g., due to a high rate of translocation of an unmodified polymerase and limitations of the detection system) becomes observable as a result of modification of the polymerase.

The present invention also provides modified recombinant polymerases that include a heterologous polypeptide sequence fused at or near the c-terminus of the polymerase and/or amino acid substitutions or deletions, in order to delay translocation of the polymerase. As noted above, when a polymerase translocates at a typical wild-type rate from one incorporation site to the next, a single molecule sequencing (SMS) system can fail to distinguish when the polymerase has moved into the next incorporation site because the rapid translocation affords little separation between the signal pulses arising from branching and incorporation events at one incorporation site and the pulses arising from those events at the next incorporation site. Accordingly, SMS under conditions of typical polymerase translocation rates is susceptible to incorrect insertions relative to the correct template sequence (i.e., multiple signal pulses arising from branching and incorporation events at a single incorporation site may be interpreted as pulses arising from incorporation events at more than one incorporation site). These insertions are artifacts that constitute errors in sequencing reads.

The present invention provides modified or recombinant DNA polymerases that exhibit decreased translocation rates in order to provide greater temporal separation (i.e., resolution) between the signal pulses emitted while the polymerase resides at one incorporation site from the pulses emitted once the polymerase has entered the next incorporation site. This decreased translocation rate permits the sequencing system to interpret clusters of signal pulses as correlating to nucleotide incorporation sites, and hence greatly diminishes the occurrence of incorrect insertions relative to the correct template sequence.

In one embodiment, delayed translocation is accomplished by encoding a Φ29 DNA polymerase with a heterologous polypeptide sequence fused to the c-terminus of the DNA polymerase. For the purposes of this disclosure, "heterologous" refers to a polypeptide sequence that is not present in the wild-type parental polymerase. That these polymerases retain their functionality is a surprising aspect of the invention. The active site of the polymerase is located in the c-terminal portion of the protein, and previous attempts to modify the c-terminal portion have rendered the polymerase inactive. In one aspect, the heterologous polypeptide sequence can include between 6 and 10 positively charged amino acids, e.g., histidine. This stretch of positively charged amino acids can be encoded immediately downstream of the c-terminus of the polymerase. An example polymerase of this embodiment, comprising a Φ29 polymerase fused to 10 histidine residues at its c-terminus (SEQ ID No. 1), exhibits a translocation rate of 84 sec$^{-1}$, which constitutes a 2.3× delay in translocation as compared to an unmodified parental Φ29 polymerase under identical conditions. In another aspect, an amino acid linker sequence, e.g., a Ser3Gly linker (e.g., Gly-Gly-Gly-Ser-Gly-Gly-Gly-Ser-Gly-Gly-Gly-Ser-Gly) is encoded between the stretch of positively charged amino acids and the C-terminus of the polymerase. An example polymerase of this embodiment, comprising a Φ29 polymerase fused to 10 histidine residues at its c-terminus, with a Ser3Gly linker between the polymerase and the histidine residues (SEQ ID No. 2), exhibits a translocation rate of 220 sec$^{-1}$, which constitutes a 2.4× delay in translocation as compared to an unmodified parental Φ29 polymerase under identical conditions. The affinity of positively charged amino acid residues at the c-terminus of the polymerase for the negatively charged phosphate backbone of DNA decreases the efficiency of polymerase translocation to the next nucleotide incorporation site, thereby causing a delay in translocation. Polymerases of the invention can also exhibit improved polymerase processivity, as the interaction between the polymerase and the phosphate backbone of DNA is enhanced by, e.g., the addition of positively-charged amino acid residues at the c-terminus.

In another embodiment, the polymerases that exhibit delayed translocation comprise amino acid substitutions and/or deletions that modulate interaction of the polymerases with the negatively-charged phosphate backbone of DNA. A number of specific examples of a modified polymerase, e.g. modified to delay polymerase translocation, are described herein. A region of the polymerase responsible for interaction with the DNA template and primer is referred to herein as the binding cleft. Within the binding cleft are particular amino acid residues that interact with the phosphate backbone of DNA. The phosphate backbone constitutes a uniform interaction platform, e.g., nucleobase independent, and interactions with the phosphate backbone are altered in polymerases of the present invention, e.g., utilizing the negative charge of the backbone. For example, the interaction between a polymerase of the invention and the phosphate backbone of DNA can be enhanced by substituting neutral or negatively charged amino acids in the binding cleft with positively charged residues. However, mutations that delay polymerase translocation are not limited to this region of the polymerase. Relative to a wild-type Φ29 DNA polymerase, polymerase modifications of the present invention can include, e.g., any of the following mutations or combination of the following mutations: Asp570Lys; Asp570Ala; Asn313Lys; Asn313Ala; Gln303Lys; Gln303Ala; Gly532Ser; Met533delet; Cys530delet; Met533delet and Cys530delet; Gly532delet; Ala531Gly; Gly532Ser; Thr573Lys; Thr573Ala; Asn396Lys; Thr571Lys; Thr571Ala; Thr534Lys; Thr534Ala; Asp535Lys; Asp534Ala; Lys529Ala; and Lys529Asn. For the purposes of the present application, a mutation that includes a deletion at a particular residue position is presented by the amino acid abbreviation, followed by the residue position, followed by "del". Thus, for example, the Met533delet mutation presented above will be understood to mean a mutant polymerase in which the methionine at position 533 has been deleted.

The translocation delay exhibited by modified polymerases of the present invention, e.g., a modified Φ29 polymerase or a modified Φ29-type polymerase, can be greater than the translocation delay exhibited by the parental polymerase or, e.g., about 2.5× greater, about 5× greater, about 10× greater, about 15× greater, about 50× greater or about 100× or more greater, as compared to a parental polymerase (e.g., a wild type Φ29 polymerase) under the standard conditions described above.

As will be appreciated, the above-identified modified or recombinant polymerases that display delayed translocation may optionally include additional modifications that confer other useful properties described herein, e.g., increased branching fraction, increased nucleotide analog residence time and/or increased processivity, etc. As will also be appreciated, the above-identified modified or recombinant polymerases that display delayed translocation can be used in combination with any other embodiments described herein, including: (1) reaction conditions that increase the frequency of branching fraction nonincorporation events; (2) modified recombinant polymerases that exhibit increased branching fractions as compared to the corresponding wild-type polymerases; (3) iterative sampling of unincorporatable nucleotides; (4) two slow-step enzyme systems; (5) detection of noncognate branching events; (6) modified recombinant polymerases that exhibit increased nucleotide residence time; (7) sequencing of nucleic acid templates using more than one mode; and/or (8) any other combination of embodiments described herein.

IV. Increases Residence Time

The present invention also provides modified recombinant polymerases that exhibit increased nucleotide or nucleotide analog residence time at an active site of the polymerase. During SMS, a number of signal parameters may be and generally are used for pulse identification. Two primary parameters are pulse intensity and pulse width, where pulse width relates to the duration of a signal pulse as detected by a signal detector of the sequencing system. Signal pulses that exhibit a short pulse width can arise from undesirable sources during SMS, e.g., transient pulses from labeled analogs in the reaction region that are not involved in an incorporation event. Incorporation events, on the other hand, are generally characterized by longer pulse durations stemming from increased residence time of the labeled nucleotide in the observation region by virtue of it being complexed with the polymerase.

Notwithstanding the differences in residence time duration upon incorporation, in some cases it would be desirable to further increase residence time for incorporated nucleotides, in order to further enhance the distinction between incorporation and transient signal events.

The modified recombinant polymerases of the present invention improve the accuracy of template-dependent polymerization reactions by increasing the residence times of nucleotides or nucleotide analogs at an active site of the polymerase, thereby producing signal pulses of increased width to further facilitate identification as signal pulses resulting from incorporation events.

As noted above, signal pulse intensity and width are primary parameters for signal pulse identification during template-dependent polymerization reactions, e.g., SMS utilizing dye-labeled nucleotide analogs. The signal pulse width is largely determined by the residence time of the nucleotide analog at the active site of the polymerase during the nucleotide incorporation step of the polymerase kinetic cycle. Insufficient residence times produce signal pulses of short duration and, accordingly, narrow pulse width that can prevent detection of genuine nucleotide incorporation events by a signal detector of the sequencing system. Undetected incorporation events arising from insufficient residence time and, accordingly, signal pulse width, constitute sequencing errors that diminish the reliability of SMS results.

The present invention provides modified or recombinant polymerases that improve sequence read accuracy by increasing the residence time of a nucleotide analog at the polymerase active site. During the polymerase kinetic cycle, interaction between a DNA polymerase and a nucleotide or nucleotide analog induces a conformational change in the polymerase, referred to herein as polymerase isomerization. During polymerase isomerization, the nucleotide or nucleotide analog is effectively immobilized at the active site of the polymerase. The duration of the isomerization step, therefore, affects the residence time of the nucleotide analog at the polymerase active site, and, accordingly, affects the signal pulse width as detected by a signal detector of a sequencing system. A slow isomerization step, therefore, can increase signal pulse width and enhance the accuracy of applications such as SMS. Further details regarding DNA polymerase enzymes and/or nucleotides or nucleotide analogs that provide altered residence times for enhanced nucleic acid sequence analysis and determination can be found in Rank et al. U.S. application Ser. No. 11/977,160 POLYMERASE ENZYMES AND REAGENTS FOR ENHANCED NUCELIC ACID SEQUENCING, incorporated herein by reference in its entirety for all purposes.

Completion of the nucleotide or nucleotide analog incorporation step of the DNA polymerase kinetic cycle requires dissociation of the polymerase from the incorporating nucleotide. Until dissociation occurs, the nucleotide, e.g., a dye-labeled nucleotide analog, is effectively immobilized at the active site of the polymerase. Slowing the dissociation step, therefore, results in increased nucleotide residence time at the active site of the polymerase and increases the duration of a signal pulse emitted by a dye-labeled nucleotide analog as it is incorporated into the copy nucleic acid.

Polymerases of the present invention increase the residence time of nucleotides or nucleotide analogs by slowing the isomerization and/or dissociation steps of the polymerase kinetic cycle. Accordingly, these polymerases facilitate signal pulse detection by increasing signal pulse width. For example, a polymerase provided by the present invention comprises the amino acid substitution T368P and exhibits an average nucleotide residence time that is about 2× greater as compared to the residence time of a wild-type parental polymerase under identical conditions.

The nucleotide or nucleotide analog residence time exhibited by modified polymerases of the present invention, e.g., a modified Φ29 polymerase or a modified Φ29-type polymerase, can be greater than the residence time exhibited by the parental polymerase or, e.g., about 1.5× greater, about 2.0× greater or about 3.0× or more greater, under the standard conditions described above.

As will be appreciated, the above-identified modified or recombinant polymerases that display increased nucleotide or nucleotide analog residence time may optionally include additional modifications that confer other useful properties described herein, e.g., increased branching fraction, delayed translocation and/or increased processivity. As will also be appreciated, the above-identified modified or recombinant polymerases that display increased nucleotide or nucleotide analog residence time can be used in combination with any other embodiments described herein, including: (1) reaction conditions that increase the frequency of branching fraction nonincorporation events; (2) modified recombinant polymerases that exhibit increased branching fractions as compared to the corresponding wild-type polymerases; (3) iterative sampling of unincorporatable nucleotides; (4) two slow-step enzyme systems; (5) detection of noncognate branching events; (6) modified recombinant polymerases that exhibit altered translocation properties as compared to the corresponding wild-type polymerases; (7) sequencing of nucleic acid templates using more than one mode; and/or (8) any other combination of embodiments described herein.

The properties of increased branching rates, delayed translocation and increased nucleotide or nucleotide analog residence time are particularly useful in the context of an incorporation of labeled nucleotides by the polymerase, e.g., as detected during sequencing by incorporation methods (including, e.g., SMS methods). For example, the invention provides, e.g., compositions that include one or more engineered or modified polymerase enzymes optionally with one or more template DNAs, and/or labeled or otherwise modified nucleotides or nucleotide analogs, where the composition exhibits increased branching rates and/or delayed polymerase translocation during template dependent polymerase-mediated nucleic acid synthesis. Methods, including SMS using these compositions, are also provided, as are general methods of making polymerases having the properties noted herein.

Accordingly, among other aspects, the present invention provides new polymerases that incorporate nucleotide analogs, such as phosphate labeled analogs, into a growing template copy during DNA amplification. These polymerases are modified such that they have increased branching rates and/or delayed translocation and/or increased residence time when incorporating the relevant analogs, and optionally have improved DNA-polymerase processivity as compared to corresponding wild-type parental polymerases (e.g., polymerases from which modified recombinant polymerases of the invention were derived, e.g., by mutation).

These new polymerases and reaction conditions are particularly well suited to DNA amplification and/or sequencing applications, particularly sequencing protocols that include detection in real time of the incorporation of labeled analogs into DNA amplicons, because the increased branching rate, delayed translocation and/or nucleotide residence time facilitates the correct determination of which labeled nucleotide is incorporated at a site during a template dependent polymerization reaction.

Further Details Regarding Systems for Sequencing by Incorporation

One example of a system for use in the present invention is illustrated in FIG. 1. As shown, system 100 includes substrate 102 of the invention, e.g., upon which sequencing reactions are performed. Optical energy source 104 and additional optical energy source 106 deliver excitation light to the substrate 102, via an optical train. As shown, the optical train includes a dichroic mirror 108 that is transmissive to excitation wavelength of the light from laser 104, while being reflective of light of the wavelength produced by laser 106, allowing both illumination beams to be in the same path. The excitation light is then directed at a second dichroic mirror 110, that reflects the excitation light through objective lens 112, and onto the substrate 102. Optical signals from the substrate 102 are then collected by objective lens 112, and are passed through dichroic 110. The fluorescent signals are then subjected to spatial separation using, e.g., a dispersive optical element, such as an optical grating or prism 114. The separated signals are then focused upon array detector 116, e.g., an EMCCD. The detector, is then operatively coupled to a data storage and processing system, such as computer 118 for processing and storage of the signal data and presentation of the data in a user desired format, e.g., on printer 120. The processing system of the computer is capable of interpreting multiple, e.g., redundant, or iterative signal pulses for each nucleotide incorporation event during a sequencing reaction to call bases with increased accuracy. Although illustrated as an optical train that is transmissive of fluorescent signals, e.g., as provided by dichroic 110, it will be appreciated that fluorescence reflective systems may also be employed. Further details regarding base calling during sequencing by incorporation methods are found in Tomaney et al. PCT Application Serial No. PCT/US2008/065996 METHODS AND PROCESSES FOR CALLING BASES IN SEQUENCING BY INCORPORATION METHODS, incorporated herein by reference in its entirety for all purposes.

As will be appreciated, a number of other components may be included in the systems described herein, including optical filters for filtering background illumination or bleed-through illumination from the light sources, from the actual optical signals. Additionally, alternate optical trains may employ cascaded spectral filters in separating different spectral signal components. A monitor of the computer can display optical signal pulse patterns 122 generated under the conditions provided by the invention, e.g., increased branching, delayed polymerase translocation or increased nucleotide analog residence time. A variety of other optical configurations may additionally be employed in conjunction with the compositions of the invention.

In the context of nucleic acid sequencing methods, it will be appreciated that the signal sources each represent sequencing reactions, and particularly, polymerase-mediated, template-dependent primer extension reactions, where in preferred aspects, each base incorporation event results in a prolonged illumination (or localization) of one of four differentially labeled nucleotides being incorporated, so as to yield a recognizable pulse or signature that carries a distinguishable spectral profile or color.

In the context of the present invention, a signal event is first classified as to whether it constitutes a significant signal pulse or signature based upon whether such signal event meets any of a number of different criteria. Once identified or classified as a significant pulse or signature, the signal pulse or signature may be further assessed to determine whether the signal pulse or signature constitutes an incorporation event and may be called as a particular incorporated base. As will be appreciated, the basis for calling a particular signal event as a significant pulse or signature, and ultimately as an incorporation event, will be subject to a certain amount of error, based upon a variety of parameters as generally set forth herein. The reaction conditions and modified recombinant polymerases of the present invention diminish the error associated with base calling.

Once a particular signal is identified as a significant pulse or signature and is assigned a particular spectrum, e.g. color, the spectrally assigned pulse may be further assessed to determine whether the pulse or signature can be called an incorporation event and, as a result, call the base incorporated in the nascent strand, or its complement in the template sequence. Calling of bases from color assigned pulse or signature data will typically employ tests that identify the confidence level with which a base is called. Typically, such tests will take into account the data environment in which a signal was received, including a number of the same data parameters used in identifying significant pulses, etc. For example, such tests may include considerations of background signal levels, adjacent pulse signal parameters (spacing, intensity, duration, etc.), spectral image resolution, and a variety of other parameters. Such data may be used to assign a score to a given base call for a color assigned signal pulse or signature, where such scores are correlative of a probability that the base called is incorrect, e.g., 1 in 100 (99% accurate), 1 in 1000 (99.9% accurate), 1 in 10,000 (99.99% accurate), 1 in 100,000 (99,999% accurate), or even greater.

Once a base is called with sufficient accuracy, subsequent bases called in the same sequencing run, and in the same primer extension reaction, may then be appended to each previously called base to provide a sequence of bases in the overall sequence of the template or nascent strand. Iterative processing and further data processing, as described in greater detail below, can be used to fill in any blanks, correct any erroneously called bases, or the like for a given sequence.

Polymerases and Nucleotide Analogs

Various polymerases may be used in the methods, compositions and systems described herein, including DNA polymerases, RNA polymerases, reverse transcriptases, and mutant or altered forms of any of the foregoing.

DNA polymerases that can be modified to increase the average branching fraction, decrease the translocation rate or increase nucleotide residence time are generally available. DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J. Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

DNA polymerases and their properties are described in detail in, among other places, DNA Replication $2^{nd}$ Edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9.degree. Nm™ DNA polymerase (New England Biolabs), Stoffel fragment, ThermoSequenase® (Amersham Pharmacia Biotech UK), Terminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J Biol. Chem. 256:3112), and archaeal DP11/DP2 DNA polymerase II (Cann et al., 1998, Proc Natl Acad. Sci. USA 95:14250-5).

Reverse transcriptases useful in the invention include, but are not limited to, reverse transcriptases from HIV, HTLV-1, HTLV-II, FeLV, Fly, SIV, AMV, MMTV, MoMuLV and other retroviruses (see Levin, Cell 88:5-8 (1997); Verma, Biochim Biophys Acta. 473:1-38 (1977); Wu et al., CRC Crit Rev Biochem. 3:289-347 (1975)).

In preferred embodiments, the polymerases employed during the sequencing processes, and optionally during pre-sequencing synthesis, will typically possess strand-displacement activity to displace any primers downstream of the primer at which the strand synthesis is initiated. A preferred rolling circle polymerase exhibits strand-displacement activity, and as such, a single circular template can be sequenced repeatedly to produce a sequence read comprising multiple copies of the complement of the template strand by displacing the nascent strand ahead of the translocating polymerase. Non-limiting examples of rolling circle polymerases suitable for the present invention include but are not limited to T5 DNA polymerase, T4 DNA polymerase holoenzyme, phage M2 DNA polymerase, phage PRD1 DNA polymerase, Klenow fragment of DNA polymerase, and certain polymerases that are modified or unmodified and chosen or derived from the phages Φ29, PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. In certain preferred embodiments, the polymerase is a modified Phi29 DNA polymerase, e.g., as described in U.S. Patent Publication No. 20080108082, incorporated herein by reference in its entirety for all purposes. Similarly, polymerases having enhanced activity for labeled nucleotides are also desirable. Examples of polymerase enzymes for use in various aspects of the invention include, e.g., those described in U.S. patent application Ser. No. 11/645,125, filed Dec. 21, 2006; Ser. No. 11/645,135, filed Dec. 21, 2006; Ser. No. 12/384,112, filed Mar. 30, 2009; 61/094,843, filed Sep. 5, 2008; and 61/072,645, filed Mar. 31, 2008; as well as U.S. Patent Publication No. 20070196846 (the full disclosures of which are incorporated herein by reference in their entireties for all purposes), such as the E375Y/K512Y/T368F mutant polymerase described in the foregoing.

In addition to wild-type polymerases, chimeric polymerases made from a mosaic of different sources can be used. For example, Φ29 polymerases made taking sequences from more than one parental polymerase into account can be used as a starting point for mutating the polymerases of the invention. This can done using consideration of similarity regions between the polymerases to define consensus sequences that are used in the chimera, or can be done using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" *Nature* 391:288-291; Clackson et al. (1991) "Making antibody fragments using phage display libraries" *Nature* 352:624-628; Gibbs et al. (2001) "Degenerate oligonucleotide gene shuffling (DOGS): a method for enhancing the frequency of recombination with family shuffling" *Gene* 271:13-20; and Hiraga and Arnold (2003) "General method for sequence-independent site-directed chimeragenesis: *J. Mol. Biol.* 330: 287-296). In these methods, the recombination points can be predetermined such that the gene fragments assemble in the correct order. However, the combinations, e.g., chimeras, can be formed at random. For example, using methods described in Clarkson, et al., 5 gene chimeras, e.g., comprising segments of a Phi29 polymerase, a PZA polymerase, a M2 polymerase, a B103 polymerase, and a GA-1 polymerase, with improved branching fractions can be generated.

Available DNA polymerase enzymes have also been modified in any of a variety of ways, e.g., to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOG INCORPORATION by Hanzel et al., and PCT/US2007/022459 POLYMERASE ENZYMES AND REAGENTS FOR ENHANCED NUCLEIC ACID SEQUENCING by Rank et al.) and to improve surface-immobilized enzyme activities (e.g., WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to increase the average branching fraction, delay translocation and/or increase nucleotide or nucleotide analog residence time.

The polymerase mutations and mutational strategies noted herein can be combined with available mutations and mutational strategies to confer additional improvements in, e.g., nucleotide analog specificity, enzyme processivity and the like. For example, the mutations and mutational strategies herein can be combined with those taught in, e.g., WO 2007/076057 POLYMERASES FOR NUCLEOTIDE ANALOG INCORPORATION by Hanzel et al., and PCT/US2007/022459 POLYMERASE ENZYMES AND REAGENTS FOR ENHANCED NUCLEIC ACID SEQUENCING by Rank et al. This combination of mutations/mutational strategies can be used to impart several simultaneous improvements to a polymerase (decreased branch fraction formation, improved specificity, improved processivity, improved retention time, improved stability of the closed complex, etc.). In addition, polymerases can be further modified for application-specific reasons, such as to improve activity of the enzyme when bound to a surface, as taught, e.g., in WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art.

Specific mutations noted herein can be used alone or in combination with each other and/or with available mutations as described in the references noted above, or can be used in polymerases that lack such previously described mutations.

Many such polymerases that are suitable for modification are available, e.g., for use in sequencing, labeling and amplification technologies. For example, Human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to increase branch rates and/or decrease translocation rate include Taq polymerases, E. coli DNA Polymerase 1, Klenow fragment, reverse transcriptases, b29 related polymerases including wild type Φ29 polymerase and derivatives of such polymerases such as exonuclease altered forms, T7 DNA polymerase, T5 DNA polymerase, an RB69 polymerase, etc.

In one aspect, the modified recombinant polymerases that exhibit increased branching fractions, delayed translocation and/or increased nucleotide or nucleotide analog residence time are Φ29-type DNA polymerases. For example, the modified recombinant DNA polymerases can be homologous to a wild-type Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287.

As discussed, various polymerases of the invention can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

Nucleotide analogs can also be modified to achieve any of the improved properties desired. For example, various linkers or other substituents can be incorporated into analogs that have the effect of altering the branching rate, residence time or improving processivity. Modifications to the analogs can include extending the phosphate chains, e.g., to include a hexa- or heptaphosphate group, and/or adding chemical linkers to extend the distance between the nucleotide base and the dye molecule, e.g., fluorescent dye molecule. As described in detail herein, modifications to the analogs can include altering the analog such that the analog is unincorporatable. For example, nucleotide analogs of the invention can possess unhydrolyzable groups within the phosphate chain, such that the phosphoester linkage between the analog and the primer strand cannot be formed.

Many nucleotide analogs are available and can be incorporated by the polymerases of the invention. These include analog structures with core similarity to naturally occurring nucleotides, such as those that comprise one or more substituents on a phosphate, sugar or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in U.S. patent application Ser. No. 11/241,809, filed Sep. 29, 2005, and incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

Nucleotide analogs of the present invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc. and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Additional details regarding analogs and methods of making such analogs can be found in U.S. patent application Ser. No. 11/241,809, filed Sep. 29, 2005, and incorporated herein by reference in its entirety for all purposes.

Thus, in one illustrative example, the analog can be a phosphate analog (e.g., an analog that has more than the typical number of phosphates found in nucleoside triphosphates) that include, e.g., an Alexa dye label. For example, an Alexa488 dye can be labeled on a delta phosphate of a tetraphosphate analog (denoted, e.g., A488dC4P or A488dA4P, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled tetraphosphate analog of T), or an Alexa546 dye can be used (e.g., A546dG4P), or an Alexa594 dye can be used (e.g., A594dT4P). An Alexa555 dye (A555dC6P), an Alexa 647 dye (A647d6GP) and/or an Alexa660 dye (A660dA6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

Polymerases of the invention that exhibit branching phenotypes will display a branching fraction that is particular to the nucleotide analog included in the polymerization reaction. For example, a polymerase of the invention may exhibit different branching fractions for A488dC4P than A488dC6P due, e.g., to the size differences between 4P and 6P analogs. It will be appreciated that polymerases of the present invention can be modified such that it exhibits the desired branching fraction for a particular nucleotide analog, e.g., a dye-labeled nucleotide analog with a particular number of phosphate groups.

Applications for Enhanced Nucleic Acid Sequencing

Polymerases of the invention, e.g., modified recombinant polymerases, are used in combination with nucleotides and/or nucleotide analogs, and nucleic acid templates (DNA or RNA) to copy the template nucleic acid. That is, a mixture of the polymerase, nucleotides/analogs, and optionally and other appropriate reagents, the template and a replication initiating moiety (e.g., primer) is reacted such that the polymerase synthesizes nucleic acid (e.g., extends the primer) in a template-dependent manner. The replication initiating moiety can be a standard oligonucleotide primer, or, alternatively, a component of the template, e.g., the template can be a self-priming single stranded DNA, a nicked double stranded DNA, or the like. Similarly, a terminal protein can serve as a initiating moiety. At least one nucleotide analog can be incorporated into the DNA. The template DNA can be a linear or circular DNA, and in certain applications, is desirably a circular template (e.g., for rolling circle replication or for sequencing of circular templates). Optionally, the composition can be present in an automated DNA replication and/or sequencing system.

Incorporation of labeled nucleotide analogs by the polymerases of the invention is particularly useful in a variety of different nucleic acid analyses, including real-time monitoring of DNA polymerization. The label can itself be incorporated, or more preferably, can be released during incorporation of the analog. For example, analog incorporation can be monitored in real-time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. In a preferred aspect, such small observation volumes are provided by immobilizing the polymerase enzyme within a structural confinement, such as a nanohole (an aperture of less than 1 μM diameter through which a synthesis complex can be illuminated by optical energy) (See, e.g., co-pending Published U.S. Patent Application No. 2007-0188750, and published International Patent Application No. WO 2007/095119, the full disclosures of which are incorporated herein by reference in their entirety for all purposes) or nanoholes that additionally provide optical confinement, such as a zero-mode waveguide (ZMW). For a description of ZMWs and their application in single molecule analyses, and particularly nucleic acid sequencing, see, e.g., U.S. Patent Application Publication No. 2003/0044781, and U.S. Pat. No. 6,917,726, each of which is incorporated herein by reference in its entirety for all purposes. See also Levene et al. (2003) "Zero-mode waveguides for single-molecule analysis at high concentrations" Science 299:682-686 and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the $\alpha$ and $\beta$ phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a nanohole or zero mode waveguide.

In addition to their use in sequencing, the polymerases and/or reaction conditions of the invention are also useful in a variety of other genotyping analyses, e.g., SNP genotyping using single base extension methods, real time monitoring of amplification, e.g., RT-PCR methods, and the like. Further details regarding sequencing and nucleic acid amplification can be found, e.g., in Sambrook et al., *Molecular Cloning—A Laboratory Manual* (3rd Ed.), Vol. 1-3, Cold Spring Harbor Laboratory, Cold Spring Harbor, N.Y., 2000; *Current Protocols in Molecular Biology*, F. M. Ausubel et al., eds., Current Protocols, a joint venture between Greene Publishing Associates, Inc. and John Wiley & Sons, Inc., (supplemented through 2006); and *PCR Protocols: A Guide to Methods and Applications* (Innis et al. eds) Academic Press Inc. San Diego, Calif. (1990).

Molecular Modeling-Based Modification of Polymerases to Increase Branching Fraction, Delay Translocation or Increase Nucleotide Analog Retention Time Structure-Based Design of Recombinant Polymerases Structural data for a polymerase can be used to conveniently identify amino acid residues as candidates for mutagenesis to create recombinant polymerases, e.g., having modified active site regions that increase the branching fractions. For example, analysis of the three dimensional structure of a polymerase such as Φ29 can identify residues that are particularly relevant to branching, translocation and/or nucleotide residence time properties of the polymerase.

The three-dimensional structures of a large number of DNA polymerases have been determined by x-ray crystallography and nuclear magnetic resonance (NMR) spectroscopy, including the structures of polymerases with bound templates, nucleotides, and/or nucleotide analogs. Many such structures are freely available for download from the Protein Data Bank, at (www(dot)rcsb(dot)org/pdb. Structures, along with domain and homology information, are also freely available for search and download from the National Center for Biotechnology Information's Molecular Modeling Data-Base, at www(dot)ncbi(dot)nlm(dot)nih(dot)gov/Structure/MMDB/mmdb(dot)shtml. The structures of additional polymerases can be modeled, for example, based on homology of the polymerases with polymerases whose structures have already been determined. Alternatively, the structure of a given polymerase, optionally complexed with a template and/or nucleotide analog, or the like, can be determined.

Techniques for crystal structure determination are well known. See, for example, McPherson (1999) *Crystallization of Biological Macromolecules* Cold Spring Harbor Laboratory; Bergfors (1999) *Protein Crystallization* International University Line; Mullin (1993) *Crystallization* Butterwoth-Heinemann; Stout and Jensen (1989) *X-ray structure determination: a practical guide*, 2nd Edition Wiley Publishers, New York; Ladd and Palmer (1993) *Structure determination by X-ray crystallography*, 3rd Edition Plenum Press, New York; Blundell and Johnson (1976) *Protein Crystallography* Academic Press, New York; Glusker and Trueblood (1985) *Crystal structure analysis: A primer*, 2nd Ed. Oxford University Press, New York; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography, Second Edition* Academic Press; Drenth (1999) *Principles of Protein X-Ray Crystallography* (Springer Advanced Texts in Chemistry) Springer-Verlag; Fanchon and Hendrickson (1991) Chapter 15 of *Crystallographic Computing, Volume 5* IUCr/Oxford University Press; Murthy (1996) Chapter 5 of *Crystallographic Methods and Protocols* Humana Press; Dauter et al. (2000) "Novel approach to phasing proteins: derivatization by short cryo-soaking with halides" Acta Cryst. D 56:232-237; Dauter (2002) "New approaches to high-throughput phasing" Curr. Opin. Structural Biol. 12:674-678; Chen et al. (1991) "Crystal structure of a bovine neurophysin-II dipeptide complex at 2.8 Å determined from the single-wavelength anomalous scattering signal of an incorporated iodine atom" Proc. Natl Mad. Sci. USA, 88:4240-4244; and Gavira et al. (2002) "Ab initio crystallographic structure determination of insulin from protein to electron density without crystal handling" Acta Cryst. D 58:1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276: 307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), PRODRG (van Aalten et al. (1996) "PRODRG, a program for generating molecular topologies and unique molecular descriptors from coordinates of small molecules" J Comput Aided Mol Des 10:255-262), and O (Jones et al. (1991) "Improved methods for building protein models in electron density maps and the location of errors in these models" Acta Crystallogr A 47 (Pt 2):110-119).

Techniques for structure determination by NMR spectroscopy are similarly well described in the literature. See, e.g., Cavanagh et al. (1995) *Protein NMR Spectroscopy: Principles and Practice*, Academic Press; Levitt (2001) *Spin Dynamics: Basics of Nuclear Magnetic Resonance*, John Wiley & Sons; Evans (1995) *Biomolecular NMR Spectroscopy*, Oxford University Press; Wüthrich (1986) *NMR of Proteins and Nucleic Acids* (Baker Lecture Series), Kurt Wiley-Interscience; Neuhaus and Williamson (2000) *The Nuclear Overhauser Effect in Structural and Conformational Analysis*, 2nd Edition, Wiley-VCH; Macomber (1998) *A Complete Introduction to Modern NMR Spectroscopy*, Wiley-Interscience; Downing (2004) *Protein NMR Techniques* (Methods in Molecular Biology), 2nd edition, Humana Press; Clore and Gronenborn (1994) *NMR of Proteins* (Topics in Molecular and Structural Biology), CRC Press; Reid (1997) *Protein NMR Techniques*, Humana Press; Krishna and Berliner (2003) *Protein NMR for the Millenium* (Biological Magnetic Resonance), Kluwer Academic Publishers; Kiihne and De Groot (2001) *Perspectives on Solid State NMR in Biology* (Focus on Structural Biology, 1), Kluwer Academic Publishers; Jones et al. (1993) *Spectroscopic Methods and Analyses: NMR, Mass Spectrometry, and Related Techniques* (Methods in Molecular Biology, Vol. 17), Humana Press; Goto and Kay (2000) Curr. Opin. Struct. Biol. 10:585; Gardner (1998) Annu. Rev. Biophys. Biomol. Struct. 27:357; Wüthrich (2003) Angew. Chem. Int. Ed. 42:3340; Bax (1994) Curr. Opin. Struct. Biol. 4:738; Pervushin et al. (1997) Proc. Natl. Acad. Sci. U.S.A. 94:12366; Fiaux et al. (2002) Nature 418: 207; Fernandez and Wider (2003) Curr. Opin. Struct. Biol. 13:570; Ellman et al. (1992) J. Am. Chem. Soc. 114:7959; Wider (2000) BioTechniques 29:1278-1294; Pellecchia et al. (2002) Nature Rev. Drug Discov. (2002) 1:211-219; Arora and Tamm (2001) Curr. Opin. Struct. Biol. 11:540-547; Flaux et al. (2002) Nature 418:207-211; Pellecchia et al. (2001) J. Am. Chem. Soc. 123:4633-4634; and Pervushin et al. (1997) Proc. Natl. Acad. Sci. USA 94:12366-12371.

The structure of a polymerase, or polymerase bound to a DNA or with a given nucleotide analog incorporated into the active site can, as noted, be directly determined, e.g., by x-ray crystallography or NMR spectroscopy, or the structure can be modeled based on the structure of the polymerase and/or a structure of a polymerase with a natural nucleotide bound. The active site or other relevant domain of the polymerase can be identified, for example, by homology with other polymerases, examination of polymerase-template or polymerase-nucleotide co-complexes, biochemical analysis of mutant polymerases, and/or the like. The position of a nucleotide analog (as opposed to an available nucleotide structure) in the active site can be modeled, for example, by projecting the location of non-natural features of the analog (e.g., additional phosphate or phosphonate groups in the phosphorus containing chain linked to the nucleotide, e.g., tetra, penta or hexa phosphate groups, detectable labeling groups, e.g., fluorescent dyes, or the like) based on the previously determined location of another nucleotide or nucleotide analog in the active site.

Such modeling of the nucleotide analog or template (or both) in the active site can involve simple visual inspection of a model of the polymerase, for example, using molecular graphics software such as the PyMOL viewer (open source, freely available on the World Wide Web at www(dot)pymol (dot)org) or Insight II (commercially available from Accelrys at (www (dot) accelrys (dot) com/products/insight). Alternatively, modeling of the active site complex of the polymerase or a putative mutant polymerase, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" Drug Discov. Today 7:1047-1055; Molecular Modeling for Beginners, at (www (dot) usm (dot) maine (dot) edu/~rhodes/SPVTut/ index (dot) html; and Methods for Protein Simulations and Drug Design at (www (dot) dddc (dot) ac (dot) cn/embo04; and references therein. Software to facilitate such modeling is widely available, for example, the CHARMm simulation package, available academically from Harvard University or commercially from Accelrys (at www (dot) accelrys (dot) corn), the Discover simulation package (included in Insight II, supra), and Dynama (available at (www(dot) cs (dot) gsu (dot) edu/~cscrwh/progs/progs (dot) html). See also an extensive list of modeling software at (www (dot) netsci (dot) org/Resources/Software/Modeling/MMMD/top (dot) html.

Visual inspection and/or computational analysis of a polymerase model can identify relevant features of the active site or other domain, including, for example, amino acid residues of domains that are in close proximity to one another (to stabilize inter-domain interactions) residues in the active site that interact with the nucleotide or analog, or that modulate how large a binding pocket for the analog is relative to the analog. That is, inter-domain amino acid contacts can stabilize the closed complex, and/or the size or composition (e.g., position of charged or hydrophobic residues) of the binding pocket in the active site can control entry and release of the nucleotide, which can affect branching rate. A residue can, for example, be deleted or replaced with a residue having a different (smaller, larger, ionic, non-ionic, etc.) side chain. Similarly, residues that can be altered to introduce desirable interactions with the nucleotide analog can be identified to reduce branching. Such a residue can be replaced with a residue that is complementary with, e.g., a non-natural feature of the analog, for example, with a residue that can hydrogen bond to the analog (e.g., serine, threonine, histidine, asparagine, or glutamine), a hydrophobic residue that can interact with a hydrophobic group on the analog, an aromatic residue that can provide favorable hydrophobic interactions with a group on the analog (e.g., a fluorophore), an aromatic residue that can engage in a π-π or edge-face stacking interaction with an aromatic group in the analog, a residue that can engage in a cation-π interaction with the analog, or a charged residue (e.g., aspartic or glutamic acid, or lysine, arginine, or histidine) that can electrostatically interact with an oppositely charged moiety on the analog (e.g., an additional phosphate group).

Thus, in addition to methods of using the polymerases and other compositions herein, the present invention also includes methods of making the polymerases. As described, methods of making a recombinant DNA polymerase can include structurally modeling a first polymerase, e.g., using any available crystal structure and molecular modeling software or system. Based on the modeling, one or more feature affecting closed complex stability, or nucleotide access or removal to or from the active site (and, thereby, branching) and/or binding of a DNA or nucleotide analog within the active site region is identified. These residues can be, e.g., in the active site, an exonuclease, TPR2 or thumb domain (or interface between domains) or proximal to such domains. The DNA polymerase is mutated to include non-natural residues at such positions, and then screened for an activity of interest.

Mutating Polymerases

Various types of mutagenesis are optionally used in the present invention, e.g., to modify polymerases to produce variants, e.g., in accordance with polymerase models and model predictions as discussed above, or using random or semi-random mutational approaches. In general, any available mutagenesis procedure can be used for making polymerase mutants. Such mutagenesis procedures optionally include selection of mutant nucleic acids and polypeptides for one or more activity of interest (e.g., decreased branch fraction, increased or decreased complex stability, improved processivity, and/or improved $k_{off}$, $K_m$, $V_{max}$, $k_{cat}$ etc., e.g., for a given nucleotide analog). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified e.g., in WO 2007/076057 POLYMERASES FOR NUCLEOTIDE ANALOG INCORPORATION by Hanzel et al.; PCT/US2007/022459 POLYMERASE ENZYMES AND REAGENTS FOR ENHANCED NUCLEIC ACID SEQUENCING; Hanzel et al. WO 2007/075987 ACTIVE SURFACE COUPLED POLYMERASES; and Hanzel et al. WO 2007/076057 PROTEIN ENGINEERING STRATEGIES TO OPTIMIZE ACTIVITY OF SURFACE ATTACHED PROTEINS.

Optionally, mutagenesis can be guided by known information from a naturally occurring polymerase molecule, or of a known altered or mutated polymerase (e.g., using an existing mutant polymerase as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" *Nature* 391:288-291).

Additional information on mutation formats is found in: Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2006) ("Ausubel")) and *PCR Protocols A Guide to Methods and Applications* (Innis et al. eds) Academic Press Inc. San Diego, Calif. (1990) (Innis). The following publications and references cited within provide additional detail on mutation formats: Arnold, *Protein engineering for unusual environments, Current Opinion in Biotechnology* 4:450-455 (1993); Bass et al., *Mutant Trp repressors with new DNA-binding specificities, Science* 242:240-245 (1988); Bordo and Argos (1991) *Suggestions for "safe Residue Substitutions in Site-directed Mutagenesis* 217:721-729; Botstein & Shortie, *Strategies and applications of in vitro mutagenesis, Science* 229:1193-1201(1985); Carter et al., *Improved oligonucleotide site-directed mutagenesis using M13 vectors, Nucl. Acids Res.* 13: 4431-4443 (1985); Carter, *Site-directed mutagenesis, Biochem. J.* 237:1-7 (1986); Carter, *Improved oligonucleotide-directed mutagenesis using M13 vectors, Methods in Enzymol.* 154: 382-403 (1987); Dale et al., *Oligonucleotide-directed random mutagenesis using the phosphorothioate method, Methods Mol. Biol.* 57:369-374 (1996); Eghtedarzadeh & Henikoff, *Use of oligonucleotides to generate large deletions, Nucl. Acids Res.* 14: 5115 (1986); Fritz et al., *Oligonucleotide-directed construction of mutations: a gapped duplex DNA procedure without enzymatic reactions in vitro, Nucl. Acids Res.* 16: 6987-6999 (1988); Grundström et al., *Oligonucleotide-directed mutagenesis by microscale 'shot-gun' gene synthesis, Nucl. Acids Res.* 13: 3305-3316 (1985); Hayes (2002) *Combining Computational and Experimental Screening for rapid Optimization of Protein Properties PNAS* 99(25) 15926-15931; Kunkel, *The efficiency of oligonucleotide directed mutagenesis*, in *Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Point Mismatch Repair, Cell* 38:879-887 (1984); Kramer et al., *Improved enzymatic in vitro reactions in the gapped duplex DNA approach to oligonucleotide-directed construction of mutations, Nucl. Acids Res.* 16: 7207 (1988); Ling et al., *Approaches to DNA mutagenesis: an overview, Anal Biochem.* 254(2): 157-178 (1997); Lorimer and Pastan *Nucleic Acids Res.* 23, 3067-8 (1995); Mandecki, *Oligonucleotide-directed double-strand break repair in plasmids of Escherichia coli: a method for site-specific mutagenesis, Proc. Natl. Acad. Sci. USA*, 83:7177-7181 (1986); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Nambiar et al., *Total synthesis and cloning of a gene coding for the ribonuclease S protein, Science* 223: 1299-1301 (1984); Sakamar and Khorana, *Total synthesis and expression of a gene for the α-subunit of bovine rod outer segment guanine nucleotide-binding protein (transducin), Nucl. Acids Res.* 14: 6361-6372 (1988); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Sieber, et al., *Nature Biotechnology*, 19:456-460 (2001); Smith, *In vitro mutagenesis, Ann. Rev. Genet.* 19:423-462(1985); *Methods in Enzymol.* 100: 468-500 (1983); *Methods in Enzymol.* 154: 329-350 (1987); Stemmer, *Nature* 370, 389-91 (1994); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Wells et al., *Importance of hydrogen-bond formation in stabilizing the transition state of subtilisin, Phil. Trans. R. Soc. Lond. A* 317: 415-423 (1986); Wells et al., *Cassette mutagenesis: an efficient method for generation of multiple mutations at defined sites, Gene* 34:315-323 (1985); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); Zoller & Smith, *Oligonucleotide-directed mutagenesis: a simple method using two oligonucleotide primers and a single-stranded DNA template, Methods in Enzymol.* 154:329-350 (1987); Clackson et al. (1991) "Making antibody fragments using phage display libraries" *Nature* 352:624-628; Gibbs et al. (2001) "Degenerate oligonucleotide gene shuffling (DOGS): a method for enhancing the frequency of recombination with family shuffling" *Gene* 271:13-20; and Hiraga and Arnold (2003) "General method for sequence-independent site-directed chimeragenesis: *J. Mal. Biol.* 330:287-296. Additional details on many of the above methods can be found in *Methods in Enzymology* Volume 154, which also describes useful controls for trouble-shooting problems with various inutagenesis methods.

Determining Kinetic Parameters

The polymerases of the invention can be screened or otherwise tested to determine whether the polymerase displays a modified activity for or with a nucleotide analog or template as compared to the first DNA polymerase (e.g., a corresponding wild-type or available mutant polymerase from which the recombinant polymerase of the invention was derived). For example, branch fraction, $k_{off}$, $k_{cat}$, $K_m$, $V_{max}$, $k_{cat}/K_m$, $V_{max}/K_m$, $k_{pol}$, and/or $K_d$ of the recombinant DNA polymerase for the nucleotide (or analog) or template nucleic acid can be determined. The enzyme perfection metric $k_{cat}/k_m$ is also a useful measure, e.g., for assessing branch rate. $k_{cat}/K_m$ is a measure of substrate binding that leads to product formation (and, thus, includes terms defining binding $K_d$ and inversely predicts branching fraction formation).

As is well-known in the art, for enzymes obeying simple Michaelis-Menten kinetics, kinetic parameters are readily derived from rates of catalysis measured at different substrate concentrations. The Michaelis-Menten equation, $V=V_{max}[S]$ $([S]+K_m)^{-1}$, relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V). Details regarding $K_{off}$ determination are described above. In general, the dissociation rate can be measured in any manner that detects the polymerase/DNA complex over time. This includes stopped flow spectroscopy, or even simply by taking aliquots over time and testing for polymerase activity on the template of interest. Free polymerase is captured with a polymerase trap after dissociation, e.g., by incubation in the presence of heparin or an excess of competitor DNA (e.g., non-specific salmon sperm DNA, or the like).

For many enzymes, $K_m$ is equal to the dissociation constant of the enzyme-substrate complex and is thus a measure of the strength of the enzyme-substrate complex. For such an enzyme, in a comparison of $K_m$s, a lower $K_m$ represents a complex with stronger binding, while a higher Km represents a complex with weaker binding. The ratio $k_{cat}/K_m$, sometimes called the specificity constant, represents the apparent rate constant for combination of substrate with free enzyme. The larger the specificity constant, the more efficient the enzyme is in binding the substrate and converting it to product (this provides an inverse measure of branching rate, as branching rate is the rate at which the enzyme binds substrate (e.g., nucleotide), but does not convert it to product (e.g., a DNA polymer).

$k_{cat}$ (also called the turnover number of the enzyme) can be determined if the total enzyme concentration ($[E_T]$, i.e., the concentration of active sites) is known, since $V_{max}=k_{cat}[E_T]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burk plot of 1/V against 1/[S], where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$. Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others in suitable excess (e.g., effectively constant) concentration typically yields normal Michaelis-Menten kinetics.

In one embodiment, using pre-steady-state kinetics, the nucleotide concentration dependence of the rate $k_{obs}$ (the observed first-order rate constant for dNTP incorporation) provides an estimate of the $K_m$ for a ground state binding and the maximum rate of polymerization ($k_{pol}$). The $k_{obs}$ is measured using a burst assay. The results of the assay are fitted with the Burst equation; Product=A[1−exp(−$k_{obs}$*t)]+$k_{ss}$*t where A represents amplitude an estimate of the concentration of the enzyme active*s, $k_{ss}$ is the observed steady-state rate constant and t is the reaction incubation time. The $K_m$ for dNTP binding to the polymerase-DNA complex and the $k_{pol}$ are calculated by fitting the dNTP concentration dependent change in the $k_{obs}$ using the equation $k_{obs}=(k_{pol}$*[S])*($K_m$+[S])−1 where [S] is the substrate concentration. Results are optionally obtained from a rapid-quench experiment (also called a quench-flow measurement), for example, based on the methods described in Johnson (1986) "Rapid kinetic analysis of mechanochemical adenosinetriphosphatases" Methods Enzymol. 134:677-705, Patel et al. (1991) "Pre-steady-state kinetic analysis of processive DNA replication including complete characterization of an exonuclease-deficient mutant" Biochemistry 30(2):511-25, and Tsai and Johnson (2006) "A new paradigm for DNA polymerase specificity" Biochemistry 45(32):9675-87.

Parameters such as rate of binding of a nucleotide analog or template by the recombinant polymerase, rate of product release by the recombinant polymerase, or branching rate of the recombinant polymerase can also be determined, and optionally compared to that of the first polymerase (e.g., a corresponding wild-type polymerase).

For a more thorough discussion of enzyme kinetics, see, e.g., Berg, Tymoczko, and Stryer (2002) *Biochemistry, Fifth Edition*, W. H. Freeman; Creighton (1984) *Proteins: Structures and Molecular Principles*, W. H. Freeman; and Fersht (1985) *Enzyme Structure and Mechanism, Second Edition*, W. H. Freeman.

In one aspect, the improved property of the enzymes of the invention is measured with reference to a model analog or analog set and compared with a given parental enzyme. For example, in the case of enzymes derived from a Φ29 parental enzyme, where the improvement being sought is a decrease in stability of the closed complex, an improved enzyme of the invention (i.e., an enzyme with an increased branching fraction) would have a higher $k_{off}$ than the parental enzyme, e.g., wild type Φ29. While the foregoing may be used as a characterization tool, it in no way is intended as a specifically limiting reaction of the invention.

Screening Polymerases

Screening or other protocols can be used to determine whether a polymerase displays a modified activity for a nucleotide analog as compared to the first DNA polymerase. For example, $k_{off}$, $k_{cat}$, $K_m$, $V_{max}$, or $k_{cat}/K_m$ of the recombinant DNA polymerase for the template or nucleotide or analog can be determined as discussed above.

In one desirable aspect, a library of recombinant DNA polymerases can be made and screened for these properties. For example, a plurality of members of the library can be made to include one or more mutations that increase branching fractions, delay translocation and/or increase residence time, that are then screened for the properties of interest (e.g., increased branching fraction, delayed translocation or increased residence time). In general, the library can be screened to identify at least one member comprising a modified activity of interest.

Libraries of polymerases can be either physical or logical in nature. Moreover, any of a wide variety of library formats can be used. For example, polymerases can be fixed to solid surfaces in arrays of proteins. Similarly, liquid phase arrays of polymerases (e.g., in microwell plates) can be constructed for convenient high-throughput fluid manipulations of solutions comprising polymerases. Liquid, emulsion, or gel-phase libraries of cells that express recombinant polymerases can also be constructed, e.g., in microwell plates, or on agar plates. Phage display libraries of polymerases or polymerase domains (e.g., including the active site region or interdomain stability regions) can be produced. Likewise, yeast display libraries can be used. Instructions in making and using libraries can be found, e.g., in Sambrook, Ausubel and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. RainDance Technologies' nanodroplet platform provides another method for handling large numbers of spatially separated reactions. Furthermore, the patent and technical literature includes many examples of microfluidic systems which can interface directly with microwell plates for fluid handling.

Desirable Properties

The polymerases of the invention can include any of a variety of modified properties towards natural or nucleotide analogs or analogs, depending on the application, including increased branching fractions, delayed translocation, increased nucleotide or nucleotide analog residence time, greater processivity, etc. For example, branching rates can be directly monitored in high-throughput SMS reactions using known templates. Branching or translocation rates can be screened for or against in selecting a polymerase of the invention, e.g., by screening enzymes based on kinetic or product formation properties. Nucleotide analog residence time is readily determined by observing signal pulse widths as detected by a signal detector of a sequencing system.

For example, improvements in a dissociation rate (or improved processivity) of 30% or more, e.g., about 50%, 75%, or even 100% or more can be screened for in identifying polymerases that display decreased translocation rates. Similarly, detecting mutant polymerases that exhibit branch rates of more than 30%, e.g., 40% or more, preferably 50% or more, or even 75% or more is a feature of the invention.

Affinity Tags and Other Optional Polymerase Features

The recombinant DNA polymerases optionally include additional features exogenous or heterologous to the polymerases. For example, the recombinant polymerases optionally include one or more exogenous affinity tags, e.g., purification or substrate binding tags, such as a GST tag, an HA tag sequence, a plurality of GST tags, a plurality of HA tag sequences, a SNAP-tag, a c-myc tag, a c-myc fusion, or the like. These and other features useful in the context of binding a polymerase to a surface are optionally included, e.g., to orient and/or protect the polymerase active site when the polymerase is bound to a surface. Other useful features include recombinant dimer domains of the enzyme, and, e.g., large extraneous polypeptide domains coupled to the polymerase distal to the active site. For example, for Φ29, the active site is in the C terminal region of the protein, and added surface binding elements (extra domains, GST tags, etc.) are typically located in the N-terminal region to avoid interfering with the active site when the polymerase is coupled to a surface.

In general, surface binding elements and purification tags that can be added to the polymerase (recombinantly or, e.g., chemically) include, e.g., biotin, avidin, GST sequences, modified GST sequences, e.g., that are less likely to form dimers, BiTag sequences, S tags, SNAP-tags, enterokinase sites, thrombin sites, antibodies or antibody domains, antibody fragments, antigens, receptors, receptor domains, receptor fragments, ligands, dyes, acceptors, quenchers, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Additional details on fixing a polymerase to a surface, attaching tags, and the like are found in WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al.

Making and Isolating Recombinant Polymerases

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase of the invention, e.g., a modified polymerase with an increased branching rate, delayed translocation or increased nucleotide analog residence time. Recombinant methods for making nucleic acids, expression and isolation of expressed products are well known and described in the art. For example, when modifying the active site to increase branching properties, features are selected (e.g., by modeling, though random approaches can also be used) that hinder steric access of the nucleotide analog to the active site, and/or that interfere with charge-charge or hydrophobic interactions between a given nucleotide analog and the polymerase target. Methods for making and selecting mutations in the active site of polymerases, including for modifying steric features in or near the active site to permit improved access by nucleotide analogs are found, e.g., in WO 2007/076057 POLYMERASES FOR NUCLEOTIDE ANALOG INCORPORATION by Hanzel et al., and PCT/US2007/022459 POLYMERASE ENZYMES AND REAGENTS FOR ENHANCED NUCLEIC ACID SEQUENCING by Rank et al.

Additional useful references for mutation, recombinant and in vitro nucleic acid manipulation methods (including cloning, expression, PCR, and the like) include Berger and Kimmel, *Guide to Molecular Cloning Techniques, Methods in Enzymology volume* 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley); Chen et al. (ed) *PCR Cloning Protocols, Second Edition* (Methods in Molecular Biology, volume 192) Humana Press; and in Viljoen et al. (2005) *Molecular Diagnostic PCR Handbook* Springer, ISBN 1402034032.

In addition, a plethora of kits are commercially available for the purification of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, Protein Purification, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3$^{rd}$ Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Abuja ed., *Handbook of Bioseparations*, Academic Press (2000).

Nucleic Acid and Polypeptide Sequence and Variants

As described herein, the invention provides polynucleotide sequences encoding, e.g., a polymerase as described herein. Examples of polymerase sequences that include features are found herein, e.g., increased branching fractions as in Table A. However, one of skill in the art will immediately appreciate that the invention is not limited to the specifically exemplified sequences. For example, one of skill will appreciate that the invention also provides, e.g., many related sequences with the functions described herein, e.g., polynucleotides and polypeptides encoding conservative variants of a polymerase of Table A or any other specifically listed polymerase herein. Combinations of any of the mutations noted herein or combinations of any of the mutations herein in combination with those noted in other available references relating to improved polymerases, such as Hanzel et WO 2007/076057 POLYMERASES FOR NUCLEOTIDE ANALOG INCORPORATION; Rank et al. PCT/US2007/022459 POLYMERASE ENZYMES AND REAGENTS FOR ENHANCED NUCLEIC ACID SEQUENCING; Hanzel et al. WO 2007/075987 ACTIVE SURFACE COUPLED POLYMERASES; and Hanzel et al. WO 2007/076057 PROTEIN ENGINEERING STRATEGIES TO OPTIMIZE ACTIVITY OF SURFACE ATTACHED PROTEINS are also features of the invention Accordingly, the invention provides a variety of polypeptides (polymerases) and polynucleotides (nucleic acids that encode polymerases). Example polynucleotides of the invention include, e.g., a polynucleotide encoding a polymerase as set forth in Table A or a polynucleotide that is complementary to or that encodes a polynucleotide sequence thereof (e.g., where the given sequence is a DNA, an RNA is one example of a sequence that encodes the DNA, e.g., via reverse transcription). A polynucleotide of the invention also optionally includes any polynucleotide that encodes a polymerase of Table A. Because of the degeneracy of the genetic code, many polynucleotides equivalently encode a given polymerase sequence. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention (e.g., that specifically recognizes a feature of the polymerase that confers increased branching, delayed translocation or increased nucleotide analog residence time.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant mutational feature (for example, the conservative substitution can be of a residue distal to the active site region, or distal to an interdomain stability region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE C

Conservative Amino Acid Substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention. In addition, target nucleic acids which hybridize to a nucleic acid encoding a polymerase of Table A or any other specifically listed polymerase herein under high, ultra-high and ultra-ultra high stringency conditions, where the nucleic acids encode mutations corresponding to those noted in Table A or other listed polymerases are a feature of the invention. Examples of such nucleic acids include those with one or a few silent or conservative nucleic acid substitutions as compared to a given nucleic acid sequence encoding a polymerase of Table A (or other exemplified polymerase), where any conservative substitutions are for residues other than those noted in Table A or elsewhere as being relevant to a feature of interest (improved complex stability, decreased branch rate formation, etc.).

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in *Current Protocols in Molecular Biology*, Ausubel et al., eds., *Current Protocols*, a joint venture between Greene Publishing Associates, Inc. and John Wiley & Sons, Inc., (supplemented through 2004) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the the/alai melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequence

In some aspects, the invention provides a nucleic acid that comprises a unique subsequence in a nucleic acid that encodes a polymerase of Table A. The unique subsequence may be unique as compared to a nucleic acid corresponding to, e.g., a wild type φ29. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polymerase of Table A. Here, the unique subsequence is unique as compared to, e.g., wild type φ29 or previously characterized mutation thereof.

The invention also provides for target nucleic acids which hybridize under stringent conditions to a unique coding oligonucleotide which encodes a unique subsequence in a polypeptide selected from the sequences of Table A, wherein the unique subsequence is unique as compared to a polypeptide corresponding to wild type φ29. Unique sequences are determined as noted above.

Sequence Comparison, Identity and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLO- SUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Cognate Sampling Kinetics

In some aspects, the invention provides methods for measuring the kinetics of sampling of a nucleotide or nucleotide analog. In some cases, the base in a template nucleic acid can be identified, by cognate sampling. In some cases the nucleotide analog to be identified is not the cognate base, but is close enough in structure, that it will spend enough time associated with the enzyme that the kinetics of its sampling of the active site of the polymerase can be determined. When a primer is hybridized to a nucleic acid, a polymerase enzyme will generally add a cognate nucleotide or nucleotide analog to the 3' growing end of the primer. The cognate nucleotide is the nucleotide or nucleotide analog that is the complement of the next nucleotide in the template nucleic acid to which the primer is hybridized. Before the cognate nucleotide or analog is incorporated, the cognate nucleotide and non-cognate nucleotides can enter the active site of the polymerase. The non-cognate nucleotides or nucleotide analogs will generally bind to the active site for a very short time, and be released. During sequencing, the cognate nucleotide or analog will sometimes sample the polymerase and get released, and will sometimes become incorporated into the growing strand.

We have found that it can be advantageous to observe the interaction of the polymerase and the a cognate nucleotide or analog under conditions where it is unincorporatable into the growing chain. We have found that where a labeled unincorporatable cognate nucleotide and one or more labeled non-cognate nucleotides are present, the signal from the cognate nucleotide can be readily distinguished from that of the non-cognate nucleotide, allowing for the identification of the corresponding base in the template nucleic acid to which the primer is hybridized. In addition, we have found that the time course of the interaction of the cognate nucleic acid or analog under single molecule conditions can provide important information about the components of the reaction including the polymerase, the template, the primer, and/or the nucleotide analogs.

In some embodiments of the invention, a polymerase enzyme complex comprising a polymerase enzyme, a template nucleic acid, and a primer are provided along with one or more labeled nucleotides or nucleotide analogs under conditions wherein they are unincorporable. The polymerase enzyme complex is observed under conditions in which the signal from a nucleotide or nucleotide analog that is associated with the polymerase enzyme can be distinguished from the signal from labeled nucleotides or nucleotide analogs in solution. Methods for this type of selective observation are known in the art. TIRF systems, for example can be used. Arrays of optical confinements such as zero mode waveguides described herein can also be employed. The use of the term unincorporatable in this context means that the nucleotide or nucleotide analog is substantially unincorporatable under the conditions of the system which is being observed. For example, a nucleotide or nucleotide analog can be unincorporatable by virtue of using a primer that terminates at its 3' end with a group that is incapable of extension, such as with a dideoxy nucleotide. Nucleotide analogs which can be added, but not extended are generally referred to as terminators, and many types of terminators are known in the art. In other cases, the primer may be extendable, and the nucleotide or nucleotide analog is modified such that it will not be incorporated. Such unincorporatable nucleotide analogs are described, for example in U.S. patent application Ser. No. 12/370,472, filed Feb. 12, 2009 which is incorporated by references herein for all purposes.

Figure 8:
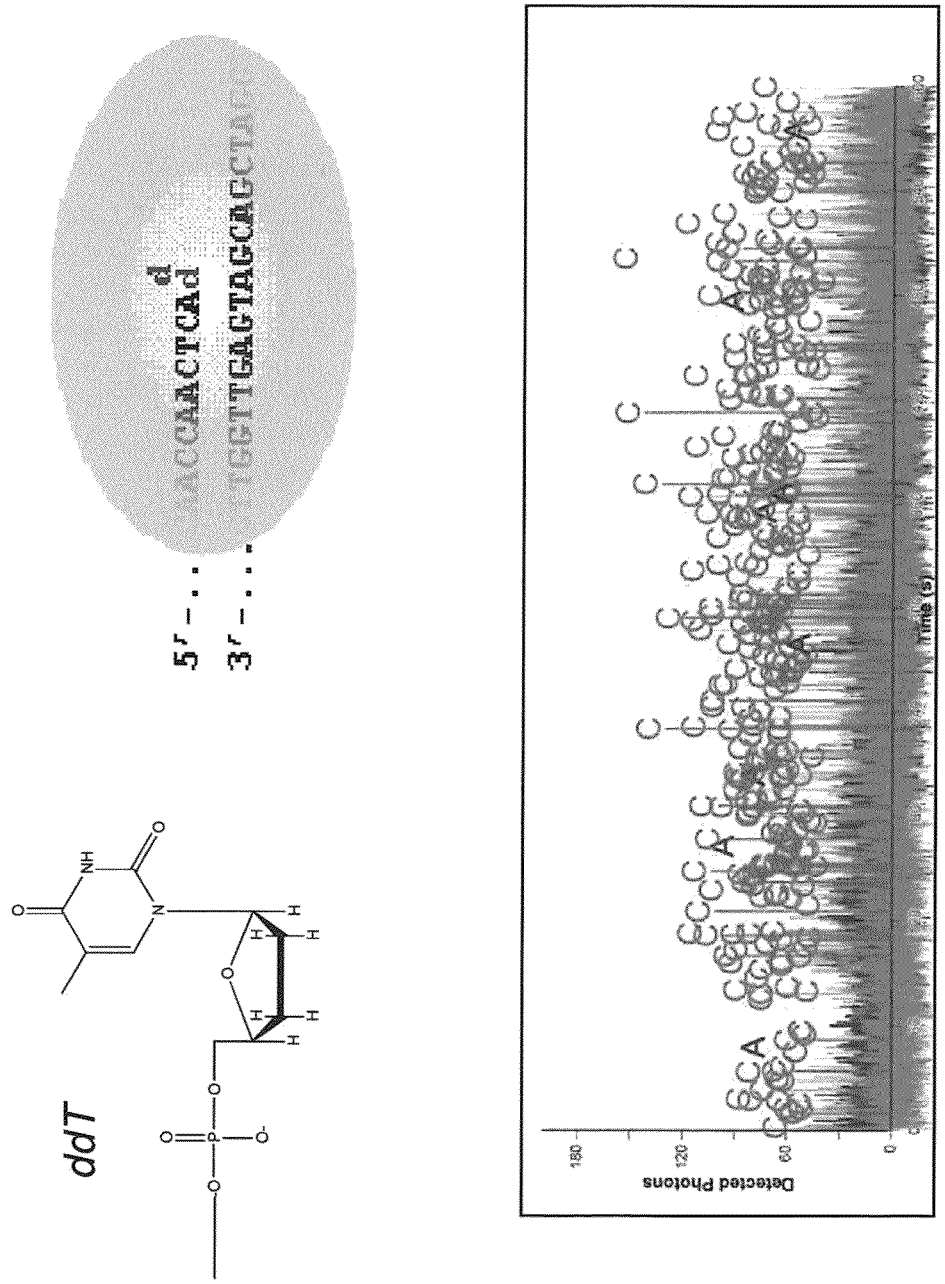
FIG. 8 shows the structure of ddT, the position of ddT in the growing strand complementary to the template strand, and data showing the sampling of the next cognate nucleotide (C) in the growing strand.

FIG. 8 shows data obtained in a zero mode waveguide using a system such as described in Eid, J., et al., Science, 2009. 323: p. 133-38. A primer terminated with a dideoxy T is hybridized with a template nucleic acid and is complexed with a polymerase enzyme that is bound to the base of a ZMW. The next base in the template nucleic acid is a G. The enzyme complex is exposed to a reaction mixture having the nucleotide analogs dC6P-AF555 and dA6P-AF647. Each analog has a 6 phosphate polyphosphate group at its 5' position with a label at the end of the polyphosphate. The label for the C analog is Alexa 555, and the label for the A analog is Alexa 647. For this template and primer, dC6P-AF555 is the cognate nucleotide analog. It can be seen from the data that the cognate nucleotide analog can be readily distinguished from the non-cognate analog, showing that the next base in the template is a G. This demonstrates how cognate sampling can be used to identify a base in a template nucleic acid.

Figure 9:
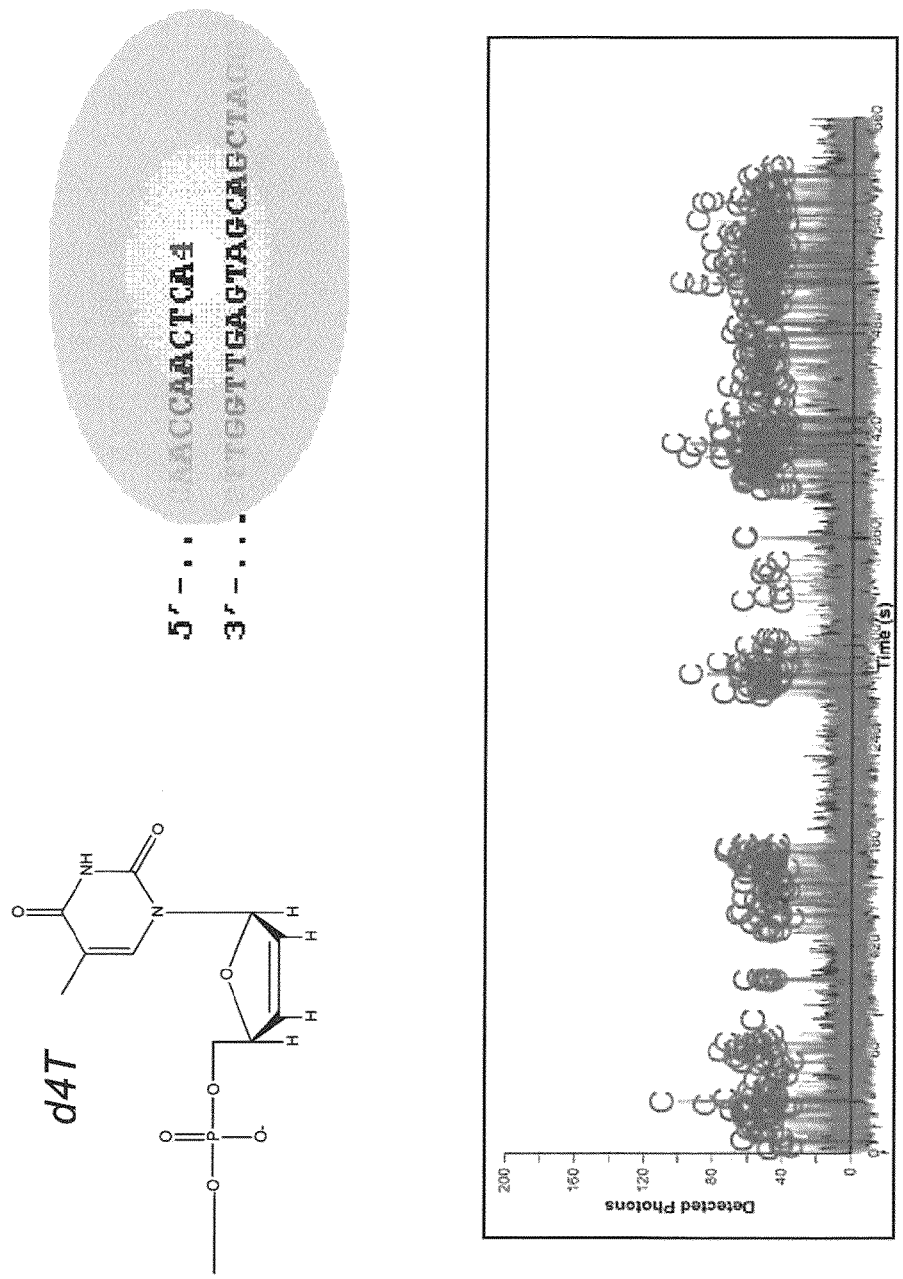
FIG. 9 shows the structure of d4T, the position of d4T in the growing strand complementary to the template strand, and data showing the sampling of the next cognate nucleotide (C) in the growing strand.
Figure 10:
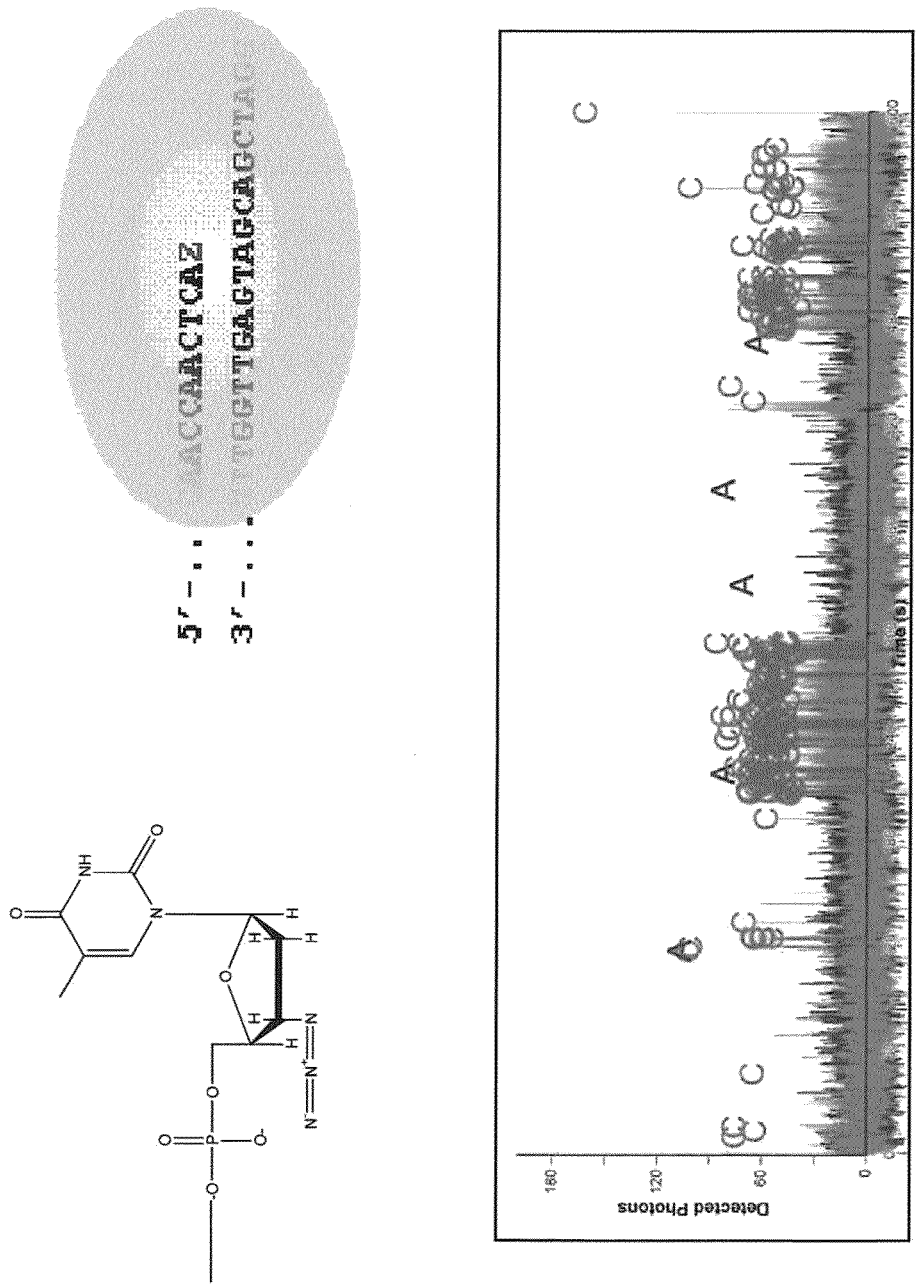
FIG. 10 shows the structure of AZT, the position of AZT in the growing strand complementary to the template strand, and data showing the sampling of the next cognate nucleotide (C) in the growing strand.

In addition, we have found that when the primer is terminated by different terminators, the characteristics of the signal from the cognate sampling can vary. Here, this difference in the signal appears to show aspects of translocation dynamics of the polymerase enzyme. Generally a template that is held by a polymerase can exist in either the P site, during which can undergo sampling, or the template can be in the N site, effectively closing off the association of the next nucleotide analog. The template equilibrates between these two sites prior to the addition of the next nucleotide in the chain. FIGS. 8, 9, and 10 show data for primers terminated with ddT, d4T and AZT respectively. The binding dynamics of the three differently terminated primers differs dramatically. An explanation for the observed kinetics is that the time scale for the template DNA to move between the N and the P sites in the polymerase is different for each of these terminators. Note, for example, that the AZT terminated sample has long lengths of time in which very little sampling is occurring indicating that the template-primer resides in the N site for these long stretches of time. These figures show how cognate sampling can be used to identify the manner in which the primer is terminated in addition to identifying the identity of the cognate base. The method can be used for drug discovery by looking at other terminators to determine their behavior under these conditions.

The methods of the invention allow for multiplexing so as to identify the presence of a sequence within a template nucleic acid or set of template nucleic acids. For example, a sample has one or more viruses such as an HN1 or HN2 virus. An analysis is performed using two primers, a first primer specific to HN1 for which the next base is, e.g. an A, and a second primer for HN2 for which the next base is a T. The nucleic acids from the sample are fragmented, mixed with the primer mixture, complexed with the enzyme, and loaded onto a ZMW chip. The wells with active enzyme are observed by cognate sampling. If substantially all A, then HN1, if substantially all T, then HN2. If there is a mixture, in some cases, the relative levels of the viruses can be determined. This process can be multiplexed across a plurality of samples allowing in each case for a specific base call, which in the aggregate will provide information about the identity of nucleic acid samples.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method comprising:
   providing a polymerase enzyme complex comprising a template nucleic acid, a primer, and a polymerase enzyme under conditions wherein the interactions between a single polymerase and a labeled nucleotide analog can be monitored;
   exposing the polymerase enzyme complex to one or more labeled nucleotide analogs in solution under conditions wherein the nucleotide analogs are unincorporatable;
   observing the transient binding of the one or more labeled unincorporatable nucleotide analogs over time; and
   using the observed transient binding to provide information about the enzyme, template nucleic acid, primer, or nucleotide analog or analogs.

2. The method of claim 1 wherein the primer is terminated, rendering the nucleotide analogs unincorporatable.

3. The method of claim 1 wherein the method is carried out with a plurality of nucleotide analogs, and the transient binding over time is used to determine the effect of nucleotide structure on enzyme performance.

4. A method for identifying a base in a template nucleic acid comprising:
   providing a polymerase enzyme complex comprising a template nucleic acid, a primer, and a polymerase enzyme;
   exposing the polymerase enzyme complex to one or more labeled nucleotide analogs in solution under conditions wherein the nucleotide analogs are unincorporatable, wherein one of the labeled unincorporatable nucleotide analogs is a cognate nucleotide analog; and
   detecting multiple transient binding events corresponding to the binding or a labeled unincorporatable cognate nucleotide analog to the polymerase complex, thereby identifying the base corresponding to the cognate nucleotide analog in the template nucleic acid.

5. The method of claim 4 wherein the polymerase enzyme complex comprises a single polymerase molecule.

6. The method of claim 4 wherein the polymerase enzyme complex is immobilized on a substrate.

7. The method of claim 4 wherein the polymerase enzyme complex is immobilized in an optical confinement.

8. The method of claim 4 wherein at least a first and second primer are provided, wherein each of the primers are selected to bind to a known nucleotide sequence in which the identity of the base in the nucleotide sequence corresponding to the next cognate nucleotide is known and is different for the different primers; and wherein the polymerase enzyme complex is exposed to two or more labeled unincorporatable, nucleotide analogs, wherein the two or more labeled unincorporatable nucleotides comprise the next cognate nucleotides for the two primers.

\* \* \* \* \*